United States Patent [19]
Giordano

[11] Patent Number: 5,840,506
[45] Date of Patent: Nov. 24, 1998

[54] METHODS FOR THE DIAGNOSIS AND PROGNOSIS OF CANCER

[75] Inventor: Antonio Giordano, Philadelphia, Pa.

[73] Assignee: Thomas Jefferson University, Philadelphia, Pa.

[21] Appl. No.: 832,877

[22] Filed: Apr. 4, 1997

Related U.S. Application Data

[60] Provisional application No. 60/039,532 Mar. 3, 1997 and provisional application No. 60/020,196 Jun. 21, 1996 and provisional application No. 60/019,372 Jun. 5, 1996.

[51] Int. Cl.⁶ .................................................. G01N 33/574
[52] U.S. Cl. ........................... 435/7.23; 435/6; 435/7.1; 435/7.9; 435/7.91; 435/7.92; 435/7.93; 435/7.94; 435/7.95; 436/518; 530/387.7
[58] Field of Search ................ 530/387.7; 436/518–523; 435/6, 7.1, 7.2, 7.21, 7.23, 7.9–7.95

[56] References Cited

U.S. PATENT DOCUMENTS 5,532,340   7/1996   Giordano ................................ 530/350

FOREIGN PATENT DOCUMENTS 0 390 530   10/1990   European Pat. Off. .

OTHER PUBLICATIONS

Esposito et al., *Modern Pathology* 10(1):163A #955 (Jan. 1997).
Esposito et al., *Annual Congress European Respiratory Society* Abstract #176 (Sep. 1996).
Depasquale et al., *Modern Pathology* 10(1) 98A #568 (Jan. 1997).
Baldi et al., *Clinical Cancer Research* 2(7):1239–1245 (Jul. 1996).
Esposito et al., *International Journal of Oncology* 9:439–443 (1996).
Xu et al., *Journal of the National Cancer Institute* 86(9):695–699 (May 4, 1994).
Yokota et al., *Oncogene* 3:471–475 (1988).
Harbour et al., *Science* 241:353–357 (15 Jul. 1988).
Higashiyama et al., *Oncology* 51:544–551 (1994).
Baldi et al., *Journal of Cellular Biochemistry* 59:402–408 (1995).
Claudio et al., *Cancer Research* 54:5556–5560 (Nov. 1, 1994).
Sang et al., *Molecular and Cellular Differentiation* 3(1):1–29 (1995).
Caputi et al., *II Congresso Società Italiana Medicina Respiratorie* (Simer) Abstract p. 27, (Oct. 1996).
Xu et al., *Cancer Research* 51:2735–2739 (May 15, 1991).
Karpeh et al British Journal of Cancer vol. 72 p. 986, 1995.
Teneriello et al American Association for Cancer Reasearch vol. 35 p. 224 Abstract 1337, Apr. 1994.

*Primary Examiner*—Sheela Huff
*Attorney, Agent, or Firm*—Seidel, Gonda, Lavorgna & Monaco, PC

[57] ABSTRACT

The invention provides diagnostic and prognostic methods which comprise determining the level of expression of the tumor suppressor gene pRb2/p130. Because the relative level of pRb2/p130 expression correlates with tumor grade and patient prognosis, these methods may be used to detect the presence of cancer, to make treatment decisions, and to predict the risk of cancer in disease-free individuals.

34 Claims, 5 Drawing Sheets

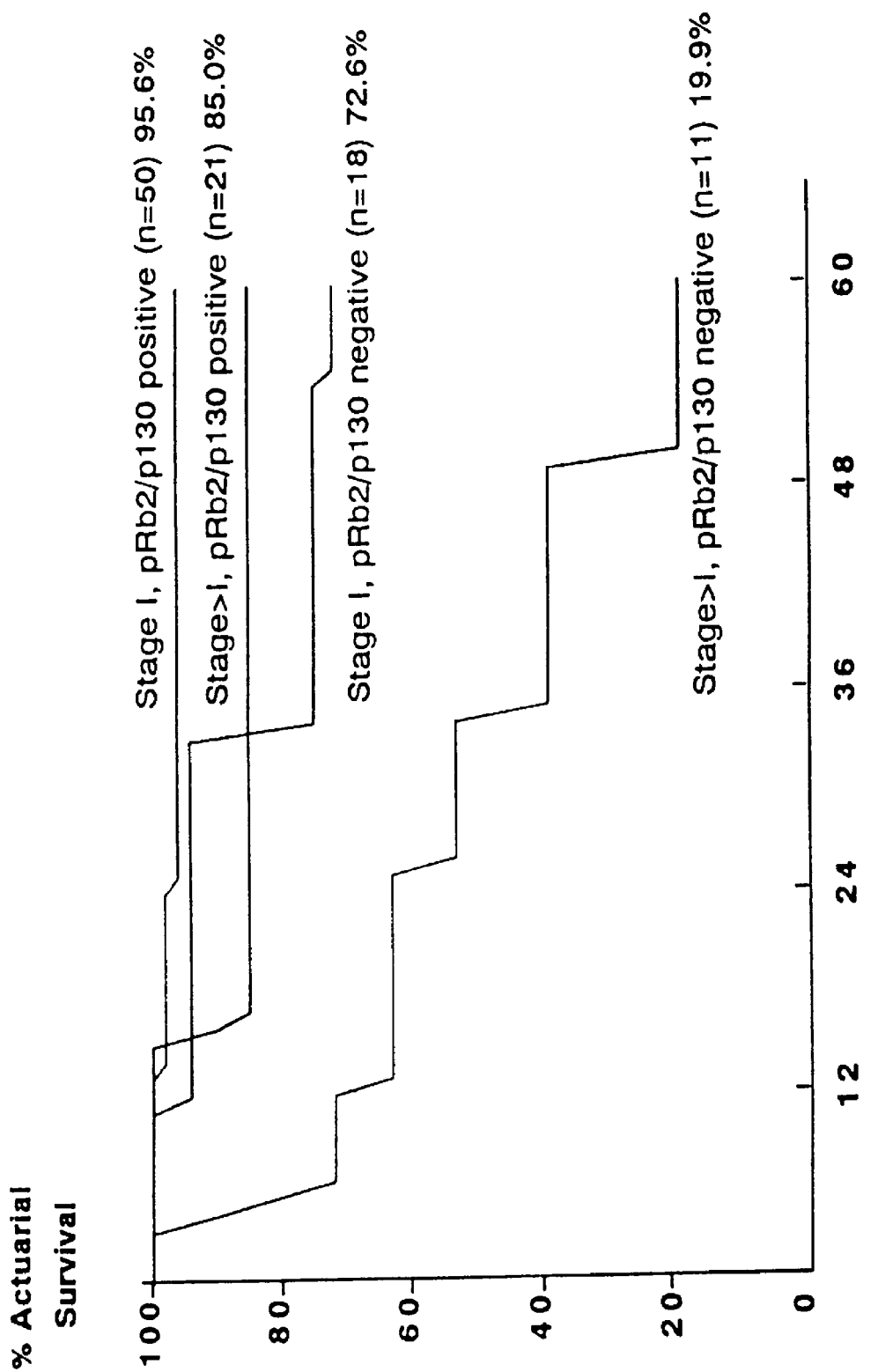

```
-311  CAGCCCTGTTGAATGTTCTCACGGTGGGGAGGTACGTGTTTAAAATACGG

-261  GGAAGGTGCTTTTATTTCACCCCTGGTGAAACTAGGGGAGCTAATTTTTT

-211  TAAACATGATTTTTGTCCCCCTTGAACCGCCGGCCTGGACTACGTTTCCC
                                             Ker1
-161  AGCAGCCCTGTGCTCAAGACTACGGGT GCCTGCAGGC GGTCAGCGTCGTTT
                    ⟶              Sp1              Sp1
-111  GCGACGGCGCAGACGCGGTGC GGGCGG CGGAC GGGCGG CGCTTCGCCGT
                                            MyoD
 -61  TTGAATTGCTGCGGGCCCGGGCCCTCACCT CACCTG AGGTCCGGCCGCCC

-11  AGGGGTGCGCT ATG CCGTCGGGAGGTGACCAGTCGCCACCGCCCCCGCCT
                  M   P   S   G   G   D   Q   S   P   P   P   P   P

40  CCCCCTCCGGCGGCGGCAGCCTCGGATGAGGAGGAGGAGGACGACGGCGA
       P   P   P   A   A   A   A   S   D   E   E   E   E   D   D   G   E

90  GGCGGAAGACGCCGCGCCGTCTGCCGAGTCGCCCACCCCTCAGATCCAGC
       A   E   D   A   A   P   S   A   E   S   P   T   P   Q   I   Q

140  AGCGGTTCGACGAGCTGTGCAGCCGCCTCAACATGGACGAGGCGGCGCGG
       Q   R   F   D   E   L   C   S   R   L   N   M   D   E   A   A   R

190  CCCGAGGCCTGGGACAGCTACCGCAGCATGAGCGAAAGCTACACGCTGGA
       P   E   A   W   D   S   Y   R   S   M   S   E   S   Y   T   L   E

240  Ggtgcgctcgc
```

FIG. 4

SEQUENCE LISTING ( 1 ) GENERAL INFORMATION:

( i i i ) NUMBER OF SEQUENCES: 116

( 2 ) INFORMATION FOR SEQ ID NO:1:

( i ) SEQUENCE CHARACTERISTICS:
    ( A ) LENGTH: 4853 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 70..3489

( x i ) SEQUENCE DESCRIPTION: SEQ ID NO:1:

```
TTCGCCGTTT  GAATTGCTGC  GGGCCCGGGC  CCTCACCTCA  CCTGAGGTCC  GGCCGCCCAG              60

GGGTGCGCT ATG CCG TCG GGA GGT GAC CAG TCG CCA CCG CCC CCG CCT                      108
          Met Pro Ser Gly Gly Asp Gln Ser Pro Pro Pro Pro Pro
          1               5                   10

CCC CCT CCG GCG GCG GCA GCC TCG GAT GAG GAG GAG GAG GAC GAC GGC                    156
Pro Pro Pro Ala Ala Ala Ala Ser Asp Glu Glu Glu Glu Asp Asp Gly
        15                  20                  25

GAG GCG GAA GAC GCC GCG CCG TCT GCC GAG TCG CCC ACC CCT CAG ATC                    204
Glu Ala Glu Asp Ala Ala Pro Ser Ala Glu Ser Pro Thr Pro Gln Ile
30                  35                  40                  45

CAG CAG CGG TTC GAC GAG CTG TGC AGC CGC CTC AAC ATG GAC GAG GCG                    252
Gln Gln Arg Phe Asp Glu Leu Cys Ser Arg Leu Asn Met Asp Glu Ala
                50                  55                  60

GCG CGG CCC GAG GCC TGG GAC AGC TAC CGC AGC ATG AGC GAA AGC TAC                    300
Ala Arg Pro Glu Ala Trp Asp Ser Tyr Arg Ser Met Ser Glu Ser Tyr
            65                  70                  75

ACG CTG GAG GGA AAT GAT CTT CAT TGG TTA GCA TGT GCC TTA TAT GTG                    348
Thr Leu Glu Gly Asn Asp Leu His Trp Leu Ala Cys Ala Leu Tyr Val
        80                  85                  90

GCT TGC AGA AAA TCT GTT CCA ACT GTA AGC AAA GGG ACA GTG GAA GGA                    396
Ala Cys Arg Lys Ser Val Pro Thr Val Ser Lys Gly Thr Val Glu Gly
    95                  100                 105

AAC TAT GTA TCT TTA ACT AGA ATC CTG AAA TGT TCA GAG CAG AGC TTA                    444
Asn Tyr Val Ser Leu Thr Arg Ile Leu Lys Cys Ser Glu Gln Ser Leu
110                 115                 120                 125

ATC GAA TTT TTT AAT AAG ATG AAG AAG TGG GAA GAC ATG GCA AAT CTA                    492
Ile Glu Phe Phe Asn Lys Met Lys Lys Trp Glu Asp Met Ala Asn Leu
                130                 135                 140

CCC CCA CAT TTC AGA GAA CGT ACT GAG AGA TTA GAA AGA AAC TTC ACT                    540
Pro Pro His Phe Arg Glu Arg Thr Glu Arg Leu Glu Arg Asn Phe Thr
            145                 150                 155

GTT TCT GCT GTA ATT TTT AAG AAA TAT GAA CCC ATT TTT CAG GAC ATC                    588
Val Ser Ala Val Ile Phe Lys Lys Tyr Glu Pro Ile Phe Gln Asp Ile
        160                 165                 170

TTT AAA TAC CCT CAA GAG GAG CAA CCT CGT CAG CAG CGA GGA AGG AAA                    636
Phe Lys Tyr Pro Gln Glu Glu Gln Pro Arg Gln Gln Arg Gly Arg Lys
    175                 180                 185

CAG CGG CGA CAG CCC TGT ACT GTG TCT GAA ATT TTC CAT TTT TGT TGG                    684
Gln Arg Arg Gln Pro Cys Thr Val Ser Glu Ile Phe His Phe Cys Trp
190                 195                 200                 205

GTG CTT TTT ATA TAT GCA AAA GGT AAT TTC CCC ATG ATT AGT GAT GAT                    732
Val Leu Phe Ile Tyr Ala Lys Gly Asn Phe Pro Met Ile Ser Asp Asp
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 210 |     |     |     |     | 215 |     |     |     |     | 220 |     |      |
| TTG | GTC | AAT | TCT | TAT | CAC | CTG | CTG | CTG | TGT | GCT | TTG | GAC | TTA | GTT | TAT | 780  |
| Leu | Val | Asn | Ser 225 | Tyr | His | Leu | Leu 230 | Leu | Cys | Ala | Leu | Asp | Leu 235 | Val | Tyr | |
| GGA | AAT | GCA | CTT | CAG | TGT | TCT | AAT | CGT | AAA | GAA | CTT | GTG | AAC | CCT | AAT | 828 |
| Gly | Asn | Ala 240 | Leu | Gln | Cys | Ser | Asn 245 | Arg | Lys | Glu | Leu | Val 250 | Asn | Pro | Asn | |
| TTT | AAA | GGC | TTA | TCT | GAA | GAT | TTT | CAT | GCT | AAA | GAT | TCT | AAA | CCT | TCC | 876 |
| Phe | Lys 255 | Gly | Leu | Ser | Glu | Asp 260 | Phe | His | Ala | Lys | Asp 265 | Ser | Lys | Pro | Ser | |
| TCT | GAC | CCC | CCT | TGT | ATC | ATT | GAG | AAA | CTG | TGT | TCC | TTA | CAT | GAT | GGC | 924 |
| Ser 270 | Asp | Pro | Pro | Cys | Ile 275 | Ile | Glu | Lys | Leu | Cys 280 | Ser | Leu | His | Asp | Gly 285 | |
| CTA | GTT | TTG | GAA | GCA | AAG | GGG | ATA | AAG | GAA | CAT | TTC | TGG | AAA | CCC | TAT | 972 |
| Leu | Val | Leu | Glu | Ala 290 | Lys | Gly | Ile | Lys | Glu 295 | His | Phe | Trp | Lys | Pro 300 | Tyr | |
| ATT | AGG | AAA | CTT | TAT | GAA | AAA | AAG | CTC | CTT | AAG | GGA | AAA | GAA | GAA | AAT | 1020 |
| Ile | Arg | Lys | Leu 305 | Tyr | Glu | Lys | Lys | Leu 310 | Leu | Lys | Gly | Lys | Glu 315 | Glu | Asn | |
| CTC | ACT | GGG | TTT | CTA | GAA | CCT | GGG | AAC | TTT | GGA | GAG | AGT | TTT | AAA | GCC | 1068 |
| Leu | Thr | Gly 320 | Phe | Leu | Glu | Pro | Gly 325 | Asn | Phe | Gly | Glu | Ser 330 | Phe | Lys | Ala | |
| ATC | AAT | AAG | GCC | TAT | GAG | GAG | TAT | GTT | TTA | TCT | GTT | GGG | AAT | TTA | GAT | 1116 |
| Ile | Asn | Lys 335 | Ala | Tyr | Glu | Glu | Tyr 340 | Val | Leu | Ser | Val | Gly 345 | Asn | Leu | Asp | |
| GAG | CGG | ATA | TTT | CTT | GGA | GAG | GAT | GCT | GAG | GAG | GAA | ATT | GGG | ACT | CTC | 1164 |
| Glu 350 | Arg | Ile | Phe | Leu | Gly 355 | Glu | Asp | Ala | Glu | Glu 360 | Glu | Ile | Gly | Thr | Leu 365 | |
| TCA | AGG | TGT | CTG | AAC | GCT | GGT | TCA | GGA | ACA | GAG | ACT | GCT | GAA | AGG | GTG | 1212 |
| Ser | Arg | Cys | Leu | Asn 370 | Ala | Gly | Ser | Gly | Thr 375 | Glu | Thr | Ala | Glu | Arg 380 | Val | |
| CAG | ATG | AAA | AAC | ATC | TTA | CAG | CAG | CAT | TTT | GAC | AAG | TCC | AAA | GCA | CTT | 1260 |
| Gln | Met | Lys | Asn 385 | Ile | Leu | Gln | Gln | His 390 | Phe | Asp | Lys | Ser | Lys 395 | Ala | Leu | |
| AGA | ATC | TCC | ACA | CCA | CTA | ACT | GGT | GTT | AGG | TAC | ATT | AAG | GAG | AAT | AGC | 1308 |
| Arg | Ile | Ser | Thr 400 | Pro | Leu | Thr | Gly | Val 405 | Arg | Tyr | Ile | Lys | Glu 410 | Asn | Ser | |
| CCT | TGT | GTG | ACT | CCA | GTT | TCT | ACA | GCT | ACG | CAT | AGC | TTG | AGT | CGT | CTT | 1356 |
| Pro | Cys | Val 415 | Thr | Pro | Val | Ser | Thr 420 | Ala | Thr | His | Ser | Leu 425 | Ser | Arg | Leu | |
| CAC | ACC | ATG | CTG | ACA | GGC | CTC | AGG | AAT | GCA | CCA | AGT | GAG | AAA | CTG | GAA | 1404 |
| His 430 | Thr | Met | Leu | Thr | Gly 435 | Leu | Arg | Asn | Ala | Pro 440 | Ser | Glu | Lys | Leu | Glu 445 | |
| CAG | ATT | CTC | AGG | ACA | TGT | TCC | AGA | GAT | CCA | ACC | CAG | GCT | ATT | GCT | AAC | 1452 |
| Gln | Ile | Leu | Arg | Thr 450 | Cys | Ser | Arg | Asp | Pro 455 | Thr | Gln | Ala | Ile | Ala 460 | Asn | |
| AGA | CTG | AAA | GAA | ATG | TTT | GAA | ATA | TAT | TCT | CAG | CAT | TTC | CAG | CCA | GAC | 1500 |
| Arg | Leu | Lys | Glu | Met 465 | Phe | Glu | Ile | Tyr | Ser 470 | Gln | His | Phe | Gln | Pro 475 | Asp | |
| GAG | GAT | TTC | AGT | AAT | TGT | GCT | AAA | GAA | ATT | GCC | AGC | AAA | CAT | TTT | CGT | 1548 |
| Glu | Asp | Phe | Ser 480 | Asn | Cys | Ala | Lys | Glu 485 | Ile | Ala | Ser | Lys | His 490 | Phe | Arg | |
| TTT | GCG | GAG | ATG | CTT | TAC | TAT | AAA | GTA | TTA | GAA | TCT | GTT | ATT | GAG | CAG | 1596 |
| Phe | Ala | Glu | Met | Leu 495 | Tyr | Tyr | Lys | Val | Leu 500 | Glu | Ser | Val | Ile | Glu 505 | Gln | |
| GAA | CAA | AAA | AGA | CTA | GGA | GAC | ATG | GAT | TTA | TCT | GGT | ATT | CTG | GAA | CAA | 1644 |
| Glu | Gln | Lys | Arg | Leu 510 | Gly | Asp | Met | Asp | Leu 515 | Ser | Gly | Ile | Leu | Glu 520 | Gln 525 | |
| GAT | GCA | TTC | CAC | AGA | TCT | CTC | TTG | GCC | TGC | TGC | CTT | GAG | GTC | GTC | ACT | 1692 |
| Asp | Ala | Phe | His | Arg | Ser | Leu | Leu | Ala | Cys | Cys | Leu | Glu | Val | Val | Thr | |

|     |     |     |     | 530 |     |     |     |     | 535 |     |     |     |     | 540 |     |      |
|-----|-----|-----|-----|-----|-----|-----|-----|-----|-----|-----|-----|-----|-----|-----|-----|------|
| TTT | TCT | TAT | AAG | CCT | CCT | GGG | AAT | TTT | CCA | TTT | ATT | ACT | GAA | ATA | TTT | 1740 |
| Phe | Ser | Tyr | Lys | Pro | Pro | Gly | Asn | Phe | Pro | Phe | Ile | Thr | Glu | Ile | Phe |      |
|     |     |     | 545 |     |     |     |     | 550 |     |     |     |     | 555 |     |     |      |
| GAT | GTG | CCT | CTT | TAT | CAT | TTT | TAT | AAG | GTG | ATA | GAA | GTA | TTC | ATT | AGA | 1788 |
| Asp | Val | Pro | Leu | Tyr | His | Phe | Tyr | Lys | Val | Ile | Glu | Val | Phe | Ile | Arg |      |
|     |     | 560 |     |     |     |     | 565 |     |     |     |     | 570 |     |     |     |      |
| GCA | GAA | GAT | GGC | CTT | TGT | AGA | GAG | GTG | GTA | AAA | CAC | CTT | AAT | CAG | ATT | 1836 |
| Ala | Glu | Asp | Gly | Leu | Cys | Arg | Glu | Val | Val | Lys | His | Leu | Asn | Gln | Ile |      |
|     | 575 |     |     |     |     | 580 |     |     |     |     | 585 |     |     |     |     |      |
| GAA | GAA | CAG | ATC | TTA | GAT | CAT | TTG | GCA | TGG | AAA | CCA | GAG | TCT | CCA | CTC | 1884 |
| Glu | Glu | Gln | Ile | Leu | Asp | His | Leu | Ala | Trp | Lys | Pro | Glu | Ser | Pro | Leu |      |
| 590 |     |     |     |     | 595 |     |     |     | 600 |     |     |     |     |     | 605 |      |
| TGG | GAA | AAA | ATT | AGA | GAC | AAT | GAA | AAC | AGA | GTT | CCT | ACA | TGT | GAA | GAG | 1932 |
| Trp | Glu | Lys | Ile | Arg | Asp | Asn | Glu | Asn | Arg | Val | Pro | Thr | Cys | Glu | Glu |      |
|     |     |     |     | 610 |     |     |     |     | 615 |     |     |     |     | 620 |     |      |
| GTC | ATG | CCA | CCT | CAG | AAC | CTG | GAA | AGG | GCA | GAT | GAA | ATT | TGC | ATT | GCT | 1980 |
| Val | Met | Pro | Pro | Gln | Asn | Leu | Glu | Arg | Ala | Asp | Glu | Ile | Cys | Ile | Ala |      |
|     |     |     | 625 |     |     |     |     |     | 630 |     |     |     | 635 |     |     |      |
| GGC | TCC | CCT | TTG | ACT | CCC | AGA | AGG | GTG | ACT | GAA | GTT | CGT | GCT | GAT | ACT | 2028 |
| Gly | Ser | Pro | Leu | Thr | Pro | Arg | Arg | Val | Thr | Glu | Val | Arg | Ala | Asp | Thr |      |
|     |     | 640 |     |     |     |     | 645 |     |     |     |     | 650 |     |     |     |      |
| GGA | GGA | CTT | GGA | AGG | AGC | ATA | ACA | TCT | CCA | ACC | ACA | TTA | TAC | GAT | AGG | 2076 |
| Gly | Gly | Leu | Gly | Arg | Ser | Ile | Thr | Ser | Pro | Thr | Thr | Leu | Tyr | Asp | Arg |      |
|     | 655 |     |     |     |     | 660 |     |     |     |     | 665 |     |     |     |     |      |
| TAC | AGC | TCC | CCA | CCA | GCC | AGC | ACT | ACC | AGA | AGG | CGG | CTA | TTT | GTT | GAG | 2124 |
| Tyr | Ser | Ser | Pro | Pro | Ala | Ser | Thr | Thr | Arg | Arg | Arg | Leu | Phe | Val | Glu |      |
| 670 |     |     |     |     | 675 |     |     |     |     | 680 |     |     |     |     | 685 |      |
| AAT | GAT | AGC | CCC | TCT | GAT | GGA | GGG | ACG | CCT | GGG | CGC | ATG | CCC | CCA | CAG | 2172 |
| Asn | Asp | Ser | Pro | Ser | Asp | Gly | Gly | Thr | Pro | Gly | Arg | Met | Pro | Pro | Gln |      |
|     |     |     |     | 690 |     |     |     |     | 695 |     |     |     |     | 700 |     |      |
| CCC | CTA | GTC | AAT | GCT | GTC | CCT | GTG | CAG | AAT | GTA | TCT | GGG | GAG | ACT | GTT | 2220 |
| Pro | Leu | Val | Asn | Ala | Val | Pro | Val | Gln | Asn | Val | Ser | Gly | Glu | Thr | Val |      |
|     |     |     | 705 |     |     |     |     | 710 |     |     |     |     | 715 |     |     |      |
| TCT | GTC | ACA | CCA | GTT | CCT | GGA | CAG | ACT | TTG | GTC | ACC | ATG | GCA | ACC | GCC | 2268 |
| Ser | Val | Thr | Pro | Val | Pro | Gly | Gln | Thr | Leu | Val | Thr | Met | Ala | Thr | Ala |      |
|     |     | 720 |     |     |     |     | 725 |     |     |     |     | 730 |     |     |     |      |
| ACT | GTC | ACA | GCC | AAC | AAT | GGG | CAA | ACG | GTA | ACC | ATT | CCT | GTG | CAA | GGT | 2316 |
| Thr | Val | Thr | Ala | Asn | Asn | Gly | Gln | Thr | Val | Thr | Ile | Pro | Val | Gln | Gly |      |
| 735 |     |     |     |     | 740 |     |     |     |     | 745 |     |     |     |     |     |      |
| ATT | GCC | AAT | GAA | AAT | GGA | GGG | ATA | ACA | TTC | TTC | CCT | GTC | CAA | GTC | AAT | 2364 |
| Ile | Ala | Asn | Glu | Asn | Gly | Gly | Ile | Thr | Phe | Phe | Pro | Val | Gln | Val | Asn |      |
| 750 |     |     |     |     | 755 |     |     |     |     | 760 |     |     |     |     | 765 |      |
| GTT | GGG | GGG | CAG | GCA | CAA | GCT | GTG | ACA | GGC | TCC | ATC | CAG | CCC | CTC | AGT | 2412 |
| Val | Gly | Gly | Gln | Ala | Gln | Ala | Val | Thr | Gly | Ser | Ile | Gln | Pro | Leu | Ser |      |
|     |     |     |     | 770 |     |     |     |     | 775 |     |     |     |     | 780 |     |      |
| GCT | CAG | GCC | CTG | GCT | GGA | AGT | CTG | AGC | TCT | CAA | CAG | GTG | ACA | GGA | ACA | 2460 |
| Ala | Gln | Ala | Leu | Ala | Gly | Ser | Leu | Ser | Ser | Gln | Gln | Val | Thr | Gly | Thr |      |
|     |     |     | 785 |     |     |     |     | 790 |     |     |     |     | 795 |     |     |      |
| ACT | TTG | CAA | GTC | CCT | GGT | CAA | GTG | GCC | ATT | CAA | CAG | ATT | TCC | CCA | GGT | 2508 |
| Thr | Leu | Gln | Val | Pro | Gly | Gln | Val | Ala | Ile | Gln | Gln | Ile | Ser | Pro | Gly |      |
|     |     | 800 |     |     |     |     | 805 |     |     |     |     | 810 |     |     |     |      |
| GGC | CAA | CAG | CAG | AAG | CAA | GGC | CAG | TCT | GTA | ACC | AGC | AGT | AGT | AAT | AGA | 2556 |
| Gly | Gln | Gln | Gln | Lys | Gln | Gly | Gln | Ser | Val | Thr | Ser | Ser | Ser | Asn | Arg |      |
|     | 815 |     |     |     |     | 820 |     |     |     |     | 825 |     |     |     |     |      |
| CCC | AGG | AAG | ACC | AGC | TCT | TTA | TCG | CTT | TTC | TTT | AGA | AAG | GTA | TAC | CAT | 2604 |
| Pro | Arg | Lys | Thr | Ser | Ser | Leu | Ser | Leu | Phe | Phe | Arg | Lys | Val | Tyr | His |      |
| 830 |     |     |     |     | 835 |     |     |     |     | 840 |     |     |     |     | 845 |      |
| TTA | GCA | GCT | GTC | CGC | CTT | CGG | GAT | CTC | TGT | GCC | AAA | CTA | GAT | ATT | TCA | 2652 |
| Leu | Ala | Ala | Val | Arg | Leu | Arg | Asp | Leu | Cys | Ala | Lys | Leu | Asp | Ile | Ser |      |

-continued

```
                          850                              855                              860
GAT  GAA  TTG  AGG  AAA  AAA  ATC  TGG  ACC  TGC  TTT  GAA  TTC  TCC  ATA  ATT         2700
Asp  Glu  Leu  Arg  Lys  Lys  Ile  Trp  Thr  Cys  Phe  Glu  Phe  Ser  Ile  Ile
               865                 870                      875

CAG  TGT  CCT  GAA  CTT  ATG  ATG  GAC  AGA  CAT  CTG  GAC  CAG  TTA  TTA  ATG         2748
Gln  Cys  Pro  Glu  Leu  Met  Met  Asp  Arg  His  Leu  Asp  Gln  Leu  Leu  Met
               880                 885                      890

TGT  GCC  ATT  TAT  GTG  ATG  GCA  AAG  GTC  ACA  AAA  GAA  GAT  AAG  TCC  TTC         2796
Cys  Ala  Ile  Tyr  Val  Met  Ala  Lys  Val  Thr  Lys  Glu  Asp  Lys  Ser  Phe
               895                 900                      905

CAG  AAC  ATT  ATG  CGT  TGT  TAT  AGG  ACT  CAG  CCG  CAG  GCC  CGG  AGC  CAG         2844
Gln  Asn  Ile  Met  Arg  Cys  Tyr  Arg  Thr  Gln  Pro  Gln  Ala  Arg  Ser  Gln
     910                 915                      920                      925

GTG  TAT  AGA  AGT  GTT  TTG  ATA  AAA  GGG  AAA  AGA  AAA  AGA  AGA  AAT  TCT         2892
Val  Tyr  Arg  Ser  Val  Leu  Ile  Lys  Gly  Lys  Arg  Lys  Arg  Arg  Asn  Ser
               930                 935                      940

GGC  AGC  AGT  GAT  AGC  AGA  AGC  CAT  CAG  AAT  TCT  CCA  ACA  GAA  CTA  AAC         2940
Gly  Ser  Ser  Asp  Ser  Arg  Ser  His  Gln  Asn  Ser  Pro  Thr  Glu  Leu  Asn
               945                 950                      955

AAA  GAT  AGA  ACC  AGT  AGA  GAC  TCC  AGT  CCA  GTT  ATG  AGG  TCA  AGC  AGC         2988
Lys  Asp  Arg  Thr  Ser  Arg  Asp  Ser  Ser  Pro  Val  Met  Arg  Ser  Ser  Ser
     960                 965                      970

ACC  TTG  CCA  GTT  CCA  CAG  CCC  AGC  AGT  GCT  CCT  CCC  ACA  CCT  ACT  CGC         3036
Thr  Leu  Pro  Val  Pro  Gln  Pro  Ser  Ser  Ala  Pro  Pro  Thr  Pro  Thr  Arg
     975                 980                      985

CTC  ACA  GGT  GCC  AAC  AGT  GAC  ATG  GAA  GAA  GAG  GAG  AGG  GGA  GAC  CTC         3084
Leu  Thr  Gly  Ala  Asn  Ser  Asp  Met  Glu  Glu  Glu  Glu  Arg  Gly  Asp  Leu
990                      995                      1000                     1005

ATT  CAG  TTC  TAC  AAC  AAC  ATC  TAC  ATC  AAA  CAG  ATT  AAG  ACA  TTT  GCC         3132
Ile  Gln  Phe  Tyr  Asn  Asn  Ile  Tyr  Ile  Lys  Gln  Ile  Lys  Thr  Phe  Ala
                    1010                1015                      1020

ATG  AAG  TAC  TCA  CAG  GCA  AAT  ATG  GAT  GCT  CCT  CCA  CTC  TCT  CCC  TAT         3180
Met  Lys  Tyr  Ser  Gln  Ala  Asn  Met  Asp  Ala  Pro  Pro  Leu  Ser  Pro  Tyr
               1025                1030                      1035

CCA  TTT  GTA  AGA  ACA  GGC  TCC  CCT  CGC  CGA  ATA  CAG  TTG  TCT  CAA  AAT         3228
Pro  Phe  Val  Arg  Thr  Gly  Ser  Pro  Arg  Arg  Ile  Gln  Leu  Ser  Gln  Asn
               1040                1045                      1050

CAT  CCT  GTC  TAC  ATT  TCC  CCA  CAT  AAA  AAT  GAA  ACA  ATG  CTT  TCT  CCT         3276
His  Pro  Val  Tyr  Ile  Ser  Pro  His  Lys  Asn  Glu  Thr  Met  Leu  Ser  Pro
               1055                1060                      1065

CGA  GAA  AAG  ATT  TTC  TAT  TAC  TTC  AGC  AAC  AGT  CCT  TCA  AAG  AGA  CTG         3324
Arg  Glu  Lys  Ile  Phe  Tyr  Tyr  Phe  Ser  Asn  Ser  Pro  Ser  Lys  Arg  Leu
1070                     1075                     1080                     1085

AGA  GAA  ATT  AAT  AGT  ATG  ATA  CGC  ACA  GGA  GAA  ACT  CCT  ACT  AAA  AAG         3372
Arg  Glu  Ile  Asn  Ser  Met  Ile  Arg  Thr  Gly  Glu  Thr  Pro  Thr  Lys  Lys
                    1090                1095                      1100

AGA  GGA  ATT  CTT  TTG  GAA  GAT  GGA  AGT  GAA  TCA  CCT  GCA  AAA  AGA  ATT         3420
Arg  Gly  Ile  Leu  Leu  Glu  Asp  Gly  Ser  Glu  Ser  Pro  Ala  Lys  Arg  Ile
               1105                1110                      1115

TGC  CCA  GAA  AAT  CAT  TCT  GCC  TTA  TTA  CGC  CGT  CTC  CAA  GAT  GTA  GCT         3468
Cys  Pro  Glu  Asn  His  Ser  Ala  Leu  Leu  Arg  Arg  Leu  Gln  Asp  Val  Ala
               1120                1125                      1130

AAT  GAC  CGT  GGT  TCC  CAC  TGA  GGTTAGTCTC  TTGTATTAAA  CTCTTCACAA               3519
Asn  Asp  Arg  Gly  Ser  His   *
               1135                1140

AATCTGTTTA  GCAGCAGCCT  TTAATGCATC  TAGATTATGG  AGCTTTTTC  CTTAATCCAG              3579

CTGATGAGTT  ACAGCCTGTT  AGTAACATGA  GGGGACATTT  TGGTGAGAAA  TGGGACTTAA              3639

CTCCTTCCAG  TGTCCTTAGA  ACATTTTAAT  TCATCCCAAC  TGTCTTTTTT  TCCCTACCAC              3699
```

```
TCAGTGATTA  CTGTCAAGGC  TGCTTACAAT  CCAAACTTGG  GTTTTTGGCT  CTGGCAAAGC   3759
TTTTAGAAAT  ACTGCAAGAA  ATGATGTGTA  CCCAACGTGA  GCATAGGAGG  CTTCTGTTGA   3819
CGTCTCCAAC  AGAAGAACTG  TGTTTCAAGT  TCAATCCTAC  CTGTTTTGTG  GTCAGCTGTA   3879
GTCCTCATAA  AAAGCAAAAC  AAAAATTAGG  TATTTGTCC   TAAAACACCT  GGTAGGAGTG   3939
TGTGATTTTT  TGCATTCCTG  ACAAGGAGA   GCACACCCAG  GTTTGGAGGT  CCTAGGTCAT   3999
TAGCCCTCGT  CTCCCGTTCC  CTTTGTGCAC  ATCTTCCCTC  TCCCCATTCG  GTGTGGTGCA   4059
GTGTGAAAAG  TCCTTGATTG  TTCGGGTGTG  CAATGTCTGA  GTGAACCTGT  ATAAGTGGAG   4119
GCACTTTAGG  GCTGTAAAAT  GCATGATTTT  GTAACCCAGA  TTTTGCTGTA  TATTTGTGAT   4179
AGCACTTTCT  ACAATGTGAA  CTTTATTAAA  TACAAAACTT  CCAGGCTAAA  CATCCAATAT   4239
TTTCTTTAAT  GCTTTTATAT  TTTTTAAAA   TGTTAAAACC  CCTATAGCCA  CCTTTTGGGA   4299
ATGTTTTAAA  TTCTCCAGTT  TTTTGTTATA  TAGGGATCAA  CCAGCTAAGA  AAAGATTTTA   4359
AGTCAAGTTG  AATTGAGGGG  ATTAATATGA  AAACTTATGA  CCTCTTCCTT  TAGGAGGGAG   4419
TTATCTAAAA  GAAATGTCTA  TTAAGGTGAT  ATATTTAAAA  ATATTTTGG   GTGTTCCTGG   4479
CAGTTTAAAA  AAATTGGTTG  GAGAATTTAG  GTTTTTATTA  GTACCATAGT  ACCATTTATA   4539
CAAATTAGAA  AATGTTATTT  AACAGCTGAA  TTATCTATAC  ATATCTTTAT  TAATCACTAT   4599
TGTTCCAGCA  GTTTCAAGT   CAAATTAATA  ATCTTATTAG  GGAGAAAATT  CAATTGTAAA   4659
TTGAATCAGT  ATAAACAAAG  TTACTAGGTA  ACTTCATATT  GCTGAGAGAA  ATATGGAACT   4719
TACATTGTTC  AATTAGAATA  GTGTTCTCCC  CAAATATTTA  TAAAACTTCT  CAAGATACTG   4779
CTACGTGTAA  TTTTATATGA  AGATAAGTGT  ATTTTTCAAT  AAAGCATTTA  TAAATTAAAA   4839
AAAAAAAAAA  AAAA                                                        4853
```

( 2 ) INFORMATION FOR SEQ ID NO:2:

( i ) SEQUENCE CHARACTERISTICS:
        ( A ) LENGTH: 1139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Pro  Ser  Gly  Gly  Asp  Gln  Ser  Pro  Pro  Pro  Pro  Pro  Pro  Pro
 1              5                        10                       15

Ala  Ala  Ala  Ala  Ser  Asp  Glu  Glu  Glu  Asp  Asp  Gly  Glu  Ala  Glu
               20                       25                       30

Asp  Ala  Ala  Pro  Ser  Ala  Glu  Ser  Pro  Thr  Pro  Gln  Ile  Gln  Arg
               35                       40                       45

Phe  Asp  Glu  Leu  Cys  Ser  Arg  Leu  Asn  Met  Asp  Glu  Ala  Ala  Arg  Pro
     50                       55                       60

Glu  Ala  Trp  Asp  Ser  Tyr  Arg  Ser  Met  Ser  Glu  Ser  Tyr  Thr  Leu  Glu
 65                           70                       75                    80

Gly  Asn  Asp  Leu  His  Trp  Leu  Ala  Cys  Ala  Leu  Tyr  Val  Ala  Cys  Arg
                    85                       90                       95

Lys  Ser  Val  Pro  Thr  Val  Ser  Lys  Gly  Thr  Val  Glu  Gly  Asn  Tyr  Val
              100                      105                      110

Ser  Leu  Thr  Arg  Ile  Leu  Lys  Cys  Ser  Glu  Gln  Ser  Leu  Ile  Glu  Phe
              115                      120                      125

Phe  Asn  Lys  Met  Lys  Lys  Trp  Glu  Asp  Met  Ala  Asn  Leu  Pro  Pro  His
     130                      135                      140

Phe  Arg  Glu  Arg  Thr  Glu  Arg  Leu  Glu  Arg  Asn  Phe  Thr  Val  Ser  Ala
```

```
            145                       150                       155                       160
Val  Ile  Phe  Lys  Lys  Tyr  Glu  Pro  Ile  Phe  Gln  Asp  Ile  Phe  Lys  Tyr
                    165                       170                       175

Pro  Gln  Glu  Glu  Gln  Pro  Arg  Gln  Arg  Gly  Arg  Lys  Gln  Arg  Arg
                    180                       185                       190

Gln  Pro  Cys  Thr  Val  Ser  Glu  Ile  Phe  His  Phe  Cys  Trp  Val  Leu  Phe
               195                       200                       205

Ile  Tyr  Ala  Lys  Gly  Asn  Phe  Pro  Met  Ile  Ser  Asp  Asp  Leu  Val  Asn
          210                       215                       220

Ser  Tyr  His  Leu  Leu  Leu  Cys  Ala  Leu  Asp  Leu  Val  Tyr  Gly  Asn  Ala
225                      230                       235                       240

Leu  Gln  Cys  Ser  Asn  Arg  Lys  Glu  Leu  Val  Asn  Pro  Asn  Phe  Lys  Gly
                    245                       250                       255

Leu  Ser  Glu  Asp  Phe  His  Ala  Lys  Asp  Ser  Lys  Pro  Ser  Ser  Asp  Pro
               260                       265                       270

Pro  Cys  Ile  Ile  Glu  Lys  Leu  Cys  Ser  Leu  His  Asp  Gly  Leu  Val  Leu
          275                       280                       285

Glu  Ala  Lys  Gly  Ile  Lys  Glu  His  Phe  Trp  Lys  Pro  Tyr  Ile  Arg  Lys
     290                       295                       300

Leu  Tyr  Glu  Lys  Lys  Leu  Leu  Lys  Gly  Lys  Glu  Glu  Asn  Leu  Thr  Gly
305                      310                       315                       320

Phe  Leu  Glu  Pro  Gly  Asn  Phe  Gly  Glu  Ser  Phe  Lys  Ala  Ile  Asn  Lys
                    325                       330                       335

Ala  Tyr  Glu  Glu  Tyr  Val  Leu  Ser  Val  Gly  Asn  Leu  Asp  Glu  Arg  Ile
               340                       345                       350

Phe  Leu  Gly  Glu  Asp  Ala  Glu  Glu  Ile  Gly  Thr  Leu  Ser  Arg  Cys
               355                       360                       365

Leu  Asn  Ala  Gly  Ser  Gly  Thr  Glu  Thr  Ala  Glu  Arg  Val  Gln  Met  Lys
370                      375                       380

Asn  Ile  Leu  Gln  Gln  His  Phe  Asp  Lys  Ser  Lys  Ala  Leu  Arg  Ile  Ser
385                      390                       395                       400

Thr  Pro  Leu  Thr  Gly  Val  Arg  Tyr  Ile  Lys  Glu  Asn  Ser  Pro  Cys  Val
                    405                       410                       415

Thr  Pro  Val  Ser  Thr  Ala  Thr  His  Ser  Leu  Ser  Arg  Leu  His  Thr  Met
               420                       425                       430

Leu  Thr  Gly  Leu  Arg  Asn  Ala  Pro  Ser  Glu  Lys  Leu  Glu  Gln  Ile  Leu
          435                       440                       445

Arg  Thr  Cys  Ser  Arg  Asp  Pro  Thr  Gln  Ala  Ile  Ala  Asn  Arg  Leu  Lys
     450                       455                       460

Glu  Met  Phe  Glu  Ile  Tyr  Ser  Gln  His  Phe  Gln  Pro  Asp  Glu  Asp  Phe
465                      470                       475                       480

Ser  Asn  Cys  Ala  Lys  Glu  Ile  Ala  Ser  Lys  His  Phe  Arg  Phe  Ala  Glu
               485                       490                       495

Met  Leu  Tyr  Tyr  Lys  Val  Leu  Glu  Ser  Val  Ile  Glu  Gln  Glu  Gln  Lys
               500                       505                       510

Arg  Leu  Gly  Asp  Met  Asp  Leu  Ser  Gly  Ile  Leu  Glu  Gln  Asp  Ala  Phe
          515                       520                       525

His  Arg  Ser  Leu  Leu  Ala  Cys  Cys  Leu  Glu  Val  Val  Thr  Phe  Ser  Tyr
     530                       535                       540

Lys  Pro  Pro  Gly  Asn  Phe  Pro  Phe  Ile  Thr  Glu  Ile  Phe  Asp  Val  Pro
545                      550                       555                       560

Leu  Tyr  His  Phe  Tyr  Lys  Val  Ile  Glu  Val  Phe  Ile  Arg  Ala  Glu  Asp
                    565                       570                       575
```

```
Gly Leu Cys Arg Glu Val Val Lys His Leu Asn Gln Ile Glu Glu Gln
            580                 585                 590

Ile Leu Asp His Leu Ala Trp Lys Pro Glu Ser Pro Leu Trp Glu Lys
            595                 600                 605

Ile Arg Asp Asn Glu Asn Arg Val Pro Thr Cys Glu Val Met Pro
            610                 615                 620

Pro Gln Asn Leu Glu Arg Ala Asp Glu Ile Cys Ile Ala Gly Ser Pro
625                     630                 635                 640

Leu Thr Pro Arg Arg Val Thr Glu Val Arg Ala Asp Thr Gly Gly Leu
                645                 650                 655

Gly Arg Ser Ile Thr Ser Pro Thr Thr Leu Tyr Asp Arg Tyr Ser Ser
                660                 665                 670

Pro Pro Ala Ser Thr Thr Arg Arg Leu Phe Val Glu Asn Asp Ser
            675                 680                 685

Pro Ser Asp Gly Gly Thr Pro Gly Arg Met Pro Pro Gln Pro Leu Val
            690                 695                 700

Asn Ala Val Pro Val Gln Asn Val Ser Gly Glu Thr Val Ser Val Thr
705                 710                 715                 720

Pro Val Pro Gly Gln Thr Leu Val Thr Met Ala Thr Ala Thr Val Thr
                725                 730                 735

Ala Asn Asn Gly Gln Thr Val Thr Ile Pro Val Gln Gly Ile Ala Asn
            740                 745                 750

Glu Asn Gly Gly Ile Thr Phe Phe Pro Val Gln Val Asn Val Gly Gly
            755                 760                 765

Gln Ala Gln Ala Val Thr Gly Ser Ile Gln Pro Leu Ser Ala Gln Ala
            770                 775                 780

Leu Ala Gly Ser Leu Ser Ser Gln Gln Val Thr Gly Thr Thr Leu Gln
785                 790                 795                 800

Val Pro Gly Gln Val Ala Ile Gln Gln Ile Ser Pro Gly Gly Gln Gln
                805                 810                 815

Gln Lys Gln Gly Gln Ser Val Thr Ser Ser Ser Asn Arg Pro Arg Lys
                820                 825                 830

Thr Ser Ser Leu Ser Leu Phe Phe Arg Lys Val Tyr His Leu Ala Ala
            835                 840                 845

Val Arg Leu Arg Asp Leu Cys Ala Lys Leu Asp Ile Ser Asp Glu Leu
850                 855                 860

Arg Lys Lys Ile Trp Thr Cys Phe Glu Phe Ser Ile Ile Gln Cys Pro
865                 870                 875                 880

Glu Leu Met Met Asp Arg His Leu Asp Gln Leu Leu Met Cys Ala Ile
                885                 890                 895

Tyr Val Met Ala Lys Val Thr Lys Glu Asp Lys Ser Phe Gln Asn Ile
                900                 905                 910

Met Arg Cys Tyr Arg Thr Gln Pro Gln Ala Arg Ser Gln Val Tyr Arg
            915                 920                 925

Ser Val Leu Ile Lys Gly Lys Arg Lys Arg Arg Asn Ser Gly Ser Ser
930                 935                 940

Asp Ser Arg Ser His Gln Asn Ser Pro Thr Glu Leu Asn Lys Asp Arg
945                 950                 955                 960

Thr Ser Arg Asp Ser Ser Pro Val Met Arg Ser Ser Ser Thr Leu Pro
                965                 970                 975

Val Pro Gln Pro Ser Ser Ala Pro Pro Thr Pro Thr Arg Leu Thr Gly
            980                 985                 990

Ala Asn Ser Asp Met Glu Glu Glu Glu Arg Gly Asp Leu Ile Gln Phe
            995                 1000                1005
```

```
Tyr  Asn  Asn  Ile  Tyr  Ile  Lys  Gln  Ile  Lys  Thr  Phe  Ala  Met  Lys  Tyr
     1010                1015                     1020

Ser  Gln  Ala  Asn  Met  Asp  Ala  Pro  Pro  Leu  Ser  Pro  Tyr  Pro  Phe  Val
1025                1030                     1035                          1040

Arg  Thr  Gly  Ser  Pro  Arg  Arg  Ile  Gln  Leu  Ser  Gln  Asn  His  Pro  Val
               1045                     1050                          1055

Tyr  Ile  Ser  Pro  His  Lys  Asn  Glu  Thr  Met  Leu  Ser  Pro  Arg  Glu  Lys
               1060                     1065                     1070

Ile  Phe  Tyr  Tyr  Phe  Ser  Asn  Ser  Pro  Ser  Lys  Arg  Leu  Arg  Glu  Ile
          1075                     1080                     1085

Asn  Ser  Met  Ile  Arg  Thr  Gly  Glu  Thr  Pro  Thr  Lys  Lys  Arg  Gly  Ile
     1090                     1095                     1100

Leu  Leu  Glu  Asp  Gly  Ser  Glu  Ser  Pro  Ala  Lys  Arg  Ile  Cys  Pro  Glu
1105                1110                     1115                          1120

Asn  His  Ser  Ala  Leu  Leu  Arg  Arg  Leu  Gln  Asp  Val  Ala  Asn  Asp  Arg
               1125                     1130                          1135

Gly  Ser  His
          1140
```

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: C-terminal ( x i ) SEQUENCE DESCRIPTION: SEQ ID NO:3:

```
Glu  Asn  His  Ser  Ala  Leu  Leu  Arg  Arg  Leu  Gln  Asp  Val  Ala  Asn  Asp
1                   5                        10                          15

Arg  Gly  Ser  His  Cys
               20
```

( 2 ) INFORMATION FOR SEQ ID NO:4:

( i ) SEQUENCE CHARACTERISTICS:
        ( A ) LENGTH: 561 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 312..551

( x i ) SEQUENCE DESCRIPTION: SEQ ID NO:4:

```
CAGCCCTGTT  GAATGTTCTC  ACGGTGGGGA  GGTACGTGTT  TAAAATACGG  GGAAGGTGCT        60

TTTATTTCAC  CCCTGGTGAA  ACTAGGGGAG  CTAATTTTTT  TAAACATGAT  TTTTGTCCCC       120

CTTGAACCGC  CGGCCTGGAC  TACGTTTCCC  AGCAGCCCGT  GCTCAAGACT  ACGGGTGCCT       180

GCAGGCGGTC  AGCGTCGTTT  GCGACGGCGC  AGACGCGGTG  CGGGCGGCGG  ACGGGCGGGC       240

GCTTCGCCGT  TTGAATTGCT  GCGGGCCCGG  GCCCTCACCT  CACCTGAGGT  CCGGCCGCCC       300

AGGGGTGCGC T ATG CCG TCG GGA GGT GAC CAG TCG CCA CCG CCC CCG CCT          350
            Met Pro Ser Gly Gly Asp Gln Ser Pro Pro Pro Pro Pro
              1               5                        10
```

| | | | | | | | | | | | | | | | |
|---|---|---|---|---|---|---|---|---|---|---|---|---|---|---|---|
| CCC | CCT | CCG | GCG | GCG | GCA | GCC | TCG | GAT | GAG | GAG | GAG | GAG | GAC | GAC | GGC | 398 |
| Pro | Pro | Pro | Ala | Ala | Ala | Ala | Ser | Asp | Glu | Glu | Glu | Glu | Asp | Asp | Gly |
| | 15 | | | | 20 | | | | | 25 | | | | 30 | |

| GAG | GCG | GAA | GAC | GCC | GCG | CCG | TCT | GCC | GAG | TCG | CCC | ACC | CCT | CAG | ATC | 446 |
|---|---|---|---|---|---|---|---|---|---|---|---|---|---|---|---|---|
| Glu | Ala | Glu | Asp | Ala | Ala | Pro | Ser | Ala | Glu | Ser | Pro | Thr | Pro | Gln | Ile |
| 30 | | | | | 35 | | | | | 40 | | | | | 45 |

| CAG | CAG | CGG | TTC | GAC | GAG | CTG | TGC | AGC | CGC | CTC | AAC | ATG | GAC | GAG | GCG | 494 |
|---|---|---|---|---|---|---|---|---|---|---|---|---|---|---|---|---|
| Gln | Gln | Arg | Phe | Asp | Glu | Leu | Cys | Ser | Arg | Leu | Asn | Met | Asp | Glu | Ala |
| | | | | 50 | | | | | 55 | | | | | 60 | |

| GCG | CGG | CCC | GAG | GCC | TGG | GAC | AGC | TAC | CGC | AGC | ATG | AGC | GAA | AGC | TAC | 542 |
|---|---|---|---|---|---|---|---|---|---|---|---|---|---|---|---|---|
| Ala | Arg | Pro | Glu | Ala | Trp | Asp | Ser | Tyr | Arg | Ser | Met | Ser | Glu | Ser | Tyr |
| | | | 65 | | | | | 70 | | | | | 75 | | |

| ACG | CTG | GAG | GTGCGCTCGC | | | | | | | | | | | | | 561 |
|---|---|---|---|---|---|---|---|---|---|---|---|---|---|---|---|---|
| Thr | Leu | Glu | | | | | | | | | | | | | |
| | | 80 | | | | | | | | | | | | | |

( 2 ) INFORMATION FOR SEQ ID NO:5:

( i ) SEQUENCE CHARACTERISTICS:
        ( A ) LENGTH: 80 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Pro | Ser | Gly | Gly | Asp | Gln | Ser | Pro | Pro | Pro | Pro | Pro | Pro | Pro | Pro |
|---|---|---|---|---|---|---|---|---|---|---|---|---|---|---|---|
| 1 | | | | 5 | | | | | 10 | | | | | 15 | |

| Ala | Ala | Ala | Ala | Ser | Asp | Glu | Glu | Glu | Asp | Asp | Gly | Glu | Ala | Glu |
|---|---|---|---|---|---|---|---|---|---|---|---|---|---|---|
| | | | 20 | | | | | 25 | | | | | 30 | |

| Asp | Ala | Ala | Pro | Ser | Ala | Glu | Ser | Pro | Thr | Pro | Gln | Ile | Gln | Gln | Arg |
|---|---|---|---|---|---|---|---|---|---|---|---|---|---|---|---|
| | | 35 | | | | | 40 | | | | | 45 | | | |

| Phe | Asp | Glu | Leu | Cys | Ser | Arg | Leu | Asn | Met | Asp | Glu | Ala | Ala | Arg | Pro |
|---|---|---|---|---|---|---|---|---|---|---|---|---|---|---|---|
| | 50 | | | | | 55 | | | | | 60 | | | | |

| Glu | Ala | Trp | Asp | Ser | Tyr | Arg | Ser | Met | Ser | Glu | Ser | Tyr | Thr | Leu | Glu |
|---|---|---|---|---|---|---|---|---|---|---|---|---|---|---|---|
| 65 | | | | | 70 | | | | | 75 | | | | | 80 |

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

ACGCTGGAGG TGCGCTCGC           19

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

TCTTTTACAG GGAAATGAT           19

( 2 ) INFORMATION FOR SEQ ID NO:8:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:8:

AGAGCAGAGG TAACTATGT                                               19

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

TTAATACCAG CTTAATCGA                                               19

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

GAAACAGCGG TAGGTTTTC                                               19

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

TCCCCCAAAG GCGACAGCC                                               19

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

ATGCAAAAGG TAAGAAAAT                                               19

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear (  i  i  ) MOLECULE TYPE: DNA (genomic)

( x i ) SEQUENCE DESCRIPTION: SEQ ID NO:13:

AATCCTGCAG    GTAATTTCC                    19

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

ATTTTAAAGG    TAGGTTTGT                    19

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

ACACCATAGG    CTTATCTG                     18

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

GAAAAAAGG    TTTGTAAGT                     19

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

TTCATCATAG    CTCCTTAAG                    19

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

AGAGAGTTTG TGAGTACTT 19

( 2 ) INFORMATION FOR SEQ ID NO:19:

( i ) SEQUENCE CHARACTERISTICS:
    ( A ) LENGTH: 18 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:19:

TTCCTATAGT AAAGCCAT 18

( 2 ) INFORMATION FOR SEQ ID NO:20:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:20:

TTTGACAAGG TGAGTTTAG 19

( 2 ) INFORMATION FOR SEQ ID NO:21:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:21:

TTTTCTTTAG TCCAAAGCA 19

( 2 ) INFORMATION FOR SEQ ID NO:22:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:22:

GATTCTCAGG TTAGTTTGA 19

( 2 ) INFORMATION FOR SEQ ID NO:23:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:23:

CCTTTTTTAG GACATGTTC 19

( 2 ) INFORMATION FOR SEQ ID NO:24:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:24:

GTGCTAAAGG TAATTGTGC     19

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

ATTTCTACAG AAATTGCCA     19

( 2 ) INFORMATION FOR SEQ ID NO:26:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

GATTTATCTG TGAGTAAAA     19

( 2 ) INFORMATION FOR SEQ ID NO:27:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

ATTTTATAGG GTATTCTG     18

( 2 ) INFORMATION FOR SEQ ID NO:28:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

TTTTATAAGG TATTTCCCA     19

( 2 ) INFORMATION FOR SEQ ID NO:29:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear (  i i ) MOLECULE TYPE: DNA (genomic)

( x i ) SEQUENCE DESCRIPTION: SEQ ID NO:29:

TTTATTTCAG GTGATAGAA 19

( 2 ) INFORMATION FOR SEQ ID NO:30:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:30:

TGTGAAGAGG TGAAAATCA 19

( 2 ) INFORMATION FOR SEQ ID NO:31:

( i ) SEQUENCE CHARACTERISTICS:
  ( A ) LENGTH: 18 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:31:

TCTTCATAGG TCATGCCA 18

( 2 ) INFORMATION FOR SEQ ID NO:32:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:32:

TTGGAAGGAG TAAGTTTAA 19

( 2 ) INFORMATION FOR SEQ ID NO:33:

( i ) SEQUENCE CHARACTERISTICS:
  ( A ) LENGTH: 20 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:33:

TTGACCCCTA GGCATAACAT 20

( 2 ) INFORMATION FOR SEQ ID NO:34:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:34:

CTGTGCAAGG TAAGGAAGG                                        19

( 2 ) INFORMATION FOR SEQ ID NO:35:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:35:

CTGTCACTAG GTATTGCCA                                        19

( 2 ) INFORMATION FOR SEQ ID NO:36:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:36:

TTTAGAAAGG TAATTTTTC                                        19

( 2 ) INFORMATION FOR SEQ ID NO:37:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:37:

TATCTCCTAG GTATACCAT                                        19

( 2 ) INFORMATION FOR SEQ ID NO:38:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:38:

ATGGCAAAGG TGAGTACCA                                        19

( 2 ) INFORMATION FOR SEQ ID NO:39:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:39:

GTTTGCCAGG TCACAAAA                                         18

( 2 ) INFORMATION FOR SEQ ID NO:40:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:40:

CGGAGCCAGG TAACTACAT                                              19

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:41:

TTCTCTAAAG GTGTATAGA                                              19

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:42:

AAGATAGAAG TGGGATCTT                                              19

( 2 ) INFORMATION FOR SEQ ID NO:43:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:43:

CTGGCTGCAG CCAGTAGAG                                              19

( 2 ) INFORMATION FOR SEQ ID NO:44:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:44:

CAGGCAAATG TAAGTATGA                                              19

( 2 ) INFORMATION FOR SEQ ID NO:45:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear (i i) MOLECULE TYPE: DNA (genomic)

(x i) SEQUENCE DESCRIPTION: SEQ ID NO:45:

TTTTTAAACA GATGGGATGC 20

(2) INFORMATION FOR SEQ ID NO:46:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:46:

CCTTCAAAGG TGAGCCTAA 19

(2) INFORMATION FOR SEQ ID NO:47:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:47:

CCCACCATAG AGACTGAGA 19

(2) INFORMATION FOR SEQ ID NO:48:

(i) SEQUENCE CHARACTERISTICS:
        (A) LENGTH: 3865 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:48:

```
GTAGGTTTTC TTGTTGGTTC ATCAGGAATA CACATTAGTC TGTGCTGCAG TGTTGATATT    60
CTGCTAGGTT TTTTTTTTCT GGTTTTAAAA AAGAAATAAG ATTTAAAAAA TCTTTTTCCT   120
CAGTCGTTTT CTTTTAATGA TGCTTCCGGG GCTTCACATT GTGGGTTAGC CATGAAGAGT   180
GGCTTTCACA TATTGCTAAA TGTATACAGG TCTGTGTTTC TATAAACTAC ATGTGTCTTA   240
TTTCATTTTA TTATTATTA CCTCCTCAGT GATCCTTGTT CTGAAACCTT CCTTTTTCAT   300
TTAAGCAACA AAAATGCAG ACTGTACAAG TCAGACTTAG GGATTTTCAC CCTTTCGCCG   360
CCTTGGAGAG TTCTGTATCT GTATCTGGAT ATATATATTT TTTATTGCGC AGGGGCCATG   420
CTAATCAATG TATTGTTCCA ATTTTAGTAT ATGTGCTGCC GAAGGGAGCA CTGCCCTAGA   480
TATAGATCAC TATATTAACC ACTATATTTT CTACTAGTGA TTATATAGAC TATTTTATGT   540
CAAACTGAGT AATAAATAAT CCCCTTGAAA TGACTTCTCT ATGTATTTTG ATGTTTATAA   600
TGAATTCAGA ATAGAGAGAC TGGATTGGGA AAAGACAGGA GAACTGAAAC TATTATGAAT   660
TTGTGCTTTC TGATCACTTC TGCAAAGTCT ATAAGCATGC TCTGACTCAG TGTTTTCTAC   720
CTTCCTGAT AGATAAAGGC AGTTATGGAA TACACATTTT CCTTCTTTAT CATTGAAAGT   780
TTTTTCATAA AGTAGAAATG AAAATTCTAA CAATTAAAAA AATGTTGACA AGAAAAGTAA   840
AGGGAAAGGA GTTAAAATTA TTTGGCTAGA ATAAATAATG TTTGCTTCTC TTTAAATATA   900
```

| | | | | | | |
|---|---|---|---|---|---|---|
| AAAGTTTTCC | CAGACTGTGA | AGGATGTTTA | CATTAAGTGT | AACCTTTTAA | AAATAAAATG | 960 |
| GAATGACAAA | CCAGGAGGAA | AAAAAATTTA | AAAAAACTAG | AACTATTTAC | ATTTTAATAT | 1020 |
| AGATGGCACC | ACTGATACAG | AAGCATCTGG | TCTAGCTCAC | TTACAGTTTT | GGGGAATTGA | 1080 |
| CTATTTAAAA | TGAAGCATTC | TGAGCCAGGC | GGGTTGGCTC | ACGCCTGTAA | TCCCAGCACT | 1140 |
| TTTATGAGGC | TGAGGCAGGC | GAATCACCTG | AGTTCAGGAG | TTCAATACCA | GCCTGGCAA | 1200 |
| CGTGGCAAAA | CCCCGTCTCT | ACTAAAAATA | CAAAAATTAG | CTGTGCATGG | TGGTGCATGC | 1260 |
| CTATAATCCC | AGCTACTCGG | GAGGCTGAGT | CAGTTGAATC | CCTTGAACCG | AGAAGCAGAG | 1320 |
| GTTGTGAGCC | AAGATCGTAC | CATTGCATTC | GAGCCTGGGC | GACAGAATGA | AACTCCATCT | 1380 |
| CATAAATAAA | TAAATAAACT | AATAAAATGA | CATATTCTCC | TAGCACTTTG | GGAGGCCGAG | 1440 |
| GCAGGTGGAT | TGCTGGAGGT | CAGGAGTTCA | AGACTAGCTT | GGCCAATGTG | CCAAAACCCC | 1500 |
| ATTTCCATTA | AAAATACAAA | AATTAGGCAG | GTATGGTGGT | GTGTGCCTGT | TGTCCCAGTT | 1560 |
| ACTTGAGGGC | TGAGGCAGGT | GAATCACTTG | AACCCAGGAG | TCGGAGGTTT | CAGTGAGCTG | 1620 |
| CGATCGCGCC | AATGCACTCC | AGCTTAGGTG | ACAGAGTGAG | ACTTCGTCTC | CAAATAAATA | 1680 |
| AATAAAAAAT | GAAGTATTCT | AAAGGTTTGA | ATAGAAGCTT | TGTACTGAGT | CTGAGTGAGG | 1740 |
| CCAATGTGAT | CATTTATGGG | AAGATATCTT | CTTTGTTTGG | AGTATCTGGA | AAATAATTTC | 1800 |
| AGATTGCACT | TGTTTTGCTA | TTTCTTAGGA | TATATATACT | ACCTAATTCT | AATTAAGAGA | 1860 |
| ATTTTAAAAG | GCCATGTGCA | GTGGCTCACA | CCTGATCCCC | AGCACTTTGG | GAGGCTGAAG | 1920 |
| TGGACAGATC | ACTTGAGCCC | AGGAGTTTGA | GACCAGCCTG | GACAGTATGG | CGAAACTTCA | 1980 |
| TCTCCACAAA | AAATACAAAA | ATTAGCTTGG | AGTGGTGGCG | CACACCTGTG | GTCCCAGCTA | 2040 |
| CTGGGGAGGC | TGGAGGTGGG | GGGATCACTT | GAGCCTGGGA | GGTTGAGGCT | GCAGTGAGCT | 2100 |
| GTGCTCATAC | CACTGTACTC | CAGTTTGGGT | GACAGAGCAA | GACCTTGTTT | CAAAAAAAAA | 2160 |
| AAAAAAAGT | AAATCACTTT | ATTAGAGATT | TTACATTTTA | ATCACTTTGT | ATACTTTCTG | 2220 |
| TTAGCTCTTT | CTGTTAACTA | TAGTCATAAT | GTATAGCACT | TACTGAGCAT | TTACTTTGGG | 2280 |
| GCAGGGACTC | TTAAGACTTC | AATATGTATT | ACTTCAGTTA | ATCCCTCTGA | CAACCTTGTG | 2340 |
| ATACTCATAC | TATTGTTAGA | TAGAGAAAAT | TAACCGCAGA | GAGGTTAAGT | AATTTGGCCA | 2400 |
| GGGTCGCACA | ACCAAGCGTG | GAGTTCTTAT | TGAAACTGAC | TGCGGGAACC | CATGTGCTTT | 2460 |
| ACTGTGACTA | TATACTGCAT | CTCTCACACA | CTATCTGAAA | ATGTGTCACT | ATTTGTTTAG | 2520 |
| CACTTATCCA | CAGGAAATAC | TGTCAGGTAT | TATGTAGGAC | ACAAGCATTT | TTTAAAACAC | 2580 |
| CAAACCCCAC | AGTTTTTGTT | TTCTGAGAGC | TTACAGTACA | GTCAGCGAGA | TGAGGCAGGT | 2640 |
| ATGAAGATTC | CAGTGCATGC | AATGCAGTGT | GTTATAAAAG | TCCCATGACT | ACCAGAGGGA | 2700 |
| ATACAGATGT | AAAACTTAGG | AGGAAAAGAA | ATCACTCTGG | ATGAGCCAGT | CAGGTAAGTT | 2760 |
| TACATGGAAT | AAGTAGAAAT | GGGTCTTGAA | AGATGGGTAC | GAGTTTGATA | GGTGAATTTG | 2820 |
| AAGATACAGA | TAGCACCTTC | TGTGTAGAGG | AAACAAGAAA | AGACAAAAGC | AGTAAAGCAA | 2880 |
| GAAGAAATGT | GGGAGGTTAG | TCAAGTTTTT | TTTTCTAGAA | TTCTCAAGTT | GTAGAGCCAG | 2940 |
| AATTAAGAGT | AGCTTAAGTG | TTAAGCTAAA | AAAAATTGAA | TTTTATTTTG | GTAGGCAACT | 3000 |
| AAAACTAGAA | ATAGTTTATC | ATGCGCCTAT | GGTAGAGAGG | ATACTTTTAA | AAGCAGAACA | 3060 |
| CTGACATTTA | ATCCTTGCCA | TGGAGTGGTG | AACTAAGTAC | AGTATTGTAC | CCAAGTAGAG | 3120 |
| TAATCTTTTG | ACAGATGAAA | TGACTAAGGC | CCAGGTGAGC | AAGTGTACCC | TAGCTAATGG | 3180 |
| CAGTGCTGGA | ACTAAATCTA | ATCTAATCTT | CTCCACGGAA | TTTCGTTCTT | CTGGGCACCT | 3240 |
| TGTTAGAATA | AGGCTGTTGG | GAGGTGGAGA | CCACAGATTT | CTTGTCTAAA | AGTTGTCAGA | 3300 |

```
GGTTTTGGTA  GAAAAGCCAA  GCTTAAAGCA  GGTCTGAAAC  TTGGCAGACT  ACTTGGCAAT    3360

ATACAACAGG  TACTCTTAAT  GGATGGAAGT  ATAAGGAATT  ATAGGAAGCT  CATAATTTAC    3420

ATTAAAAGG   CCTTTTGTGA  TTTGATATAG  TCTGGAATAT  CTTTAAGGAG  GGAGGGAGGG    3480

ATACAGGTCA  TTAGCTATGA  TAAAGGAGAA  AAAAATAAGG  ACATATCTGA  CTGCATATAG    3540

TGGTCCTGAA  TCAGCATAGC  ATTGCTGTGT  CATCGAAAGA  ACTATTTTTA  TTCATTTTAT    3600

TTTCCACCTC  ACCTATCTTG  CCTTCACAAA  ACTTTAAAAG  ATTCTTTAAG  AATTTTCTTT    3660

TCTTTGAGAT  GGGCTCTTTC  CCTGGTACCC  AGCTATTTCC  TACCAATATT  TTGTTAAGGC    3720

AGAACGTCCA  CGTTTTCCAT  GTGAAGCTGA  ATCTGTTGTC  TCTCCCTTTA  ACTGTGGGTT    3780

TTATTTTACA  CCTGATTTAT  AATCATTTGG  GATTTTTTTT  TCTGATCTTC  TGGTGTCTCG    3840

TGACTGGGGT  TTTCTTCCCC  CAAAG                                              3865
```

( 2 ) INFORMATION FOR SEQ ID NO:49:

( i ) SEQUENCE CHARACTERISTICS:
        ( A ) LENGTH: 4576 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:49:

```
GTAAGAAAAT  AGTAATATTT  ATTTAGATTT  AATATGTCTA  TTTACATTAC  CAGGTATTAA      60

TCTCGTCAAC  TCCTAATATG  TATCAGGAAA  AGATTTCCAC  TGAAAATTTT  CTCAAGGGTT     120

TTAATCCTAG  ATTCTTTTTT  AAGTATTGCC  TTTCCATCAA  AGGATCTATT  GGATTTCTTT     180

ACAATATCCA  AATCTCTCTT  ATTAAATGGA  AAGTCCATTA  ACTTCGTTGT  ATACAACATC     240

TTTCCTACCC  AAAGCTACTC  TCCTCAAATT  ATGAGCTGAA  AACACATAAT  CCTGTATATG     300

CTTGTATTGC  GAACTCTATC  TTCCATGAGA  TGTATCTTAT  TTAGTCTGAG  CGCAATTACT     360

GATCAACCTC  AGAGCTGTTC  AGATTTTTTT  GTGTGTCTTG  TTCACATAAG  TATACTTAGT     420

CAAATGCTTT  TATATACTAT  TTATTTTCTT  TCCCTTTTTT  CTTGTCTCAT  TTAACCTACC     480

CAAGGTCTGC  ATTCAGTGAA  ATACATGTCT  CTATTATTTT  TTGTCCTTTT  TGTATTTATT     540

TATTTATTTA  TTTATTTGAG  ATGGAATCTC  ATTCTGTCTC  CCAGGGCTAG  ATTGTAGTGG     600

CACAATCTCG  GCTCACTGCA  GGCTACACCT  CCCAGGTTCA  AGTAATTCTC  CTGCCTCAGC     660

CTCCCGAATA  GCCGTGATTA  CAGGCGCCCA  CCACCATGCC  CAGCTAATTT  TTGTGTTTTC     720

AGTAGAGATG  GGGTTTCACC  ATGTTGGCCA  GGCTGGTCTC  AAACTCCTGA  CCTCAGGTGA     780

TCTGCCTGCC  CTGGCCTCCC  ACAGTGCTGG  GATTATAGGC  ACGAGCCACT  GCGTCCAGCA     840

CCTTAGTATC  TTTCTATGTA  GAACGAATGC  TCCCAGGTAG  ATGGGAAAGT  GCAGATATAT     900

TATTATGTAG  TCAGCTCCTG  TATACCATGT  GGCTTGGCCT  TCGTCACTAA  GATGGCTCAC     960

TCTGAATGCA  AAGTTATCAC  AGAGTCTTAG  GTGCTGGAAG  GAGTTGCACA  GGTATCACTG    1020

AGACTCTCAT  TATTAGATTA  ACTAGCTTAA  CTTACTTTAT  TTTTTTTGA   GATGGAGTCT    1080

CACTCTGTTG  CCCAGGCTGG  AGTGCAGTGG  TGCGATCTCG  GCCCACTGCA  ACCTCTGCTG    1140

CCCGGGTTCA  AGCGATCTCC  TGCCTCAGCC  TCCCGAGTAG  CTGGGATTAC  AGGTGCCTGC    1200

CACTGTGCCC  GGCTAATTTT  TTGTCGTTTT  AGTAGACACG  GAGTTTCACC  ATCTTGGCCA    1260

GGCTGGCCTT  GAACTCCTGA  CCTCGTGATC  CACCTGCGTC  AGCCTCCCAA  AGTGCTGGGC    1320

TTACAGGCGT  GAGCCATCGC  ACCCAGCCTA  GCTTAACTCA  GTTACTTTAT  TTTCTATTTT    1380

TATTTTTATT  TTTGACACAG  GATCTTGCTC  TGTTGCCCAG  GCTGGAGTGC  AGTGGTATGA    1440
```

-continued

```
TCTCTGCTCA CTGCAACCTC CGCCTCTTGT GTTCAAGTTG ATTCTTGTGG CTCAGCCTCT    1500
TGAGTAGCTG GGATTGCAGG CATGCACCAT TATACCTGGC TAATTTTTGT ATTTTTAGTA    1560
GTGTTGGGGT TTTGCCATGT TGGCCAGGGT GGTCTCGAAC TCCTGACCTC AAGTGATCTG    1620
CCACCTCGGC CTCCCAAAGT GTTGGGATTA CAGGTGTTGA GCCACCATGC TCAATCAGCT    1680
TAGTTACTTT AAAGATTAGG CAGCTGAGCC CAGAAACTAG CTGCTGGGAA CAAAGCTAAG    1740
ATTGAACTCA GATCTCCTGG TTCCTGGTTC TTAGTTTCAT ACTGGCTGTG AAGGCCTCTG    1800
GGAAGAATGT GTTACATTGT TGGTCTCCAG GTTTGATTTG TCCTGGTCCC TCTCTGGCTA    1860
ATTAGGGTGA GAGCCGCCAT CCTTCCTTCC CTGAGCTGCA TGCTTGATTC AAGAGAAAAA    1920
TCTTTCTTTT GTCATACATG ACACTGGCAT GTTTCTTTAA TGATGATAAA GGCGACATGA    1980
TCAGTGGCAT GAAATAAAGG TTTTGGAGTA TATAAACCAT TTTTACAGCG CTACAAATT     2040
TTAGAATGTG TGACTGCTAT TATGTATGAT GGTAATCTTT TCATATGATT GTATTGGGCA    2100
AGTATGTCTC ATTTCTAGGG TTTTTATCTG TTTTGTTTGT CTTTTATGGC ATATGTGTAC    2160
TTAGAAGTAA ATATAGTTGG TACTATATAT AATATGTACA ATACAATAAA AATAATTTC    2220
ATTGTCCTTA TTTTGTTCTC ACTGGACCTG TTGGGGTGGT TTTTTCTCTG TAATTAACTC    2280
AGTGTTTGAC TTTTATCTCA TTAATTCAGT TTATAATAAT TCCACCTTAA GAACCTTTGT    2340
GGATTGGGCA TGTTGGCGTA TGCCTGGAAC CTAGCTACTT GGGAAGTTGA AGTGGGAAGC    2400
GGAGGCTGCA GTGAGCTGAG ATTGCACCTC CAGTTTGGGC GAATTTGAGA CCGTGTTTCG    2460
AAAAAAAAAA AAAAAAAAA AGAAACTTGG TCCTTTCACA GTCCACCACT GTGATCTTTT     2520
ATAATACACG ATGATCTTTT TCTAATAGTC ATTTAATTGC TTTAATTCAG TTCTCATTTA    2580
TTTGGGGGAA AGGTGTACTC TTTTATAGCC ACCTTTCTAA TGACAAATAA GCCAACTCTG    2640
GAGATGAAAC ATTTCTATTT ACTTGTTATC TTTGTTGATT AAAAGATAAA ATACCTCACA    2700
AAGTCAGATT TATTTGTAAG GTCAGGATTT GAAATAGAAA ATACGTCATG TTGAGAGAGT    2760
CCTAGAATTT AATTTAAATT AGATTCTGAT CTTTAGGGGC ATTTCAGCTT TTTATTAGAT    2820
GTTACGAGTA CTGTTTTTTT TTTTTTTTTT TTTGCCTTCT ATGGCAAGTG CACACCAGTA    2880
ACAAGTTTAG GCTTGTTGGT GTGATGGGCT TTGTAGCTTG AAATCAGTAG GTGCTACTTA    2940
CTTACTTTTT TACACATGAG GAACCAAGTA TATTTAATA TTAAACCTCT TTATAGGAGA    3000
GCCAAGCAAG TTGGTTTGGC TGTATCAATG CGCAGTTTGA TGTGGTGATT ATCGTTTGCC    3060
TGCTTTGGCA GAGGAGGATT TTTTTTTCTC TTTAGTTCAT TTAAGTTGAT TTGTTGAATG    3120
TTTCCATCTA AACAAAAAAG AATTGCTTTG TATACGCTGA GGTAAGTGGT AACTTTCTTT    3180
GGAGGAACAG AGAGAAAGGG AAACCTGAAA CAAAACTGCA GGTGTGTGTG TGTGTGTACA    3240
TGTACACTTG GGTAGGCGTT AAGTGTGAAA TGCTGAGGTT TGGAAATAAT TCTTCATATG    3300
TATGTTAGCT TATTTAAATT GAATTTATCT GATGATACAA GAATGTAAAA TCACCATGAA    3360
GCATACATGT GCAGTGTTTA ACTAAAAAAG GATGGGCTTG AAGTTATAAA ATAACTAGAA    3420
ATAATTCTTA ATTTCTAGAA AATTAAGATA ATAATAAAAT GGTTTAACTA CACGTAAAAA    3480
TGTGTTCAGT GTTAGAGTTC AACCAGCACT GCAGAAAATT ACATGTTTCT GTCAGTTTAG    3540
GTTTTTGATT TCTTATTTCC CTGTTACCAA GCATCAGCAA TTATTCTTGG GATTATTAGC    3600
CCTGGAATTG AAAGATATTT AATGGTACTC CTGTTGCATT AATTTGTCTG AGTTTATGTA    3660
GAAAGTATT AAAAATGTTA CTGTTGGAGT CTGATAAAAA GTTCTGGTCT TTTAAAAATA    3720
TGTGTATGAG AAATAGCATG AACTCAGGAG GCAGAGCTTG CAGTGAGCTG AGATCGTGCC    3780
ACTGCACTCC AGCCTGGGCG ACAGTGAGAC TCCATCTCAA AAAAAAAAA TGTATATGAG     3840
```

| | | | | | | |
|---|---|---|---|---|---|---|
| AATAATTAAG | TGAATTATTT | TTTCGGCTGT | CTCCTAAGTA | TTTCTAATAA | TTTTCATGAC | 3900 |
| AGAAAAATGT | TTTCATGCAA | AACAATTTCC | TTACAGTTTG | AGATAATTTA | TAAATGTTTT | 3960 |
| GTGTTCAGAA | TTTTCAAAGA | AAAGACCAAT | GATAAAGTTT | TATTCAGCTA | CTAGGTATTT | 4020 |
| AATAAACACT | TAATGATGAA | TGGCATTTTT | AGTAAAGTTA | TAGTTTTCAC | TAAGCTGTTA | 4080 |
| GACATTTATT | AATTTATTAA | AGGCCAGGCA | TGGTGGTTTA | CACCTGTAAT | CCTAGCACTT | 4140 |
| TGGGAGGCCA | AGGCAGAAGG | ATCACTTGAG | TCCAGGAGTT | CAAGACCAGC | CTGGGCAACA | 4200 |
| TAGCAAGACT | CCATCTCTAA | AAAAGTTTT | TAAATTAGCC | ATGTGTGGTG | GCGTGTACCT | 4260 |
| GTAATTTGCA | GCTGCCCAGG | AGGCTGAGAC | AGGAAGCCCT | TGAGCCCAAG | AGGTTGAGGG | 4320 |
| TGCAGTGAGC | CATGATCATA | CCACTGTACT | CCAGCCTGGG | TGACCCACCA | AGACTCTGTC | 4380 |
| TCTTGAAATA | AATAAATAAA | GAAATTTATT | AAGATATTAG | AGTAATATGT | CGGATGTAAA | 4440 |
| TTTGCCAAAA | CACTTATTGT | AATGAGTCAA | TTTTGTACAA | TTGTTTTGTA | ATGTCATAAT | 4500 |
| AAGAAAGGAA | GAAATTTTTT | AAAAATGTTA | CAAAGTCAAT | GCTAATTTAA | CTCTGTAACT | 4560 |
| GCTTATAATC | CTGCAG | | | | | 4576 |

( 2 ) INFORMATION FOR SEQ ID NO:50:

( i ) SEQUENCE CHARACTERISTICS:
        ( A ) LENGTH: 1618 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:50:

| | | | | | | |
|---|---|---|---|---|---|---|
| GTAGGTTTGT | AAATCAAAGA | TTTTTGGGCA | ATCTGCGTTT | CTGTGTTATG | TTTACCCTTG | 60 |
| GAGTTGTACA | GGTTTCCTAG | CATCAGTATT | TTGAAGAGCT | CCTGTCATTA | CGGCTATCCA | 120 |
| GGGTACTTAT | AACTAAGAGT | CAAGCTGCCT | GTAAAAATAT | TTTTGGATAA | ACAGTTGCAG | 180 |
| ATACCACAAA | GTTTAAAGTC | TTAAATGACA | ACTTCAAGAA | GTTTCTGAAA | TATATACTCA | 240 |
| ACAAGGAGAA | GGCATTTAGA | AACTCAGAGT | TGCGAAGATG | ACATTAAAGC | CGATAATGTT | 300 |
| TCCTACATTG | GCAAACTTTG | TGCCTGACAC | ATTGTAGGAG | ATCAAAAGA | ATTTGTTGAA | 360 |
| AGAATCTTAC | TTCAAATTTT | GGTACAGAAG | AATAGTTATG | GTTCTAAAAT | AAAGAAAATG | 420 |
| AACTTTCATC | TTTTAAACTA | ACAGATATAT | GGAAATGATG | ATTTTGGCAT | TGCATTTAAT | 480 |
| AGAACTTAGG | TATATAATTT | CTATGAATGA | TAAACAGTTA | CAAGCCCAAA | TTATGATTTA | 540 |
| CAAAGCAAAT | ATTAAAAAGT | ATGTATAGAG | TTAAATAAA | TATTGCTGCT | GCTATTTGAG | 600 |
| TAATATTGTA | ATAGGATTCT | GGGTGATTCT | CAGTTTGGAG | GTAATTTCAG | TTAAAATTTC | 660 |
| AGCTTGTCTA | TCAAGGTAGA | TTTTTAAAAT | TAGTGGAGTT | CAGTTGCTCC | TGGTATGGTA | 720 |
| AATTTAATGT | TCCTCATCTT | CTTTTCTGTT | CTTTCTCTCA | TTTCTATCAT | AACTCCCTTG | 780 |
| TATATTCCCA | AAAAGCTGCT | TCCTTTCACT | TTTATCTTTT | TTTGGTTTTA | AATTAAAAG | 840 |
| AATTTTTTTT | TTGGAGACAG | GGTCTCACTC | TGTCACCCAG | GTTGGGATGC | AGTGGTGAAA | 900 |
| TCACAATTCA | CTGCAGCCTC | AATCTCCTGG | GCTCAGATGA | TCCTCTCATC | TCAGCCTCCC | 960 |
| AGGTAGCTGG | GACTACAGAC | ATACACCACC | ACACCCAGTT | AATTTTTTTG | TATTTTTCAG | 1020 |
| TATAGATGAG | GTTTCACCAT | GTTTCCTGGG | TTGTCTCAAA | CTCCTGGACT | CAAGCGATGT | 1080 |
| ACCCACCTTG | GCCTCCCAAA | GTGGATTATA | GGAATGGAGC | CACTATGCCC | AACCTTTACC | 1140 |
| TCTTTTATTT | TTAGTTGATT | TTTTTCTTT | TGTGCTGAGT | CTAGGGCAAG | AATAAATTGT | 1200 |

| AAACTAGTAT | GAAATACATC | TAATACATTC | AAATTAAAGA | TATAAATATC | TGAACAGTGT | 1260 |
| AATTTTTTAA | AGTGGTGTTT | TTTGTTTAAA | AGTAGACTTA | CTTGCAAAGT | TGTATTTTGT | 1320 |
| GGTTTTTAGA | TCTTAGTATC | CTAAAATTTG | ATTACCTAAA | ATTTAAGTTT | TAAGTTTCCC | 1380 |
| TTAACCATCT | CTACATAAAT | AATTGAATAA | CTGAAATCTT | TCGAGTAATG | ATACACTTTA | 1440 |
| CTTCTATTTG | CCATTTTTTG | ACAAATTCTT | AGTGTTGAAA | TAGGCCCATA | TATACTGTTT | 1500 |
| CCTATACATT | TGTATGCTAA | GTGGTATACT | GATTATACTC | TATGTTTTAC | ATTTAGTTT | 1560 |
| ATTACAAATT | GGCTTATTGT | GTGCTGATAT | CTCTGTTTTG | TGATTCTATA | CACCATAG | 1618 |

( 2 ) INFORMATION FOR SEQ ID NO:51:

( i ) SEQUENCE CHARACTERISTICS:
        ( A ) LENGTH: 92 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:51:

| GTTTGTAAGT | AGCAAAGAAA | TAACGTGAAA | ATGTTTTCTG | GAGAAAAACT | TGATTTAACA | 60 |
| TGACGACTTA | AGGATCTCTT | CTTTCATCAT | AG | | | 92 |

( 2 ) INFORMATION FOR SEQ ID NO:52:

( i ) SEQUENCE CHARACTERISTICS:
        ( A ) LENGTH: 889 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:52:

| GTGAGTACTT | CTGTATAAAA | TGTTTTAATA | TTTTAAATTG | TATACTTAGG | AAACTTCAGA | 60 |
| AGTTAGTGTT | TTTATTGTTT | GTACTCTGGA | AACTGAGAAT | ATGTTTGTG | AGAGAATACA | 120 |
| GGGAAGCAAA | AATTCTGTCA | CCTAAATATA | AGCACACTTT | TTAAATGTGT | TCAAAATTGT | 180 |
| ATGGCTGTCT | CCGAAGTTTC | TTTAAGCTTC | TGGATTATAA | ATTCTGAAAT | AAATTCTCTG | 240 |
| GGAACTATAT | GGGTGAAAAT | TGATGATGTG | TAAGTGTGGA | AAGTCTTCAG | GGGTGCCTAG | 300 |
| AGCAGCTAGA | CAGATAGTTA | AGCTTCTCAC | CGGAAGTTGC | ACCTACCAGC | AGCTGAAACA | 360 |
| CTGTCAGCAA | AAATACTTGT | CCTGTGTGAT | GGATGAGCTT | GGGGATAGCA | GGATTACATG | 420 |
| TGATACTATC | CAGTTTTTGT | TTTGTTTTGT | TTTTGAGAT | GGAGTCTCGC | TGTGTCGCCC | 480 |
| AGGCTGGAAT | GCAGTGGCAT | GATCTCGGCT | CACTGCAACC | TCTGCCTCCC | AGGTTCAAGC | 540 |
| GATTCTTCTG | CCTCAGCCTC | CTGAGTAGCT | GTGAATACAG | GCACGTGCCA | CCATGCCCAG | 600 |
| CTAATTTTTG | TATTTTTAGT | AGAGACAGGG | TTTCACCATA | TTGGCCAGGC | TGGTCTCAAA | 660 |
| CTCCTGACTT | CGTGACCACC | TGCCTCAGCC | TCCCAAAGTG | CTGGGATTAC | AGACGGGAGC | 720 |
| TACTGCACCC | AGCTATACTA | TCCAGTTCTT | ATAACTACAA | GTTACCCTAC | CAAAGTTTAA | 780 |
| CTTTCCAAAA | AACTATTAGA | ACTTTTAGTA | AATAAAAAAA | TGAAATAATT | AATTGAAATG | 840 |
| GCAGTTTCTG | TGAGAGAGTA | CATTTGTCT | GTATTTGTTT | TTCCTATAG | | 889 |

( 2 ) INFORMATION FOR SEQ ID NO:53:

( i ) SEQUENCE CHARACTERISTICS:
        ( A ) LENGTH: 4586 base pairs
        ( B ) TYPE: nucleic acid (C) STRANDEDNESS: double
(D) TOPOLOGY: linear (i i) MOLECULE TYPE: DNA (genomic)

(x i) SEQUENCE DESCRIPTION: SEQ ID NO:53:

| | | | | | | |
|---|---|---|---|---|---|---|
| GTGAGTTTAG | CCATGCCAGA | AGAGTAGAAA | TACCAGGAGC | AGGTAAGCCA | GGGGTTCTTT | 60 |
| TTTATTTGGG | TAATTTCATG | TTTGTGTTTT | ACTTGCCTAC | AGTATGAAGG | AGAAAATTCT | 120 |
| CATCATACTT | CTCTTAATTG | AAAAAGGTAT | CTCTATGATA | TTTGCTTTGT | TAATATCAAC | 180 |
| TTTCATTCAT | TTTAGTGAGG | TCTGAGAAAA | GAAATTAATA | TAAATTTAAA | ACAAATGTGT | 240 |
| CATGCTGATA | ATTGTTGGTT | TTAAAAGAT | GGGCCAGTAA | TATATGGTCT | TATATGTAGT | 300 |
| GAACATAGTG | TAGGCATTTA | GAAAGTGATA | ATTGACCTGA | CTGGGGCCTT | CATTTAAGAG | 360 |
| ACTGGAGTAA | AATGAGGATC | TACAGTCTTT | AAGAAAATTC | TTTCAAACTG | AATTTCAGGA | 420 |
| CCACGTGGTA | TTATTTCTAA | CAGACACTTA | GAGTGATGCA | GGCCAAGAGT | TTCCCTCCTG | 480 |
| CTATGTGGTG | GAACAGAAAA | CACCAAACTT | CTGGAAAGTG | CCACCAGGGG | AAACACTGGG | 540 |
| TAATCCAAGG | GCCAGTTCAC | CTGGATAGTG | AGCTGCTTCA | GACTTGAGAC | TGGTCTGCTT | 600 |
| ATTCATTCAA | CAGATATTCC | TAAAGCATTT | TATATGTCAG | GTTGTGTCCT | GGACACTGGA | 660 |
| GATAAAGCAG | TGAACAAAAT | AACCACGAGA | ACCCTGTTCT | AAAGAAGCTT | ATATTCCAGT | 720 |
| GTGGGGAGAT | GGACAGGAGA | TAAACAAGTA | AATATATAGT | ATGTTGGGTG | ATGATAGATG | 780 |
| AAGAAAATAG | AGTAGTAATA | CAAATATTG | AGGGGAGGGG | AGAATGGGAT | GGCTGGGCTG | 840 |
| TGGTAGGTAA | GGTGGTTGGG | AACGGTGTCA | CACACCAGAA | GTAAGTGAGG | AAGCAAGCCA | 900 |
| TATGAATAGC | TGGGTAAATG | TATTTGAAGC | TGAGAGCATA | ACAAATGCAA | AGCCATGAGG | 960 |
| TTGGAACAGG | ATTAGCTTTT | TGGAGGAACA | GTGAGAATGC | TAGTGTGGTA | GGAATAGAGT | 1020 |
| GAGGGAAAAA | GTGGTAAGAA | GTGACGGGAG | GCCAGGTGTG | ATGGCTCATA | CTTGTAATCC | 1080 |
| TAGCACATTG | GGAGACTGAG | GCAGAAGACT | GCCTGAGCCC | AGGAGTTCAA | GACTAGTCTG | 1140 |
| GGCAACAAAG | TGAGACCCCG | TCTCTACATA | AAATATTAAT | ACAAAAAATA | AGCTGGCCAT | 1200 |
| GGTTGTGTCC | ACCTGTGGGC | CCAGCTACTT | GCGAGGCTGA | GTTAGGAGGA | TTCGTTGAGC | 1260 |
| CCAGGAGTTC | CAGGCTGCAG | TGAGCCGTGA | TCGCGTCACT | GCCCTCCAGC | CTGGGTGACA | 1320 |
| GAGCAAGAGC | CTGTCTTTAA | AAAAAAAGAA | AAAAGAAGA | AGAAAAAGAA | ATGCAGGGAA | 1380 |
| GAGGGAACAA | GAGAGCCAGA | CAGACCGTGT | AGGCTTTGGA | AGCCATCGTA | AGGACTTTTG | 1440 |
| CTTCTGCTCT | GATTGAGGTG | AAAGCCATTA | AGAGGGTTAT | TAAGAGGAGT | GACTGATTA | 1500 |
| CATTTTTAAA | GGTCTTCTGG | GAAAGTGGGA | TTAGAGGCAA | GGGTGGAAGT | AGGGAGTTAA | 1560 |
| GAAGCTATTG | GAATGATTCT | GGCAATAGTT | TATGGTGGCT | TGCTTCAGAA | AATGGTTTGT | 1620 |
| AGCTGGGCCA | TATTTGGAG | ATGGCACCCA | CAGGATTTAC | CGAGGGTTTG | TATCTAGGGT | 1680 |
| ATGAGAAAA | GAGAACAGTG | ATGTCTCCAG | TTGGGTGAAT | GATATAAAAG | CTAAAATCCT | 1740 |
| GACAAGTGCC | TGTAATGTTG | TAAGTTATCT | GGCCCTGGCT | CTCTCTGAAT | TCATCTACTT | 1800 |
| TCCTCCCTCC | TCACCCACTT | ATGCCACATT | AACCTCCTTT | TTTGTTCTTC | AGATATGCCA | 1860 |
| GGCATGCCTG | CAACACAAAG | CCTTTGCCTT | TGCAATTCCC | TCTGCCTAAA | CTGTATTGCT | 1920 |
| TCAAGAGATT | CATGTGGCTT | CCTTCTCACT | TCATTCTGGT | CTCTGATAAC | CCAACTGCTA | 1980 |
| TGTCAATAAT | AACCACAACA | TCCTCCCCAA | CCCTCAGGAC | TTCTTTTCCC | CCTGACTCTG | 2040 |
| CTTGCTAGTG | TTTCTCTTCG | TATTTATCAC | TGTCTGACAG | TAAGTACGGA | CGTACGTACA | 2100 |
| AAAGAATTGT | TTATTACCTG | TCTCCTTGCA | TTAGAATATA | AGCTTCACCA | AGGCTGTGAC | 2160 |
| CAGTGTTGTA | TGCAGCGCTT | GGCACATAGT | AAACATTCGG | GGAACATTTA | CTACTGAAAT | 2220 |

-continued

| | | | | | |
|---|---|---|---|---|---|
|TTATTAACCA|GGGAACAAGT|CTGGGGGAAC|GGGAATCAAC|AAGTTACGGT|TATTACCATG|2280
|TTAAATTACA|GATGTCTTTT|AAGCATCCTA|CTAGAGAAGT|TGAATACACA|CTTGAGGTAT|2340
|ACAAGACAGG|AGTTCACAGT|TCACACTACA|GGTTAGGGGT|TGTGTATATA|TGTCCTGGGG|2400
|TCATCAGGGT|GGGTACAGAT|AGCCTTTTTT|TTTTTTTTT|TTTTTTTTT|TTTTTTTTT|2460
|TTTTTTTTG|AGATGGATCT|CGCTCTTCAC|CCAGGGTGGA|GTGCAGTGGT|GCAATCTTGG|2520
|CTGCAGCTGT|GACCTGTGCC|ACGGTGGGTT|GCAAGGGATT|CTCCTGCCTC|AGCGTCGTGA|2580
|GTAGCTGGGA|TTACAGGTGC|CTGCCACCAT|GCCCAGCTAA|TTTTTGTGA|TTTTGAGTA|2640
|GAAACGGCAT|TTCACCATCT|TGGCTAGTCT|GATCTTGACT|CCTGCCCTCA|TGATCTTCCC|2700
|ACCTCGACTT|CCTGAAGTGC|TGGGATTATA|GGCGTGAGCC|ACCATACCCA|GCCGTAGATG|2760
|GCTGTTAAAG|CTATAAAATG|AGGAGGGATT|ACTTAGAGGT|ATGAATTGAG|AGAGAATACA|2820
|AGAGGTCTAA|GGACAAAGCT|CAGGGTCACT|CCAAATTTTG|TAAGTCTTCA|TTTGGAGATG|2880
|GAACATCCTA|ATATTTTAA|GATACCGACT|TAATATTTGC|ACCCAAGTTA|AAGATCCTCT|2940
|TGATCAGAAT|GAACAGGAAG|CTTTAAGCTA|AGCACAGTGC|TACCAAGAAG|CACCATGTTG|3000
|ACCTTGAGGA|CTCTGGCAGG|AAGCTGTTTG|TGGTTGTCAC|ACCTAGTTTC|CTCTGTGAAA|3060
|CTACTGCTGC|CTGTGGGTGA|TGTGGTTATA|TGCTGCTGGC|TGCTGTTGAT|TCTCCTGTTT|3120
|GTGTACAAGG|TGTTTTTCCC|TCCCAGTACC|TCCCAATGTA|GGCATCGGTT|CATGCACAGT|3180
|GAAGTAGTTG|CCTGCGAGAA|ACCTTGTAAG|GCAGGGAGCA|GCCTTTGAA|TGCAATAATC|3240
|TACCCGAATC|ATTTTAATGA|CTTAATTATA|GAATGAATTT|CTTTGAGACA|AAGTGAAAGT|3300
|CTTAGTTGTA|TTACACTTTT|AGACATAGAG|GAGACATGTA|GGTTTGTTTC|TGTATACAGT|3360
|AAATTTCTGT|GCTTTTCTAT|ATCTTATGAA|ACTTGAATAG|TTGGCTCTGT|TGCCAGGTGA|3420
|AAGTTTTGCT|AGGTTTTTA|GGAAATTAGG|ATGAGTACAT|TTAAGACACA|GGGAAATTTT|3480
|ATCTTGAATA|GTAAAAGACA|TTGTTAAGCT|ATCGATTCCT|TTCAGAGTTT|ATTTGGAAAA|3540
|TCAGAGAGAT|GTTTTACTGG|CTCCTTTGAC|ACCAAGTCAC|ATCTTCTCCT|AATTTATTGT|3600
|GAAGAATGTT|GACATTAACT|TATTTCTCTG|AAGACCTGTC|TACCTTAGGG|GGCTGTTCTG|3660
|CATCAAGTTG|CCTTTTTAGG|GGATGTACAA|CTTATTATCT|GTCTCTGAAG|CAAATATGAA|3720
|TATTTGGATG|GTGGGTGTAT|TAATTCATTT|TAACACTGCT|GATAAAGACA|TGCCCCAAAC|3780
|TGGGGAACAA|AAAGAGGTTT|AATTGGACTT|TACAGTTCCA|CATGACTGGG|GAGTCCTCAG|3840
|AATCATGGTG|TGAGACGAAA|GGCACTTCTT|AGGTGGCGGT|GGCAAGAGAA|AAATGAGGCA|3900
|GAAGCAAAAG|TGGAAACCCC|TGATAAGACC|GTCAGATCTC|GCGAGACGTA|TTCACTATCA|3960
|CAAGAATAGG|ACGGAAAGA|CTGGCCTCCA|TAATTCAATT|ACCTCCACT|GGGTGCCTCA|4020
|CACAGCACAT|GGGAATTCTG|GGAAAAACAA|TTCAATGGGA|GGCTTCGATG|CAGACATAGC|4080
|CAAACCATAT|CAGTAGGCTT|TTGTTAAATC|ATGGATTTTT|TTTGGAACCA|AATTAATCA|4140
|CAATTTTCTT|TTATCTTTGA|GTGTCTCCCA|AAATAGCAGT|AGATGGGAAT|TGTGAAATTC|4200
|TGTTTCTCAG|AGCTGAGAAT|AATCTTAATT|TTTCAGGTGA|GCAGAATGCT|TATCTTTGCC|4260
|TCCGAGCATA|AGTTTTACAA|GAGGGTATGT|AGGGAGCTGT|ACCTTATTTT|AGAGTTTTAA|4320
|CTTTTAAGAG|ACAAACTTTT|AGTTAGCTAA|AATACAAATT|ATTCTTTCAC|ACCTTCGTCT|4380
|TCACATGGAT|ATTGGCGGCT|CTTAATGCTG|TTATGTTTAA|ATTCCAAAGA|ATGGTGACAT|4440
|TTGAGTCACT|AAAATTTATT|GATATTGTAA|AGATAAAGTC|TATCTGGCTT|GAAGTCCCAT|4500
|TTGTGAAGTG|AATTAAAGTC|TTTCTGGCCT|AAAATAATGT|TCTTTAAAAA|ATGTTTATTA|4560
|ATTCTGTGTA|ATTTTTTTTT|CTTTAG| | |4586

( 2 ) INFORMATION FOR SEQ ID NO:54:

( i ) SEQUENCE CHARACTERISTICS:
        ( A ) LENGTH: 2127 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:54:

```
GTTAGTTTGA  GCCCTGTCTG  CTTTCTAAGA  TTTGGTTATT  GACCATTTTC  CAATTTCCTA     60
TTCTTTCATT  ATTAATGCCT  TAATTCACCC  ATGAATAATT  TTTTATCAAT  TGTATACTCA    120
GTCCTGTTGT  GAGTCTATAG  AGGACCTAGC  AATAAGATGT  ATAAGTGGAA  GATCTTCTTT    180
CCTTAGATTT  CTTTAATATA  ATACAAGACA  CAGTAACTAA  TAACACCAGA  CAGTGTAGAG    240
TAAAACACAA  AAGTGTCTTA  TTGCCAACTG  TTCTTTCAAG  ATTTCAGGGA  GTGGTGACGT    300
GGCGGCGGGG  GGAAGCTCAG  TGATGATGGG  AATAATTGTC  AAAGGACTTT  ATGAAGAGGG    360
TTGACCTGAG  GTAAGTTCTG  AAGGGTGACT  CAGATTTGCC  AAGATTAATA  GAGTTCCACA    420
TGTTCATAAA  GCAGGACAAA  AACCACTGTA  ACTTTTGTAA  GCTCTATAAA  ACATCCTTAT    480
CCTGGAAAGG  AAGTTGACTG  CATTTAGCTC  CTTTGATCTC  CCTGAGACTG  GTAGGAATAT    540
CATTGAGTTT  TAATTAAAAG  CCCAGTAGGC  TGAATCTCAT  CATCTTATGC  ATAACCTTTG    600
GCAAGTTGAT  TTGAAAAGCT  ACCTCCAAGG  TCCCTCTCAG  TCCTAAAACC  TTATGATATG    660
ATAACGTTGA  CCCAAAAGGA  CCCCATTTCT  TTTCTGATGA  TGGTATATCA  AGAAGACCCT    720
ATATGTACAC  ATAAGTAATT  TCCCACTCAT  AGCCAGGCTT  CTTAAATGCC  AACTACTTTT    780
CCTTTAACAT  TTCAGTGAAG  TCTGCTTTAT  TCATAAACTT  GATTGTGATT  TATACTCAAC    840
AAGTTATATC  TCTGTGGCCT  CTTCCTGAGT  CATGTTTTTC  AGATGCACCT  TGTTTGGCTT    900
GAATTTAGAA  GCATTTCGTA  AATACATTTC  AGAAGCCATC  TTAATCTCTG  TGTCTTCCAG    960
ATCGCTTTAC  AGTTCTAAC   TAGGCATAAC  AGCATTTTAA  ATCTTAGGGA  CCATTAGTGG   1020
GGTTAAATAA  TTATTACCAG  TAAATACTAG  GTAAATAAA   GGGTGCTATT  TTTGCTGAAA   1080
GGTATGTGTG  CGTGTGTTCC  CAGAAAAATT  CTGCTTGTAT  ATGTATTCAG  TAGTTATCTC   1140
TAGCAGGACT  GTAATTGATT  TCTATTCTCT  TTATAATTTT  TTAAACTTGC  TTCATTTTCA   1200
CAAAGAATAT  GTATATAATT  ATATATATAT  TTGTGATCAA  GATAAAACA   GTTGTTACAA   1260
AAAGCTTACA  TGGTGATAAT  TTGTATAATG  CTTCTGGATT  GAACATATAT  TGCTCCCTAA   1320
TAATAGAAAG  ACTGAAGTAA  ACCTCGTTGG  CGGGAAAAAA  ATGTAGAATG  CCAGGAACAG   1380
TTTATGTGAG  TCTGTAGTAT  GGGTTTTACA  CCCCTTCATT  CTATTTCTT   CCAGGTGTTC   1440
TTAATGGGAG  TTTTACTGTC  CTCTAGGGAA  ATAGTTAAGG  GCAAGTTTGG  GATAATCAGT   1500
GACTGGGGAT  GTGTAGGACA  GGTGGGGGAC  AGTCATAGAT  ATCGAATGGG  CCCAGGCCAA   1560
GGTTGCTAAA  CTTCCTGCAC  TGAAAGGTGT  ATCCCCGGCC  GGGCGAAGTG  GTTCATTCCT   1620
GTAATCCTAA  CACTTTGGGA  GCCTGAGGCA  AGTGGATCAC  TTGAGGCCAG  GAGTTCGAGA   1680
CCAGCCTGGC  CAACATGGTG  AAACCCCATC  TCTACTGAAA  ATACAAAAAT  TAGCTGGGCG   1740
TGGTGGCAGG  TGCCTGCAGT  TCCAGCTACT  TTGGAGGCTG  AGGCAGGAGA  ATCACTTGAA   1800
CCTGGGAGGT  GGAGGTTGCA  GTGAGCCAAG  ACTGCATCAC  TGCATTCCAT  CCTGGGTGAA   1860
AGAGCGAGAC  TCTGTCTCAA  AAAAAATATA  TATATATAAA  AATAAAGGT   GTAGCTCCCA   1920
CAAGAAAAGT  TTTTTTTTT   TCATTCAAAC  TGGTAATACC  ACCACCTTTG  AAAAGGAAGT   1980
```

-continued

| | | | | | |
|---|---|---|---|---|---|
| ATGGGATCTC | TTGGATTAAT | TTGGGAAGTG | TATAGTTTCT | GTTCAGAGTG | TTTTATATTT | 2040
| ACATGTTAGT | GAAATTATAG | AGACATTTTA | TCCCCTTGTG | ACTTGACAAG | ACCTTTAAAT | 2100
| TATGTTATTT | CTCATTACCT | TTTTTAG | | | | 2127

( 2 ) INFORMATION FOR SEQ ID NO:55:

( i ) SEQUENCE CHARACTERISTICS:
        ( A ) LENGTH: 716 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:55:

| | | | | | |
|---|---|---|---|---|---|
| GTAATTGTGC | TAAAGGTAAG | GTTAACATT | GTTATTCTGC | TTCCATGTTT | GAAGTTTAAC | 60
| TAAATGGAGT | CATTTCTTAC | TAACTAAGAA | AGATGAGGAA | AAGATTATG | ACTTTAGACT | 120
| GGAGGCATGG | ATATGGCTGT | CCAATTTTC | TGGTCAACCA | ACTGATTTCT | GAGCCCTTCT | 180
| CAGTAAGATA | GAAATTTTAG | AATGGTATCT | TTATTATATT | GGACTACTGA | TGCTTCCCTA | 240
| TCTGCAAATC | TTTAGGTTTC | CCTTGTAAAC | TGGAAATTAA | ATAGAAGTGT | AGTGATTCTT | 300
| CAACATATTG | AGAATAAGGA | CAGGAGATAT | CACTGTTATG | GGCGGAAACC | TGGGCTAGGA | 360
| ATTGTTTGCT | GTCAGGAATT | GGAACTAAGT | AGGTGTGGAC | TAGTAAGCCA | ATTACATACC | 420
| TCTTAGCATT | GGTCTGTTTT | GTTCCAACAT | AGAGGAAAAA | AAGGGTGTT | AGTCTTAAAT | 480
| GATATTACAG | TTCCTTATGT | GCCAATTTCA | TTAATAATT | TTAGAAAAAT | GTGACTGTTA | 540
| CCATGAAGAA | AATTAAGGTA | TCTTAGGGAT | AATTAAAACA | CCAATCATAA | GAAGTGTGCA | 600
| TATCTAAAGT | ATTGGGTTGG | TTTTGAATTT | TATTTTGTGA | GTAAAGGAGG | AGGAATGGGC | 660
| CTTTATTTTC | TTTGTGTTCC | AATTTTGTGG | GGGTTTTTTT | TTTATTATTT | CTACAG | 716

( 2 ) INFORMATION FOR SEQ ID NO:56:

( i ) SEQUENCE CHARACTERISTICS:
        ( A ) LENGTH: 837 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:56:

| | | | | | |
|---|---|---|---|---|---|
| GTGAGTAAAA | TAACCAATGT | ATTGATCAGC | ACAATGAAAC | ATAATTTCCT | TCCTGCCCTA | 60
| TTCTGTGGGT | TGTTTCCTTA | CTTTATATAT | AGTCTCCTTT | CATACACAAA | AGTTTTAAT | 120
| TTTGATGAAA | TCCAATATAT | TTTTTCACTA | GTTGCCTGTG | CTTTCGTTTC | ATGTATGTAT | 180
| GTATGTATGT | ATTTACCTAT | TCGAGATGGA | GTCTCGCGCT | GTCGCCAAGG | CTGGAGTGTA | 240
| GTGGCACGAT | CTCGGCTCAA | TGCAACCTCC | GCCTCCTGGG | TTCAAGCAAT | TCTCCTGCCT | 300
| CAGCCTCCCA | AATAGCTGGG | ATTATAGGCA | TGTGCCACCA | TGCCCAGCTC | ATTTCTGTCT | 360
| TTTTCGTAGA | GATGGCGTTT | AGTCATGTTG | GGCAGGATGT | TCTCGAACTC | CAGACCTCAT | 420
| GTGGACCACA | TTCCTTGTGC | TCCCAGAGTG | CTAGTATTAC | AGCTGTGAGC | CACCCATGCC | 480
| TTGCCTGTTG | CCTGTGCCTT | TGGCTCTTCA | ATAACTTTTA | TTTATAACAT | CTTTGCCCTG | 540
| TCATTGTTCT | TCTAAGCATC | AGTGTGTGTG | TATTTTGGTT | AGAGATGTAA | TCTCTTTTAA | 600
| GATACATTTT | ATATAGGTAA | GGTTTTAAAA | TTCTCATACA | TTCCTTTTAT | ATATTTCCTC | 660
| TACTAAAAAA | TGGGCTTTAT | TTATATAATT | AAGAAAGGTT | TTGTAAGAAA | ATAAGGACAC | 720

| ACTTTGCACT | CACTCAGAAA | ATGAGACTTT | CTTTGGTATT | TTCACTTAAG | TTGCACTGGG | 780 |
| TATGAAATGA | CTTTTTAGAC | TAAGTAGATG | TTTCTAATGC | TGTACTTTAT | TTTATAG | 837 |

( 2 ) INFORMATION FOR SEQ ID NO:57:

( i ) SEQUENCE CHARACTERISTICS:
        ( A ) LENGTH: 1081 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:57:

| GTATTTCCCA | AAAAATATGA | TACTAATGGG | GATATTGTAG | ATGAGACCAA | CTTCCTGTTG | 60 |
| TTAGTCATTT | AGTTCAAGTT | AACATCTAAG | AACATTTATT | CTGTTTCTAT | TTACATAGTT | 120 |
| AATCTCTACT | TGTGGAGTAG | AAAAGAAATA | GAATCTTAAG | ACCTATGTAA | ATTCTTTTAA | 180 |
| TATTGTATGA | AAGATCTATT | TTGGGTAAAA | GCTTCGATTC | CTCTCTATCT | AATAAAAGTT | 240 |
| TTTAGAATAC | TGTGATTTTT | ATGAGCTGAG | AAGGCTTAAA | AAAAGTAGCA | CACATGTCAC | 300 |
| TAGCTAATCT | TGTATAGCAG | CCTTTCCTTA | TCTTATGAAA | ATTAAATACC | ATTGAAAATG | 360 |
| TCAGAAAAAA | AATAAAAAGT | TGTCTTTCAT | GTGTTACAGA | GAGGCATAGA | GTTAAAAGCA | 420 |
| TTGATTTGGT | AGCTAGTTCT | TCCCCCTCCG | GAGATGGAGT | CTTGCTCTGT | CGCCCAGCGT | 480 |
| GGAGTGCAGT | GGCGCCATCT | CAGCTCACAG | AAAGCTCCAC | CTCCTGGGTT | CACGCCATTC | 540 |
| TCCTGCCTCA | GCCTGCCGAG | TAGCTGGGAC | TACAGGCGGC | CGCCACCACA | CCCGGCTAAT | 600 |
| TTTTTGTATT | TTTAGCAGAG | ACGGGGTCTA | CACCGTGTTA | GCCAGGATGG | TACTCGATCT | 660 |
| CCTGACCTCG | TGATCCTGCC | CGCCACGGCC | CCCCAGAGTG | CTGGGATTAC | AGGCTGGTAG | 720 |
| CTATTTCCTT | GATACTGACT | TAGCATATGA | GTTTATGCTT | AACTCTCATA | AGATAGACGA | 780 |
| AACTAATTTT | TATAGTGGCA | TAGATTAAAT | GTTAGAGAT | TTTTATATGA | AATTTTAAGA | 840 |
| GTAATGTTTT | TCAACCTCAA | TGTACAAAAC | ATGTATTTTA | TTAAAAAATT | TTGAAATACA | 900 |
| TCACAATGTA | AACCATTTTA | TATAATTCAT | AGTTTGAACT | ATAATTATTT | ACAAAGACAG | 960 |
| TAAAAGGAAG | AGCGGCTGTT | TCAAAATAAT | ACTTCAACTT | GTAATTTTGA | CTAATTTCTT | 1020 |
| GTCTAAATAT | TTAAAAAATA | TTTAATAATT | ATTCAGTGAA | CCAAGACATT | TTTTATTTCA | 1080 |
| G | | | | | | 1081 |

( 2 ) INFORMATION FOR SEQ ID NO:58:

( i ) SEQUENCE CHARACTERISTICS:
        ( A ) LENGTH: 1455 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:58:

| GTGAAAATCA | ACATCTTTTT | ATGAGAAAAA | TACATCAATA | TCTAATCTAT | TAATAATCCT | 60 |
| TTTGGGGATG | GGAGGGTGGC | AGTTAGGTTT | AATATGTTAT | AATTACACCT | TGTTATGAGA | 120 |
| AAAATCTTGG | ACTGTAACGT | CCCTCTCTAC | CCACAAATTG | GGAAGGTGCC | AAGAGACCAA | 180 |
| AGAATGACTC | AGACAAGTCC | AGCTCGGCAA | GTACATAACG | TCTATTAAGA | CTTACATATG | 240 |
| GAGGAGGCAG | AGGTGGTGGG | GAAAAATAAA | AGACTTATAT | ACAGGGTACT | CCTAGGTAGC | 300 |
| AGCAGGACAG | CTCTAGAGAT | CCTCGCTACC | TCCCATCGCT | AAGCTGCTTT | TAAGCTAATT | 360 |

| | | | | | | |
|---|---|---|---|---|---|---|
| TTCTGGCTCT | TTGCCTACTA | TGTGTGTGCA | CGATGGGACT | GTTTTCCTTG | GTAGTTTCTC | 420 |
| AGATCTTCTC | TGGGATGTTG | GGGTTCTCAG | GGACACCTGT | TCCTTGGCTG | GGCACCATGG | 480 |
| CCTTGGCTCA | CTGCCTAGCC | TTCAGGGTTT | AGGCAGCAGA | CATACACCCT | TAAGTAAGGT | 540 |
| AGGTGACCTG | TCACATTTCA | CCCCATGTCA | AAGAGGAAAC | GAGTCAGATA | ATTTGTGGTT | 600 |
| GCCCTAAGAT | TTTGGTGACA | GAGTAAAAAT | TCAGTGTTCT | TTCTTGATTT | CCTTACCAAG | 660 |
| TTTCTTTCCC | ATAGAGCAGT | GGTCCATCCT | TTTTGGCACC | AAGGACCAGT | TTCATGGAAG | 720 |
| ACAATTTTTC | CATGGACAGG | GTTGGGGGTT | GGAGAGATTT | TGGGATGATT | CATCTGCCTT | 780 |
| ACATTTATTG | CACACTTTAT | TTCTATTATT | ATTACGTGGT | AATATATAAT | GAAATAATTA | 840 |
| TACAACTCAC | CAAAATGTAG | AGTCAGTGGG | AGCCCTGAGC | TTGTTTTCCT | GCAACTAGAT | 900 |
| GGTCCCATCT | GGGGGCGGTG | GGAGACAGTG | ACAGATCAGC | AGGCATTAGA | TTCTCATAAG | 960 |
| GAGCATGCAA | CCTAGATCCC | TTATGTGTGC | AGTTCACAAT | AGGGTTCACA | CTCCTGTGAG | 1020 |
| AATCTAATGC | CACCACTAAT | CTGACAGGAG | GCCAGCACAG | GCGGCAATGT | GAGCGATGGG | 1080 |
| GAGCAGCTTT | ACATACAGAT | GAAGCTTTGC | TCGGATGCTC | ACTGCCTGCT | GCTCACCTCC | 1140 |
| TGCTATGTTG | CCCAGTTCCT | AACAGGGTCC | ATGGCCCAGG | GGTTGGGGAC | TCCTGCTTTA | 1200 |
| GAGTGGTTGA | TATTCAAACT | CCTCTCCAAA | CCAGTCAATG | AAGTTTGACT | CATATTTAGT | 1260 |
| ATCCAATTAC | AAGGTTTTGA | ATTTTTTGAC | TGCCAAAAGT | TTTTTTTTA | ACTTTATTAT | 1320 |
| TAAAATGGGA | AAGACAGCTG | ATTTTATTTA | GATGGAATAA | TTGTTAAGAT | ACTTCTTCTG | 1380 |
| CCTTAGATTA | CTATTGTATT | TGTAATTAAA | GTGCTCGTTT | GGATACTGGC | ATTCTGTGTA | 1440 |
| ACCAATTCTT | CATAG | | | | | 1455 |

( 2 ) INFORMATION FOR SEQ ID NO:59:

( i ) SEQUENCE CHARACTERISTICS:
        ( A ) LENGTH: 2741 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:59:

| | | | | | | |
|---|---|---|---|---|---|---|
| GTAAGTTTAA | CAATACTAGG | AGAATATCTT | GGGGCTTACT | ATCTGGAAAT | TTAAATTTCA | 60 |
| TCTAACCCTA | CAAGTGAAGT | TAATAGGGTA | TACATAGAAG | AAAATATTCT | ATGCATTTTG | 120 |
| GTACCCATGG | ATCACTTAAA | AGAAGGGCCT | TTAAAGACTA | AGAACACAGG | AAAATGCATG | 180 |
| ATATAACAGG | TATCTTTTAA | AAAGGATAGA | CTGCTTTATT | TATTTATTTA | TTTATTGAGA | 240 |
| CAGAGTCTTG | CTCTGTCACT | CAAGCTGGAG | TGCAGTGGCC | CAATCTCAGC | TCACTGCAAC | 300 |
| CTCTGCCTGC | CGGGTTCAAG | CGATTCTCAT | GCCTCAGCCT | CCTGAGTAGC | TGGGACTACA | 360 |
| GGCATGCGCC | ACCACGCCTA | GCTAATTTTT | GTATTTTTAG | TAGAGAAGGG | GTTTGCCAT | 420 |
| ATTGGCCAGG | CTGGCCTTGA | ACTCCTGACC | TCAAGTGATC | CGTCTACCTC | GTTCTCCCAA | 480 |
| AGTGTTGGAA | TTACAGGCAT | GGGCACCGTG | CCCGGCTGAC | TGCTGTATAT | TTAATATGAT | 540 |
| CCCTATTTTT | AAAGTGTATG | TTTATTTATG | AGCATACAAA | ATAGTGGAAA | TGGAAAAACC | 600 |
| AAACTGTTAA | GATCATTGTT | GGGTGAATGA | ATTCCTGGTG | ATTTCTGTAA | AATTTTTAAG | 660 |
| GCAAATACAT | ATTACTTTTA | AAATCAGAAA | TAGAAAAGCC | TTCTTAAAGA | TAGAGCTGCA | 720 |
| TGATCCAGTT | AGGTATAGAC | AAGCCAGTGA | GTTAAGACAA | CTGAGTATGT | TCCACTTTGT | 780 |
| TGAGCTGTGC | TACCCTAGTT | AATGTGACAT | TAGTGCTGGC | CCAAGAAATA | CAGAAAAGGG | 840 |
| CAGTTTTGCT | ATCTATCTGG | TTTATATTTT | TTAGGCAGCT | GCTTAGAAGA | TCTGCAAGGT | 900 |

| | | | | | |
|---|---|---|---|---|---|
| GAAAGGTTTT | AGTTTACATA | TGTGAGATAG | AACTACTTTT | TTAAAGAGCA | ATTCAGTAAA | 960
| TCCAGAGAGT | TCTAAATCCT | TGGATCCAAT | TAAAAGAATA | TTGTTATTTG | TAGATCAGTT | 1020
| TTATAATGTA | ATTGATAAGA | ACTGGCTATA | GAAGGAATAC | CAGTTTAAA | GTCAGGATTC | 1080
| ACTCTAGGCT | GGGCATGGTG | GCTCATGCCT | GTAATCCCAG | CACTGTGGGA | GACCTAGTGG | 1140
| GGAGGATCAC | TTGAGCCCCG | GAGTTCAAGA | CCATCCTGGG | CAACATAGCA | AGATACCATC | 1200
| TCTACCCCCA | ACCCCCCCAA | AAAAATCACT | CTAAGTGTAT | ACTTAATACA | CATGGATGAT | 1260
| CCTTATGAAA | AGTCCTCATT | TTTGAAAGAT | CTGAGAGCTG | GTCTTTCTTA | GTCTATTTTT | 1320
| GTAGAATTTT | CCGTTCCCTA | ATCTACAGAT | TAGGAAGACT | TGACGTTAAC | TTCATTTTCA | 1380
| ATGTCTTACC | ACTTGCTCAG | TTTTCCTGAG | ATCTCTTGAT | ATTTATGGA | GGAGAAATGA | 1440
| TCATAATCTA | TTCTTTGCTG | ATTCTGCAGC | TTTGTACCAA | ATACAAACTC | AGTAAGTTTA | 1500
| TTTACTTTTG | TATCATCTGG | AAATAGAAAT | GTTAAGCCAC | AGTTTGTTAG | GATTACTCC | 1560
| TATCAGTACT | TCTTACAAAC | TTTGCTATGT | ATATTTAAA | TTTTAAAAAC | ACTCTGATGC | 1620
| ACAGCTCTTA | GAAGTGGACA | CAGAAGAAGG | AAGAAATGCT | TCTCAAAAAT | TCAGACATTG | 1680
| GTGTGAATAC | TTAAAAATAG | ACTAAGCCAT | AATGGGTTGT | GTACCACTGA | ATCATACACT | 1740
| TAAAAATGGT | TGAATGGTAA | ATTTTATGTT | ATATATATAA | CCACAATTTT | AAAAAACTAG | 1800
| CCTGTAATAC | CAGCATTTTG | GGAGGCCAAG | GCGGGTGGAT | CACCTGAGGT | CAGGAGTTCG | 1860
| AGACCAGCCT | GGCCAACATG | GTGACCTCAT | CTCTACTAGG | GAGGCGGAAA | GTAGCCATGC | 1920
| CGTGTGGCAT | ATGCCTCTAA | TCCCAGTTAC | TTGGGAGGCT | GAGGCGCAAG | AATCACTTAA | 1980
| ACCCAGGAGG | CAGAGGTTGT | AGTGAACCGA | GATCAGGCTA | CTGCACTCCA | GCCTGGGTGA | 2040
| TAGAGTAAGA | CTCTGTCAAA | AAATAAATAG | TAACAATTTG | CCCCAAACCA | TTGAATTGTA | 2100
| TAATTTAAGT | AGATGAAATT | TATGGTATAT | AAACTGTTTT | AAAAAAATAA | ATTATGCTTA | 2160
| ACTGAATCCA | AATCATGCAT | GTCCACCTTG | CTTAAGAACA | TTATTGAGTT | TTAATAATTT | 2220
| TTTATATGTG | GAAAAAGACA | GAGATCCAAA | TTGATAAAAC | CGGTGGCGGC | GGAATGCTCC | 2280
| TAGATGACAT | ACTACCAATC | AGGTCCCCTT | ATCAAGTAGT | GGCTCTGTAG | TAAAATCACA | 2340
| TCTTACATGA | GTGGTAGGTA | GAAAGTGGAT | ATGATAGAAA | ATATTATAGA | AAAATATAAT | 2400
| ATAGAAAAAT | AGGGTAATTC | CTTAAATTGC | CCCTAAATCA | TGAAGGTTCT | TTAGTAGTGG | 2460
| AAGACAGAGT | CAGGTCTGAT | TTGGGAAAGG | GGGCGTGGAG | AAAGGAACAC | TGCAAGACAC | 2520
| AAAATTCCGT | TTTAAAATTT | TGCTCTCAGT | AGTGTTCACT | GAACACGAAT | GAAAGTTCAC | 2580
| TAATGAATAT | AGGTAAGATT | AGACTTCTGT | AATTCTTGTT | TGCTTTTTGA | ATTATGAAGT | 2640
| ATTTCAAACA | CTGTAGTTAT | TTTTTAACAT | AAGAGCTTGG | ACGGAAGTCA | GATCTGAGTC | 2700
| TCCTTGAGTT | AAATGCTTTG | TTTGATTTGT | TTTGACCCTA | G | | 2741

( 2 ) INFORMATION FOR SEQ ID NO:60:

( i ) SEQUENCE CHARACTERISTICS:
        ( A ) LENGTH: 197 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:60:

| | | | | | |
|---|---|---|---|---|---|
| GTAAGGAAGG | CAGAGTTGGA | TATTGAGTTC | CTTCTCTGTG | GCATGTATTG | AAAAGTTACC | 60
| CGAGGTTTGG | CTAGAGTGAC | ATAGGGACA | GAGGAGTGAT | GGGGAGAGAG | GGTTTGGGAG | 120

-continued

| AGCAGAAATT | GTAAACCTCT | GCCCGGAGAA | CCTCTTATTA | TCAACATTTT | CTTCATGCTT | 180 |
| TTTTTCTCTG | TCACTAG | | | | | 197 |

( 2 ) INFORMATION FOR SEQ ID NO:61:

( i ) SEQUENCE CHARACTERISTICS:
        ( A ) LENGTH: 82 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:61:

| GTAATTTTTC | ACATACCTTA | TCAGAGCATG | AGCTTGGGAA | ATACAAGTGT | TAAACAAAGT | 60 |
| TTGAAATGTT | TTTATCTCCT | AG | | | | 82 |

( 2 ) INFORMATION FOR SEQ ID NO:62:

( i ) SEQUENCE CHARACTERISTICS:
        ( A ) LENGTH: 1079 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:62:

| GTGAGTACCA | TTTGGAATTG | TAAAGGCAAA | GATAGGTCTT | CATTACTGAG | TAACATTTTT | 60 |
| TAACCACTGT | CTTGAGATAC | AGTTTACATG | CTCTATAATT | CACCTATTTA | AAATGCACAA | 120 |
| CTAAATGGGT | CTTAGTATAT | TCACAGATAT | GTGCAATACT | CACCACAATT | TTAGAACATA | 180 |
| ATATCCCATT | GTATAGTTAT | ATGAGAGTAT | TTTTATCCAT | TCATTAGCTA | ATGTATATTT | 240 |
| CAGTTGTTTC | TACTTGGGGC | ATATATGCAT | AATACCACTA | TTAGCATTTG | TGTTTGGGTT | 300 |
| TTGGTATAGA | CATGTATTTT | CATTTCTCTA | GGGTATATAC | CTAGGAATGG | GCTGCTGGGT | 360 |
| CATACATTAA | CTGTGTTTTA | CCTATTTAGG | GAATTGCTAG | ATTGGTTCTC | CAAAGTACTG | 420 |
| TACCATCTTA | CACTTACACA | GCAGTATAAT | AAAGATTTTA | GTTTCTCCAC | TATCTCATTA | 480 |
| ACACTTACTA | TCTTACTTTG | TTTAAATAAC | TTATTGAGGA | GAAATTCACA | TAACATAAAA | 540 |
| TTAATTGGGT | TTTTCTTTTC | TTTTGGGAGA | TGTTGTTTCA | TTCTTGTCAC | CCAGGCTGGA | 600 |
| GTGCAGTGGT | GCATCTCAGC | TCACTGCAAC | CTCTGCCTCC | CAGGTTCAAG | CGATTCTCCT | 660 |
| GTCGTAGCCT | CCCGAGTAGC | TGGGATTACA | GCCATGTGCC | ACCACGCCTG | GCTAATTTGG | 720 |
| GGATTTTTAG | TAGAGATGGG | GTTGACCATG | TTGGCCAGGC | AGGTCTCAAA | CTCCTGACCT | 780 |
| CAGGTGATCT | GCCCACCTCG | GTCTCCCAAA | GTGCTGGGAT | TACAGGTGTG | AACCACCGCA | 840 |
| CCTGGCCTCT | AAGTCTTGAT | TCACATACTA | TAGACTCCTA | TTGTTTTTAT | TGAATTTAA | 900 |
| TAGATATTCT | TGAATCGATG | TATCTTCATT | TGCTATATGC | CGTTAATACC | ATTTCCAGAG | 960 |
| ACTTTAAATA | GCTTTTATAT | AATTTTCACC | CCTTTTACTG | GGCAGCAGGT | TCACAGAGCT | 1020 |
| CCTCACACTA | TTATGGTGGT | AGTTGCTATG | TCTCTCAGAG | CACTCTTGCT | GTTTGCCAG | 1079 |

( 2 ) INFORMATION FOR SEQ ID NO:63:

( i ) SEQUENCE CHARACTERISTICS:
        ( A ) LENGTH: 659 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:63:

| | | | | | | |
|---|---|---|---|---|---|---|
| GTAACTACAT | TTTCTCTATG | GGCTGCAAAA | TAAAGCTTAT | AGTCTGTGAT | GAATACAAAA | 60 |
| AATTACCCAT | AGTTGACTCT | GTGGCCTTTT | TTCCAAGATA | AACACCTGGG | ACTCTACTTA | 120 |
| AGGAAGTTTC | TACTTTAATC | TTTATTCTTG | ATGTCACATG | TTGATTAAGG | TCTCTTTTCC | 180 |
| TCAAAAGGCA | ACAATGTTAA | ATATTTCATT | GCCTTCTTAA | TTCAGAAAAA | TCACAAGATA | 240 |
| GGAATTAAGA | AGTTACTTGG | TTTCTATGTC | ACCTTTCATT | CTGGTTTAGT | AAACATACTG | 300 |
| TAGGTTTAAC | CAAGAGAATG | TCACATGGAA | ATTTAAAACC | CACTTCGACT | TTATTACCAT | 360 |
| TCATCTCTGA | GAGGCAAATC | GGCCAGATCT | GTGTATCTTA | CTTAGAATGA | CTTGACATTA | 420 |
| TGGTTGGGTG | CTGTCACTGC | AGTGTAGTAC | TGCAGGTAGT | ACTTGGCATG | TGATGCTAGA | 480 |
| TGGGCTCTGA | TTGAATCCTG | GATCTGTTAT | AATTTGAGTT | ATGTTTCTCA | ACCTGTTCTG | 540 |
| AGGACAACTA | TTGCTATACA | GGTTATTGTG | AAAACCAAGT | AACATATGTG | AAGGTCCTAT | 600 |
| CACCAAGGGT | GTGCTCAACA | AATACTAGTT | TATGTCCCCT | CCTCATTGTT | TCTCTAAAG | 659 |

( 2 ) INFORMATION FOR SEQ ID NO:64:

( i ) SEQUENCE CHARACTERISTICS:
        ( A ) LENGTH: 572 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:64:

| | | | | | | |
|---|---|---|---|---|---|---|
| GTGGGATCTT | TGTGAACTAC | AAGACAAAAT | TAGGAGCTTT | TCTTACTTTT | TAGGCCTTGA | 60 |
| AGAAGTAACT | AAGCATTACT | AAATGAAATA | ACTATAGAAA | CTATGAAAGT | GTTTTATAGA | 120 |
| TCAGTAAACC | ATATTCTAGC | TGGCAAAACT | GTCCATTACA | TAGCTTTGGG | GCACAATATT | 180 |
| ATGTAACATA | TTTCTCCAGG | AGAATTAGAG | CTTTCAGGGA | GGAATCTGCT | TGCCTGAGTT | 240 |
| CCAGAAAGGT | CTGATATGTC | AATTGGAACC | ATGCTATGGA | AATACCATCC | CCTGCCTGTC | 300 |
| TGCTTTGTAC | CACTTAGTAC | AGGGCTTAGG | TCCTAGAAAA | TTTGGTGTAA | CTTATTAATG | 360 |
| GACACTACTC | AGAAAGCCCT | TGCTATGGTT | ATGGCATAGG | GAGAAAGTTA | ATATCCTAGC | 420 |
| TGAGCTTTGC | TTTTTGGTGT | GAAGAACAGA | GTGCCTATTC | ACTGTTATTA | GCAAGTAGTG | 480 |
| CAGGTAGCTG | TTCCCTTTCT | CCTACTTTTA | AAAATTAAA | ACAGTCACTA | TTAGCAGCCT | 540 |
| TTGTTCGACA | GCCTTGGTTC | TCCTGGCTGC | AG | | | 572 |

( 2 ) INFORMATION FOR SEQ ID NO:65:

( i ) SEQUENCE CHARACTERISTICS:
        ( A ) LENGTH: 901 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:65:

| | | | | | | |
|---|---|---|---|---|---|---|
| GTAAGTATGA | CAGGGATTAT | TTCATACTTT | TCTCACTCAT | GAGTGTTGAG | GAATCATTTA | 60 |
| TGATTTATAT | ATGGACCATT | CACCTGGTCC | GTATATAAAC | TAGTTTTGGC | CAGGTGTGGT | 120 |
| GGCTCACACC | TGTAATCCTA | GCACTTTGGG | AGGCCGAGGA | GGGTAGATCA | CTTGAGGTCA | 180 |
| GGAGTTCAAG | ACCAGCCTGG | CCAACGTGGC | AAAACCCAGT | CTCTACTAAA | CATACAAAAA | 240 |
| TGAGCTGGGC | GTGGTGGCAC | ACACTTGTAA | TCCCAGCTAC | TCTGGGGGCT | GAGGCAGGAG | 300 |

```
AATTGTCTGT  ACATGGAAGG  CGGCGGCTGT  AGTGACCTGA  CATTGTGCCA  CTGCACTCCA    360

GCTTGGGTGA  CAGAACAAGA  CTCTGTCTCA  TCACTAAGCT  AGCTCTACAA  ACACTTCTCT    420

TATGTACAAT  GAGGAAGTCT  GTAATCTACC  TAACCAATAT  AAATTCTACT  GTTGTCAAGC    480

ATCAACCGAG  TAAGATTGTA  TTTGGAGTCC  CCGCAAAGTA  TAGTAGTACA  AGAGGCAGGC    540

TACATGGGTT  CAAATTTCCC  AGTACTTAAC  AGTGGTGGTA  ACCCTGCAAA  TCATTAAATT    600

TTCTCTGTAC  CTCATTTCCT  CATATATAAA  ATGGGAATAT  AACTAGTTCC  TAGCATATGG    660

GGTTGTTGTA  AGGATGACAT  GACATAATGT  ATAAAAATTG  CTTACAATAA  TAACTGGCAC    720

AAACTAAGCA  CTTAAGGTTT  GCTATTAGAA  TATTTTTCTT  TAGGTTAAGT  TATTGCTAAA    780

ACATCACTCT  GTCATTCATA  AAACTACTGG  TTTAGCACAC  CTCTTCACTC  AATAATCATT    840

TTCAGTAAAA  ATAATTATAA  ATTTTTTTTC  TTAGAATTAC  TGATTTTTTT  TTTTAAACA    900

G                                                                        901
```

( 2 ) INFORMATION FOR SEQ ID NO:66:

( i ) SEQUENCE CHARACTERISTICS:
        ( A ) LENGTH: 4220 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:66:

```
GTGCGCTCGC  GGGCGGAGGG  GCGCTTCCGG  CCTAGTTGGT  GTGAACCGGT  GCCTTCCGAG     60

CCGTGTCGCG  CGCCTCGAGA  GACTCTCGGG  CGGGTTGCGG  GCTCCCAGCC  CCGAGAGGGG    120

TGGGGACTCC  CTCTGCGCTA  TTCCGAGGCT  CTTAGCCGCT  CCGAGGGTTA  ACCCGCTCTC    180

GCCGGGCTTT  CCTGCGGCTT  CCGAATGGGG  AACGTGTCTT  GCCCTAAAGT  AGCACAGCAA    240

GGTTGAGATC  GCGTTGGGGC  CCCGTTGAGG  AAAATGGGTG  TGTGTGGTCC  ATCTGACCCC    300

CCGCCCGTCT  TGTTAGTAGA  ATGAACTAGT  GTCGTTGTCA  AGACCACACG  GACAAGGGGA    360

GGGGACTTGC  CCTTATTTGC  ACCGCGATTA  ACCGGGTTGT  GGCACCTGGG  TCTCCACGCG    420

TCTCCGTCTG  TTCGCTTCCC  CCTGTTAACC  AAATTGCCTT  TGCCCTGGCG  TTGCGGGCGT    480

TTGAGTCAAC  GTGCTGATGC  GTTTTGGGCT  GTGTTTACGT  CTGTGTAAAC  AAATTAATAC    540

TCATTTCCCC  CCAGGCCATA  TGAAATGAGC  CCACCGCCGA  CCCGGATGTT  TACACATGCC    600

CCCATTTGTC  ACTACGATCA  GGACTGTGGC  TACCTCCAGG  GCTTTTGGT  CACCCCGCGC    660

ATTGCACAGG  ACTCCTGTTG  TCGTCGCCAT  CCGGGTGTGT  TAGGTCGCAG  CCTTCGGCAC    720

AGGGCTTGCA  CCATGACAAA  AATGGCCATT  CTAGCCAGTG  AGTGTCAGCT  TTGTATGCAC    780

CTCCCCTTCA  TGGGCCAATG  GGAAGTGACA  CGGAAGTACG  GATTGTTTAT  CACCTGTTTG    840

ACTGTGTGTG  TGGCATTTAA  ACCTGAGGCC  ATTTGATTTC  TCAAGTCGTT  TTATAATTAA    900

TTTGTACAAA  GAGTCGGGCA  AATACGTCCA  GGATGCAAAG  CCTAACGAAG  GTATTATTA    960

AATATGATGT  TTTTGGCTAT  GTGTACTGAT  GACTGAGGTT  ATTTTTAATT  TGTATTTGCA   1020

TTAATACAAT  TTTAATTCAA  TTACTAGTTC  CCTCTTTGAA  TTGTTAGGTC  TGCACAACAT   1080

ACTGTATGGT  GGCTTTACAA  CCCGACAGAC  CTGAAACCGC  TGAAAAAGTT  CAGTATGGTG   1140

ATCTCTAAAC  TGGAGATATT  TGTGTTTACC  TCACAGAGCT  GTTCTGAAGA  TTAAATAAGG   1200

CAATAATGTA  GTTTCTGGCA  CATAAAGCAC  CCATATGGAC  AGTGTTTTCA  AGTTACTAA    1260

GCTCTTTGTA  TATTTACATG  ATCTGGCTGA  GTAAGCTATG  TTCCTATTCA  TCTCTCAGTG   1320
```

| | | | | | | |
|---|---|---|---|---|---|---|
| CCTTTCTGTA | GTCTGGCAAA | GAGAAGGACT | GGTTGGCTTT | TTATGTTGTT | TTTTGTTTTT | 1380 |
| TGGGTTTTTT | TTTGGTAAAT | GGCCTTAAAG | GCTTCCAAAC | AAGCTCTTAT | TTTACCCTCA | 1440 |
| AGATAATCCT | GTAAATCAGA | TAGAACAAGC | ATTATCGCCA | TTTATTGAG | GTATTTCAAC | 1500 |
| TCATAGCAGT | TAAGTTGTAT | GAAGTCTAGT | GATACATGAG | CAAGTATCAC | GTAATAGCTG | 1560 |
| GTTAGTAAAT | TATTTTTGAA | ATCATGTTTG | ATTACTCAAT | TCTTTTGATT | ACTGAGACTT | 1620 |
| TAGTTTCAGC | TTCTTAGCCC | AGTTTATCAG | TAAATGATTT | ACTCAGTAAA | ATATTCATCA | 1680 |
| AATATTTCTT | GAGCACCTAT | TACTTGCTAC | ACATTGTTCT | AGGTGCTGGA | TATAGAGCAC | 1740 |
| AAACTGCTCT | TGTGGGGCTT | ACAGTGAGGT | ACGCTGTGAC | AATATGGGAT | GTCATTCTCA | 1800 |
| TGGGAGTGCA | AGGGTAAAAT | AAAGCTCTTA | TGATGTTTAA | TACAGAATAC | TGGTTATGGA | 1860 |
| ATTTTAACTT | GATTTCTTGT | ATTTTCTGTG | CATTTTTAAC | CTGTAACTCA | TTCTCACAGT | 1920 |
| CCTCAGCCAA | GAAAATGCAG | CCTCTGAGAC | TGTTAAGTAA | TTTCCCCACT | GTGTTATAGC | 1980 |
| TACTGTATGG | CAGAGCCGGA | ATTGAAACC | AGATCTATTT | GACCCTAGAA | GATGTGACCA | 2040 |
| TGAGATGTTA | ATTTTGAGGA | TAACTTTTTT | AGTATTATGG | AATTTTCAAC | ATATATTTTT | 2100 |
| TAGGACCAAA | GATAAACTAG | GCACAGAGTC | TACTCTTTGC | ATAAATTATT | TAAAAGAGCT | 2160 |
| TCGCGCTCCA | TTTTGTCATC | TAAGCACTGT | AAAATTCTCA | CAAGACTAAT | TCTTCTTTTT | 2220 |
| AGGAACGATA | TAGTTGTAAA | CTTTCTATTT | TTTTTCTTTT | TTTTTCTCC | CTCCACCATC | 2280 |
| CAAGTAGTTG | TGAATTTTCT | AGAGCCAAAA | TAGAACACTA | TAGATTATCT | TTTAAACCCT | 2340 |
| TTATTGAAGC | AGAGGATAAT | GCTGTGACCG | ACTTAACTTT | ATGCTTCTA | AGAGATATTG | 2400 |
| ATATAGTAGA | GAAATGCAGT | AGTTATGCAT | CTCCGTTTGC | TTTTACATCA | TAAATCAAGA | 2460 |
| ATATTATGAA | ACCATCTCCC | AGAGATATAT | GTGATACACA | GATCTTGGCT | GTTTTTTTT | 2520 |
| TTTACAAAAG | TAACATCTAT | GCTATTGATA | CATATAAGTG | GGTTTGTAAG | ACAGTCTATG | 2580 |
| TGTAAATGTG | AAAAAAGGAA | GAATTTCCAG | TTCTTCTCAT | TTTCATTTAG | ACCAGTAATG | 2640 |
| AATACAGTGA | AGCTAAAGGA | CATCTTCCAT | CCTTCCTCGC | TTTTATAGGG | AGAGGAAAGT | 2700 |
| TGTATCACTT | CTTGAGTAAA | AAGAATTGTG | ACGATCTTTT | ACAAACAATG | CCTTAAAAAT | 2760 |
| TATTATTTTT | GAATGATATG | TGGTAGTGGG | ATCCACAATA | GTCTCATTTG | GTTATACAAA | 2820 |
| TAAATTTTAT | GTATTCATGT | ATGTGTTTTG | ATTAGGTATA | AAATTAGTGG | CTGAATATCC | 2880 |
| ATTCAAGCTT | AATTTTGTAT | TTCTATCACT | TTTGTAGATT | TTGAGCAAGA | TTAAAAATAT | 2940 |
| AAACAATAGG | CCAGGCGCAG | GGGCTCACGC | CTGTAATCCC | AGCACTTTGG | GAGGTCTAGG | 3000 |
| TGGGCGAGTC | ACGAGGTCAG | GAGATCAAGA | CCATCCTGGC | TAACACATTG | AAACCCAGTC | 3060 |
| TGCTACTAAA | AATACAAAAA | ATTAGCTGAG | CGTGGTGGTG | GGCACCTGTA | GTCCCAGCTA | 3120 |
| CTCAGGAGGC | TGAGGCAGGA | GAATGGTGTG | AACCTGGGAG | GCAGAGCTTG | GAGTGAGCCA | 3180 |
| AGATGGAGCC | ACTGTACTCC | AGCCTGGGTG | ACACAGTGAG | ACTCCATCTC | AAAAAAAATA | 3240 |
| AAAATAAAT | AAAAATAAAC | AATAATATTG | TTTGCATTAC | TATGGCTATA | TAGCAAATTG | 3300 |
| CCTTAAAACT | TAGGGGCAGA | AAGCAATTTG | TTTTGGTCAC | AGGTTCTGTG | AGTAAGGAAT | 3360 |
| TCAGGCTGGG | GACAGTGTGG | ATGTCATGTT | TCTGCGTCAA | AATGACTGGT | ACCTCACCTG | 3420 |
| GAAGACTTGA | GCAACTAGGT | ACTGGCACAG | CTGGAGCTCG | TTGGGCATCT | CTGTATGTTT | 3480 |
| GTTCCATGTG | GTCTCACCAG | CATGGTGATC | CAGGGTAGGT | AAATTGTTAC | ATGCTGGTTC | 3540 |
| AGGACTCCGA | AGGCACATGT | CCTAAGAGAG | AGAACCAAGT | GGAATCTATA | GTGCGTTGTA | 3600 |
| TAATCTTTTA | GAATTACATA | GTTTCAGTTG | TACCTGTGCA | ATTATTGATA | GAGACAGTTA | 3660 |
| ATCAGTGTGA | GGGAACACAG | ACCCTTGCCC | AGGTCCAAGG | TGAGGGAACC | CTCTGTACCT | 3720 |

| | | | | | | |
|---|---|---|---|---|---|---|
| GTCAGTGGAA | TAATGTTAAT | GTCACATTAT | AAGAAGAGCC | TGACGGGGCT | GGGTAGAGTG | 3780 |
| GCTCACACCT | GTAATCCCAG | CACTTTGGAA | GACCAAGGCG | GATGGATCAC | TTGAGGCCAG | 3840 |
| GAGTTCAAGA | CCAGCCTGGG | CGACATGACA | AAACCCTGTC | TCGACCAAGA | AAACATAGAA | 3900 |
| TTAGCCAGGT | ATGGTGGCGC | ACTTCTGTAG | TCCCAGCTAC | TTGGGAGACT | GAGGTAGGAG | 3960 |
| GAGTGCTTGA | ACCTGGGAGG | TGGAGGTTTC | AGTGAGCCAA | GATTGCGCCA | CTGCACTCCA | 4020 |
| GCCTGGGTGA | CAGAGCAAGA | TTCCATCTCC | GAGAGAAAAA | AAAAAAAAAA | AAAAAAGAG | 4080 |
| CGTATGAGAT | AGGGTCATCA | TTGAAACTAA | GTTCCCACA | AAAATATAAA | CAACACTTTC | 4140 |
| AATTTAAACA | TACTTTTAAA | AATATTGAAA | TATTTATATG | TAGCTTTTA | ACTGAAAATC | 4200 |
| AATTTTCTTT | TCTTTTACAG | | | | | 4220 |

( 2 ) INFORMATION FOR SEQ ID NO:67:

( i ) SEQUENCE CHARACTERISTICS:
        ( A ) LENGTH: 3507 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:67:

| | | | | | | |
|---|---|---|---|---|---|---|
| GTAACTATGT | TAGAGTTTGA | CAAGTAGAGT | ATGGCTAATG | TAAGCTCATA | AATCATAGTG | 60 |
| ATAGTAAGAA | TTATCTCTGC | TCATCATTTC | CTGAGCATTT | GTACCTGTGG | ACTGGCGAAA | 120 |
| TTAGATGCTA | AAACTAGCAT | CTAATGATTT | TCCTCCTCTA | TATCACAGTT | AATATCCATT | 180 |
| ATATTTACT | TCTTTGGTGA | AAATATTTAA | ATTTTAATGT | TTTAGGCACT | TGTATGGCAG | 240 |
| AATTTATTTT | TAAAGTTTAG | GACATTGTGT | AATATTGGGA | GAAATGAAGG | ATATTGAGAA | 300 |
| ACTTTAGGAG | ATACTCCAAG | TTGAAAAGGT | AAATAAAATA | TTATTTGCTA | TTATACTTAG | 360 |
| CAAATATGTG | CACAGGACTT | GTGGTCTTAA | TATAAATGGA | ACATGTAAGT | ATTTCTCAGT | 420 |
| TTCCTGTTTG | GAGGATAAAT | GACATGATTA | TAATCCATTT | TAGAAAGGGT | CAAATATGTT | 480 |
| TAAAAGAAGA | GGCAGAAATT | GCTTTATCTG | TTGTGTAATT | AAATTGATTA | CATTTATTTT | 540 |
| TTGTGCCTTT | TAGGTGAATT | TTCTTACATG | GCTTATTAAA | GATAAGTGGA | AAAATGATGT | 600 |
| TTAGCATTTT | GGGGAAATT | ACCACTGTCA | AAATTTATGG | AGTTAATGGT | TAAAAAATCA | 660 |
| CTTACTAAAT | AAAAAAATTA | ACTGGGTGTG | GTTGTGCATA | CCTGCAGGCC | TAGCTACTTG | 720 |
| GGAGGCTGAG | ATGGGAGGAT | CACTTGAGCC | CTGAATGATG | GAGCAGCACT | GCACTCCAGC | 780 |
| CTGGGCCACA | GAGCAAGACC | TTGTCTCCAA | AAAAAAAAA | AAAAAGAAG | GTTACTATTA | 840 |
| AATAATTAG | CAGGCTGGGG | GCGGTGGCTC | ACACTTGTAA | TCCCAGTAAT | CCCAGCACTT | 900 |
| TGGAGGCCAA | GGTGTGTGGA | TCACTTGAGG | TCAAGAATTG | GAGATCAGCC | TGGCCAATAT | 960 |
| GGTGAAACCC | CGTCTCAACT | AAAAATACAA | AAATTAGCCG | AGTGTGGTGA | CATGCGCCTG | 1020 |
| TAATCTTAGC | TACTCAGGAA | GCTGAGTCAG | GAAAATCACT | TGAGCCCAGG | AGGCACAGGT | 1080 |
| TGCAGTGAGC | ACTATTGCAC | TCCAGCCTGG | GTGACAAGAG | CGAGACTCCA | TCTCAAAACA | 1140 |
| AATAAATAAA | ATAAAATAAT | TCACAATGTC | ATGTTTTAGC | TGACATTGTG | AATTTTAGTA | 1200 |
| ATCTTTTTTT | AACCTTTAAC | TCCATCCTGA | GTTACATTGA | CCAAAGAAAT | CAGTATCTAG | 1260 |
| AATTATATCA | GGGAACTACT | AACAGGGTTA | ATAAAATGAA | TAAAGAACAT | GACTTCACAA | 1320 |
| AGGTTATAAT | TCACATAGCT | AATAGATACA | GGAAGAGATA | TTCACTGTCA | CTAATAAAGA | 1380 |
| CTTTCAAAGT | AGAAAGATAA | CATTTCATTC | TGTTTTTTTT | GAGATGGAGT | CTTGCTGTTT | 1440 |
| CACCCAGGCC | AGGGTGCAGG | GGCGTGATCT | CAGCTCATTG | CAGCGTGTGC | GTCCCAGGTT | 1500 |

| | | | | | | |
|---|---|---|---|---|---|---|
| CAAATGATTC | TCCCGCTGTG | GCCTCCCAAG | TAGCTGGGAT | TACAGATGCG | CACCACCACA | 1560 |
| CCTGGCTAAT | TTTTTGTATT | TTTAGTAGAG | ACGGGTTTCA | CCATGTTGGC | CAGGCTGGTT | 1620 |
| TCCAACTCCT | GACCTCAGGT | GATCCACCCG | CCTTGGACTC | CCAAAGTGCT | GGCATTACAG | 1680 |
| GTGTGAGCCA | CCATGCCTGG | CCAACATTTT | ATTCTTATCA | TTGGGAAAAT | TTGAAGTCTG | 1740 |
| GTATACCAAG | TTTGGTCACT | GTACAGGGAA | ACAGGAACTC | TATTTTTTTT | ATTTTTCAGT | 1800 |
| TCTTTTTTTT | TTTTTTTTT | TTTTTTGAG | ATGGAGTCTC | ACTCTGCTGC | CCAGGCTGGA | 1860 |
| GTGCAGTAGC | TCAATCTCTA | CTCACTGCAA | CCTCCACTTC | CCAGGTTCAG | GTGATTCTCA | 1920 |
| TGCTTCAGCC | TCCCGGAGTA | GCTGGGATAA | AGGCACATAC | CACTATACCT | GACTAATTTT | 1980 |
| TGTATTTTTT | GTGGAGACCA | GGTTTCACCG | TGTTGACCAG | GCTAGTCTCG | AACTCCTGAC | 2040 |
| CTCAAGTGAT | CTACCTGCCT | CGGTCTCCCA | AAGTGCTGGG | ATTACAGGCA | TGAGCCACTG | 2100 |
| CGCTCAGGCA | GGAACTCTAT | ATTGCTGGTG | TACATTGGTG | AGAGTCAAAA | TTGACACAAC | 2160 |
| TACTTTACTA | GCAAATTTGG | TGGTATTTAG | TAATATTGAA | GGTGCACATT | CTCTTACTGT | 2220 |
| ACTTCTTGGA | GTAGTCCCCA | AAGAAACTCC | TGCACACATG | TATAAGGATG | TTTTCATTAC | 2280 |
| AACATGTTTT | GTTATCATGG | AATATTAGAA | ACAACCTAAA | TTTCCATTGG | TTGGGGAGTG | 2340 |
| AATGCAAAAA | GTCATTGTAT | GTTCATATGA | AAGAATGTTT | TTAGCAATTA | AAATGAATAT | 2400 |
| ATCTTACATA | TCAACATTAA | TGTCAGAAAC | ATTATTGAGT | GTGAAAAGC | AAGTTGCAGA | 2460 |
| ATACCACTGA | AGTATGATAG | CATTTATATA | AAATGTAAAA | ACACGTAATA | AGATATTGCT | 2520 |
| TATTGTTTAC | ACATACATGT | GTATGTGTAG | TAAGTGTGAA | AACATAGGAA | GGATTAAGAC | 2580 |
| CAACTTTGGA | ATGGTTTTA | TCTTTGGGGT | AGAAGGGTAA | GGATGGGATT | AGGGAGGAGT | 2640 |
| ATAAAATGGT | AATTTTGACT | GTTTCTTTTT | CTTTTTCTTT | TTCTTTTTTG | AGACAGAGTC | 2700 |
| TCGCATTGTC | GCCAGGCTGG | AGTGCAGTGG | CGTGATCTCG | GCTCACTGCA | ACCTCCGCCT | 2760 |
| CCCAGGTTTA | AGTGATTTTC | CTGCCTCAGC | CTCCTGAGTA | GCTGGGATTA | CAGGTGCCCG | 2820 |
| CCACCACGCC | CAGCTAATTT | TTTGTATTTT | TAGTAGAGAT | CGGGTTTTAC | CATGTTGGCC | 2880 |
| ATGCTGGTTT | CAAACTCCTG | ACCTTGTGAA | TCTCCCACCT | CGGCCTCCCA | AAGTGCTGGG | 2940 |
| ATTACAGGTG | TGAGCTACTG | CGCCTAGCCT | TGACTGCTTT | TATAGTGTTG | CTAGTTTAAA | 3000 |
| AAAAAATCTG | AAGTGGCAGG | AGGAGGTGGC | TCACACCTGT | AATCACAGTG | TTCTAGGAAG | 3060 |
| CCAAAGTAGG | AGGATCACTC | AAGCCCAGGA | GTCTGCGGTG | AGCTGTGATC | TTGCCACTGA | 3120 |
| ACTCCAACAT | GGGTGATAGA | ACGAAACCCT | ATCTCTTACA | AAAACAAAAA | CGACAAAATT | 3180 |
| TATTTAATAT | ATTAACATTT | AAAAAATCTG | GCAGTGAACC | AACGTGAATG | TTGGTTAGGT | 3240 |
| TACTCTTGTT | AATTTTGGTT | TGTATTTTCA | AATATTTCAT | AGTTAACAAA | TACTTTAGGT | 3300 |
| AACCTAAACA | AAATGGATTA | GGAGGATCAG | AGGAATATAC | CAATCTGTAA | GAAATTAAGC | 3360 |
| TAGTCAGAGA | CATGAGTTGT | GATTTATTT | CACTGTCTAA | AAGTAATATA | ATTTAATGCG | 3420 |
| ATAATATTGA | TTTACTTTTG | AATACTTACT | TTTGTATACT | TTAGCCTTAT | GTTAATTATG | 3480 |
| AAATATCTTG | TTTGTCTTTA | ATACCAG | | | | 3507 |

( 2 ) INFORMATION FOR SEQ ID NO:68:

( i ) SEQUENCE CHARACTERISTICS:
        ( A ) LENGTH: 9837 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:68:

| | | | | | | |
|---|---|---|---|---|---|---|
| GTGAGCCTAA | CATCAATCTT | GGCCTTTACT | AACCTCAAAA | TGCTTCAGAT | GCTAGAAACA | 60 |
| GGGTTTGTGC | TAAGCTTAGG | CACTCATTAG | AGTGATGAGA | GCTGCCAGGG | AGCAGTGATC | 120 |
| AGTCAGTCCT | CATGAAGCAA | AACCCAGGGT | TGTTTTGTTT | TTTGCCTTTT | TTGAGGGGA | 180 |
| GGGGGTGGAA | TTTAAGGGTG | GGAAACAGGG | CAAGGGATTT | TGATTCTTTT | TATTCCCTCT | 240 |
| CCTATTTGTA | CATTTTGGTG | TAAACCTGAA | ATTGATTTCT | TACCAAAGGC | CTGTTTCTGG | 300 |
| GACAGGCAGT | GTCCTCAGGA | GTCTGGCTAA | TGGGAGAAGT | TGACATTTTT | GACATTGCAG | 360 |
| TTCAATAGTC | ATATTAGCAC | AGATGTATGT | GGCAACAGCC | ACCTCATTCT | AAGAAGGGGA | 420 |
| AGGAAGCTTG | AGTCAGGCCT | TAATGTTGAA | AAGTCAGGGA | GCTGTTGAGG | TATGGAAGGG | 480 |
| CACTCAGCAG | GAAGCAGGTT | AAGGGGAAGA | AAACAGTGTC | CTTGAGGCAG | ACAGTGATTC | 540 |
| AAAGCTTAAT | TACGGGCATC | ATGCTATGTT | AGCGAGTGGA | ACTGGATTGT | GACGGCCCTT | 600 |
| ACATAATGAG | ATTTTTATTG | ATAAAGGTTG | CTTAGAGGCT | GGGCGTTGTG | GCTCACACCT | 660 |
| GTACTCCCAA | CACTTTGGGA | GGCCACAGTG | GGCAGATCAC | CTGAGGTCAG | GAGTTCATGA | 720 |
| CCAGGCTAGT | CAACACGGTG | TAAACCTCAT | CTCTATTAAA | AATACAAAAA | TTAGCTGGGT | 780 |
| GTGGTGGAAT | GCACCTGTAA | TCCCAGCTAC | TCGGGAGGCT | AAGGCAGGAA | AATAGCTTGA | 840 |
| ACCCAGGAGG | TGGAGGTTGC | AGTGAGCAGA | GCATTGCGCC | ATTGCACTCC | AGCCTGGGTG | 900 |
| ACAAAGCGA | AACTCACTGT | CTCAAAAAAA | AAAAAAACC | GGTTGCTTAG | AAATACACAT | 960 |
| TTTTTTTTGG | CCTGAACTCT | TCAAAAAAAG | GTCAGTATGG | TAAGAGGACG | GGAAGGTTT | 1020 |
| CGTAGAGGAG | ACTAGGGAGA | CACGACATCC | AAATGCAATG | CATGATTCTT | GACCCTGCAT | 1080 |
| AGGAAATCGT | CGTTATAAAG | GACATTTGA | GGAAAATTTG | AATGTGGGCT | TTAGTGTATT | 1140 |
| TTTTTTTTA | AAGTTTCTTT | GGTGTTGATG | ATGTCTAGCA | GATTATGTAG | GAGACTGTGC | 1200 |
| TGAAAAGTAT | TCAGAGGTAA | AGTGTCCAG | TGTCTGCAGC | TTACTTCAA | ACGGGTTGGT | 1260 |
| TGCAATATAT | TTAGGTAGGG | AGAGAGTGAA | AGTAACTCTT | AGACATTAAT | GATTGATAAG | 1320 |
| TGGCTGTTCA | GTGTACTATT | TTTTTCAACT | CTTTGTAGGC | TTGCAATCTT | TTAAAAAGTT | 1380 |
| GAGGAAAACA | GTCCGGGTGC | AGTGCCTCAC | GCCTGTAATC | CCAACATTTT | GGCAGGCTGG | 1440 |
| GATGGGAAAA | TTGCTTGAGG | CCAGAATTTG | GAAAACGGCT | CAGGCAACAT | AAAACCCCAT | 1500 |
| CCCTACAACA | AATAAAAATT | AGCTGAGCAT | GGTGCCATGC | ACCTGTAGTT | GTATCTACTC | 1560 |
| AGGAGGCTGA | GCCCAAAATT | TCAAGGCTGC | GGTGAGCTAT | GGTCGTGCCA | CCACACTCCA | 1620 |
| GCCTGGGCAA | TAAATTGAGA | AACCCTGTCT | GTTTGGAAAA | AAAAGTTGAG | GAAAACAATT | 1680 |
| AAACAATAAC | AGCAAAATC | TGTTATAAAA | TGTAATAATG | GCCAGGTGT | GGTGGCTCAT | 1740 |
| GCCTGTAATC | CCACCACTTT | GGGAGGCCGA | AATGGGTGGA | TCACCTGAGG | TCAGGAGTTC | 1800 |
| AAAATCAGCT | TGGCCAACAT | GGTGAAACCC | CATCTCTGCT | AAAATTACAA | AAAATTAGC | 1860 |
| TGGGTGCGGT | GGCGCACACC | TGTAATCCCA | GATACTCAGG | AGGCTGAGGC | AGGAGAATCG | 1920 |
| CTTGAACCCA | GGAGGCGGAG | GTTGCAGTGA | GCCGAGATCG | TGCCACTACA | CTCCAGCCTG | 1980 |
| GGCAACAGAG | CCAGACTCTG | TCTCAAAAAA | AAAAAAAGT | TTAATTCACG | CAGAGCCAGC | 2040 |
| TGAACGGCAG | ACAGGAGTTT | GGTTATTCAA | ATCAGCCTAC | CAGAAAATTC | GGAGACTGGG | 2100 |
| GTTTTTAAAG | AATGACTTGG | CGGGTAGGGG | GCCAGGGATT | GGCGAATGCT | AATTTGTCAG | 2160 |
| GTGGGAGGTG | AAATCACAGG | GGGTTGAAGT | GGGCTCTTGC | TGTCTTCTGT | TACTGAGTGG | 2220 |
| AATTGCAGAA | CTTGTTGAGC | CAGATTATGG | TCTGAGTGGC | GCCAGCTAGT | GCATTGGAAT | 2280 |
| GCGCGGTCTG | AAAAGTATCT | CCAGCACCAA | TCTTAGGTTT | TACAATAGTG | ATGTTATCCC | 2340 |

| | | | | | |
|---|---|---|---|---|---|
| TGAGAGCAAT | TGGGGAGGTC | AGGAATCTTA | TAGCCTCTGG | CTGCAAGCCT | CCTAAATCAT | 2400 |
| AATTTCTAAT | CTTGTGGCTA | ATTTGTTAGT | TCTACAAAGG | CAGACTGATC | CCCAGGCAAG | 2460 |
| AATGGGGTTT | GTTTTGGAA | AGGACTGTTA | CAATCTTTGT | TTCAAAGTGA | AATTAGAAAT | 2520 |
| TAAATTCCTC | CTGTAGTTAG | TTAGGTCTTC | GCCCAGGAAT | GAACAAGGGC | AGCTCGGAAG | 2580 |
| TGAGAAGCGT | GGAGTCATTT | AGGTCAGATC | CCTTGCACTG | TCATAACTTT | CTCACTGTTA | 2640 |
| GGATTTTTGC | AAAGGCAGTT | TCGTGAACGT | ACAGAGACAG | GCCCTTGCTA | TTATCCCTAT | 2700 |
| TTTTAGATA | AGGATATCCA | GGCGATGAGG | AAGTTTACT | TCTGGGAACA | GCCTGGATAC | 2760 |
| GAAACCTTCA | CACGTCAGTG | TCTTTTGGGA | CATTTTCTCG | TCAGTACAGC | CCTGTTGAAT | 2820 |
| GTTCTCACGG | TGGGGAGGTA | CGTGTTTAAA | ATGCGGGGAA | GGTGCTTTTA | TTTCACCCCT | 2880 |
| GGTGAAACTA | GGGGAGCTAA | TTTTTTTAAA | CATGATTTTT | GGCCCCCTTG | AACCGCCGGC | 2940 |
| CTGGACTACG | TTTCCCAGCA | GCCCGTGCTC | AAGACTACGG | GTGCCTGCAG | GCGGTCAGAG | 3000 |
| TCGTTTGCGG | CGGCGCAGGC | GCGGTGCGGG | CGGCGGACGG | GCGGGCGCTT | CGCCGTTTGA | 3060 |
| ATGGCTGCGG | GCCCGGGCCC | TCACCTCACC | TGAGGTCGGC | CGCCCAGGGG | TGCGCTATGC | 3120 |
| CGTCGGGAGG | TGACCAGTCG | CCACCGCCCC | CGCCTCCCCC | TCCGGCGGCG | GCAGCCTCGG | 3180 |
| ATGAGGAGGA | GGAGGACGAC | GGCGAGGCGG | AAGACGCCGC | GCCGCCTGCC | GAGTCGCCCA | 3240 |
| CCCCTCAAAG | CCGAATTCTG | CAGATATCCA | TCACACTGGC | GGCCGCTCGA | GCATGCATCT | 3300 |
| AGAGGGCCCA | ATTCGCCCTA | TAGTGAGTCG | TATTACAATT | CACTGGCCGT | CGTTTTACAA | 3360 |
| CGTCGTGACT | GGGAAAAACC | CTGGCGTTAC | CCAACTTAAT | CGCCTTGCAG | CACATCCCCC | 3420 |
| TTTCGCCAGC | TGGCGTAATA | GCGAAGAGGC | CCGCACCGAT | CGCCCTTCCC | AACAGTTGCG | 3480 |
| CAGCCTGAAT | GGCGAATGGA | CGCGCCCTGT | AGCGGCGCAT | TAAGCGCGGC | GGGTGTGGTG | 3540 |
| TTACGCGAGC | GTGACCGCTA | CACTTGCCAG | CGCCCTAGCG | CCCGCTCCTT | TCGCTTTCTT | 3600 |
| CCCTTCCTTT | CTCGCCACGT | TCGCCGGCTT | TCCCCGTCAA | GCTCTAAATC | GGGGGCTCCC | 3660 |
| TTTAGGGTTC | CGATTTAGTG | CTTTACGGCA | CCTCGACCCC | AAAAAACTTG | ATTAGGGTGA | 3720 |
| TGGTTCACGT | ATTGGGCCAT | CGCCCTGATA | GACGGTTTTT | CGCCCTTTGA | CGTTGGGAGT | 3780 |
| CCACGTTCTT | TAATAGTGGA | CTCTTGTTCC | AAACTGGAAC | AACACTCAAC | CCTATCTCGG | 3840 |
| TCTATTCTTT | TGATTTATAA | GGGATTTTGC | CGATTTCGGC | CTATTGGTTA | AAAAATGAGC | 3900 |
| TGATTTAACA | AAAATTTAAC | GCGAATTTTA | ACAAAATTCA | GGGCGCAAGG | GCTGCTAAAG | 3960 |
| GAAGCGGAAC | ACGTAGAAAG | CCAGTCCGCA | GAAACGGTGC | TGACCCCGGA | TGAATGTCAG | 4020 |
| CTACTGGGCT | ATCTGGACAA | GGGAAAACGC | AAGCGCAAAG | AGAAAGCAGG | TAGCTTGCAG | 4080 |
| TGGGCTTACA | TGGCGATAGC | TAGACTGGGC | GGTTTTATGG | ACAGCAAGCG | AACCGGAATT | 4140 |
| GCCAGCTGGG | GCGCCCTCTG | GTAAGGTTGG | GAAGCCCTGC | AAAGTAAACT | GGATGGCTTT | 4200 |
| CTTGCCGCCA | AGGATCTGAT | GGCGCAGGGG | ATCAAGATCT | GATCAAGAGA | CAGGATGAGG | 4260 |
| ATCGTTTCGC | ATGATTGAAC | AAGATGGATT | GCACGCAGGT | TCTCCGGCCG | CTTGGGTGGA | 4320 |
| GAGGCTATTC | GGCTATGACT | GGGCACAACA | GACAATCGGC | TGCTCTGATG | CCGCCGTGTT | 4380 |
| CCGGCTGTCA | GCGCAGGGGC | GCCCGGTTCT | TTTTGTCAAG | ACCGACCTGT | CCGGTGCCCT | 4440 |
| GAATGAACTG | CAGGACGAGG | CAGCGCGGCT | ATCGTGGCTG | GCCACGACGG | GCGTTCCTTG | 4500 |
| CGCAGCTGTG | CTCGACGTTG | TCACTGAAGC | GGGAAGGGAC | TGGCTGCTAT | TGGGCGAAGT | 4560 |
| GCCGGGGCAG | GATCTCCTGT | CATCCCACCT | TGCTCCTGCC | GAGAAAGTAT | CCATCATGGC | 4620 |
| TGATGCAATG | CGGCGGCTGC | ATACGCTTGA | TCCGGCTACC | TGCCCATTCG | ACCACCAAGC | 4680 |
| GAAACATCGC | ATCGAGCGAG | CACGTACTCG | GATGGAAGCC | GGTCTTGTCG | ATCAGGATGA | 4740 |

-continued

| | | | | | | |
|---|---|---|---|---|---|---|
| TCTGGACGAA | GAGCATCAGG | GGCTCGCGCC | AGCCGAAACT | GTTCGCCAGG | CTCAAGGCGC | 4800 |
| GCATGCCCGA | CGGCGAAGGA | TCTCGTCGTG | ACCCATGGCG | AATGCCTGCT | TGCCGAATAT | 4860 |
| CATGGGTGGA | AAAATGGCCG | CTTTTCTGGG | ATTCATCGAA | CTGGTGGCCG | GGCTGGGTGT | 4920 |
| GGCGGACGCT | ATCAGGACAT | AGCGTTGGCT | ACCCGTGATA | TTGCTGAAGA | GCTTGGCGGC | 4980 |
| GAATGGGCTG | ACCGCTTCCT | CGTGCTTTAC | GGTATCGCCG | CTCCCGATTC | GCAGCGCATC | 5040 |
| GCCTTCTATC | GCCTTCTTGA | CGAGTTCTTC | TGAATTGAAA | AAGGAAGAGT | ATGAGTATTC | 5100 |
| AACATTTCCG | TGTCGCCCTT | ATTCCCTTTT | TTGCGGCATT | TTGCCTTCCT | GTTTTGCTC | 5160 |
| ACCCAGAAAC | GCTGGTGAAA | GTAAAAGATG | CTGAAGATCA | GTTGGGTGCA | CGAGTGGGTT | 5220 |
| ACATCGAACT | GGATCTCAAC | AGCGGTAAGA | TCCTTGAGAG | TTTTCGCCCC | GAAGAACGTT | 5280 |
| TTCCAATGAT | GAGCACTTTT | AAAGTTCTGC | TATGTGGCGC | GGTATTATCC | CGTATTGACG | 5340 |
| CCGGGCAAGA | GCAACTCGGT | CGCCGCATAC | ACTATTCTCA | GAATGACTTG | GTTGAGTACT | 5400 |
| CACCAGTCAC | AGAAAAGCA | TCTTACGGAT | GGCATGACAG | TAAGAAGAAT | TATGCAGTGC | 5460 |
| TGCCATAACC | ATGAGTGATA | ACACTGCGGC | CAACTTACTT | CTGACAACGA | TCGGAGGACC | 5520 |
| GAAGGAGCTA | ACCGCTTTTT | TGCACAACAT | GGGGGATCAT | GTAACTCGCC | TTGATCGTTG | 5580 |
| GGAACCGGAG | CTGAATGAAG | CCATACCAAA | CGACGAGCGT | GACACCACGA | TGCCTGTAGC | 5640 |
| AATGGCAACA | ACGTTGCGCA | AACTATTAAC | TGGCGAACTA | CTTACTCTAG | CTTCCCGGCA | 5700 |
| ACAATTAATA | GACTGGATGG | AGGCGGATAA | AGTTGCAGGA | CCACTTCTGC | GCTCGGCCCT | 5760 |
| TCCGGCTGGC | TGGTTTATTG | CTGATAAATC | TGGAGCCGGT | GAGCGTGGGT | CTCGCGGTAT | 5820 |
| CATTGCAGCA | CTGGGGCCAG | ATGGTAAGCC | CTCCCGTATC | GTAGTTATCT | ACACCGACGG | 5880 |
| GGAGTCAGGC | AACTATGGAT | GAACGAAATA | GACAGATCGC | TGAGATAGGT | GCCTCACTGA | 5940 |
| TTAAGCATTG | GTAACTGTCA | GACCAAGTTT | ACTCATATAT | ACTTTAGATT | GATTTAAAAC | 6000 |
| TTCATTTTTA | ATTTAAAAGG | ATCTAGGTGA | AGATCCTTTT | TGATAATCTC | ATGACCAAAA | 6060 |
| TCCCTTAACG | TGAGTATTCG | TTCCACTGCA | GCGTCAGACC | CCGTAGAAAA | GATCAAAGGA | 6120 |
| TCTTCTTGAG | ATCCTTTTTT | TCTGCGCGTA | ATCTGCTGCT | TGCAAACAAA | AAAACCACCG | 6180 |
| CTACCAGCGG | TGGTTTGTTT | GCCGGATCAA | GAGCTACCAA | CTCTTTTTCC | GAAGGTAACT | 6240 |
| GGCTTCAGCA | GAGCGCAGAT | ACCAAATACT | GTTCTTCTAG | TGTAGCCGTA | CGTAGGCCAC | 6300 |
| CACTTCAAGA | ACCTCTGTAC | CACCGCCTAC | ATACCTCGCT | CTGCTAATCC | TGTTACCAGT | 6360 |
| GGCTGCCGCC | AGTGGCGATA | AGTCGTGTCT | TACCGGGTTG | GACTCAAGAC | GATAGTTACC | 6420 |
| GGATAAGGCG | CAGCGGTCGG | GCTGAACGGG | GGGTTCGTGC | ACACAGCCCA | GCTTGGAGCG | 6480 |
| AACGACCTAC | ACCGAACTGA | GATACCTACA | GCGTGAGCTA | TGAGAAAGCG | CCACGCTTCC | 6540 |
| CGAAGGGAGA | AAGGCGGACA | GGTATCCGGT | AAGCGGCAGG | GTCGGAACAG | GAGAGCGCAC | 6600 |
| GAGGGAGCTT | CCAGGGGGAA | ACGCCTGGTA | TCTTTATAGT | CCTGTCGGGT | TTCGCCACCT | 6660 |
| CTGACTTGAG | CGTCGATTTT | TGTGATGCTC | GTCAGGGGGG | CGGAGCCTAT | GGAAAAACGC | 6720 |
| CAGCAACGCG | GCCTTTTTAC | GGTTCCTGGC | CTTTTGCTGG | CCTTTTGCTC | ACATGTTCTT | 6780 |
| TCCTGCGTTA | TCCCCTGATT | CTGTGGATAA | CCGTATTACC | GCCTTTGAGT | GAGCTGATAC | 6840 |
| CGCTCGCCGC | AGCCGAACGA | CCGAGCGCAG | CGAGTCAGTG | AGCGAGGAAG | CGGAAGAGCG | 6900 |
| CCCAATACGC | AAACCGCCTC | TCCCCGCGCG | TTGGCCGATT | CATTAATGCA | GCTGGCACGA | 6960 |
| CAGGTTTCCC | GACTGGAAAG | CGGGCAGTGA | GCGCAACGCA | ATTAATGTGA | GTTAGCTCAC | 7020 |
| TCATTAGGCA | CCCAGGCTTT | ACACTTTATG | CTTCCGGCTC | GTATGTTGTG | TGGAATTGTG | 7080 |
| AGCGGATAAC | AATTTCACAC | AGGAAACAGC | TATGACCATG | ATTACGCCAA | GCTATTTAGG | 7140 |

```
TGACACTATA GAATACTCAA GCTATGCATC AAGCTTGGTA CCGAGCTCGG ATCCACTAGT   7200
AACGGCCGCC AGTGTGCTGG AATTCGGCTT AAAGGTAGGC GGATCTGGGT CGACTCTAGG   7260
CCTAAATGGC CATTTAGGTG ACACTATAGA AGAGCTCGAG GACAACAGAA AATCTTAGTG   7320
AACATGTTTT ATGGGAAAAT TTTATATACA ACATCAAAAG CACAATCCGT AAAATACTGT   7380
TAAAATGGAT TTTATCAAAA TGAATAATTT CTGCTATTTG AGACACTGTT AAGAGAATTA   7440
AAAACCAGC CATAGACTAT TAGAAAATCT GTACACGTTC CATATCTGAT GAAGCATTTG   7500
TATATCTACA GTATCTAAAG AATTCTCAAA ATTCAGTAGG AAAACCACCA AATGTAAAAG   7560
TGGGCAAAAG ATTTGAACAC ACTTCACCCA TTACATGCCT GTTAGAATGG CTAAAATCCA   7620
AAAAGTGACA AATCGTAAGT TCTGACAACA ATGTGGAACA ATTTTACATA TTGCTGGTGT   7680
GAACGCAAAA TGGCATCGCC ACTGTGGAAA GTTGTTTCTT AAACATACCA TTATACAACC   7740
AGCAATCTCA TTCCTAGGTA TTTACACAAA TGAAATGGAA ACTTATGTTT AGACAAAATC   7800
ACGTACATGA CTGTTTATAG TGACTTTCTT CCTAATTGCC AAAAGTGGG AAACAACCCA   7860
AACGTCCTTC AGCTGGTGAA TGCATATAAA TAAGCTGTGG TGCATCCAGA CAATCGACTG   7920
CTACTTTGCA ATAAAAAGGA ACTGATATAT TCAATGTAGA TAAATCTCAA ATGCATCAAT   7980
GCTTAAGTGA AAGACACTGG ATTCAGTAGG CTACTTATGA TTCCATTTCT GTGACATTGT   8040
GGAAAAGGCA AAACTATTGG ACAAGAACAT CAGTGGTGGT TTGGGATAGG CTGACAAGGG   8100
AGTATGAGGG ATTTTTTCAG AGGAACAGTT TTATCCGACT GTAGGTATTT CTAGCACAGA   8160
ATTGGGAGTC TGTCCAGTAA AATGATAGCG ATTATTAGAC TCTTGGTTGG AGAAAGATTT   8220
GTCATCTTGA CGTAATAGGT GATAGCTGAA ACTTACGGGG AGAATATTAC AAAGCAAGGA   8280
GGGGGAGAAT ATTCCCAAGC AAGAAGTAGC TTATGTCTAG AACCAATCTA TAACGTACTA   8340
ACATTTAGAC TACTATGAGG GGATAATTAT CAAATACTAT ACAAGATCAG TTAAGATGAA   8400
GACTGATCAT TAGTGATACT TGACAGAGCA GTGTCAGTGC ACTGGTATGA CTTGTTGAGA   8460
AATAAATTAT GGTAGCATTG CTTATACACA ATTAACGATG TATACAGTAA GACAGTGTGA   8520
GAAATATTCA AGCAAATGGG AGACCGCAGA GATACCAAAT GCAGACCAGA CTCTTAGGAG   8580
GCAAGAAGGG GGCTAGAAAA AGAATTGAAG GAAAGCTTTC TTCAGATGCT TAAGATTTTG   8640
TGGCCAGGTG CAGTGGCTCA TGCCTGTTCC CAGCACATTA GGAGGCCCAA AGCAGGAGGA   8700
TTGCTTGAGC CCAGGAATTC AAGACCAGCT TGGACAACAT AGTGCAACCC CATTTCTATT   8760
GGTAATTAAA AAAAAAAAAA AATGAAAAAC ACTTGTGAAG GTACATCTGT TGATAATAAA   8820
GAACACTGAT TTTCATTAAA ACCCCCAAAA CATTTATTAC TTTAAAGAAT AAAAATAACA   8880
AGTGTCATGA TAAAATATGT CTGGGATTTG TTTTAAAATA ATCTGGGGAA TGGAAGTGAA   8940
TCAGAGTATA AATCAAGCAA GGCTGGCCAA ACATGCTGAA GTAGAGGAAT AGGTATGTGA   9000
GGATGCATTA TGCTTCTCTA CTTTTGTATG TTTACAATTT CCCTATAATA GATATCTGTG   9060
AATTTGCTTA GTATGCTTTC TGTAAGCAAA CATGGATGAA GCAGCACATG AAAAAGAATT   9120
TTAACCAACA AACTAGCAGA AATAATGTGA CAGACGACTT TTAGAGGCTT TGGAGAAACT   9180
GAATGCTAAA GGTGCTGTAC AGCCAGCCCC AGTCTTTCTG ACATTCTGGC AGTGTCTTTC   9240
TCAATTGCAG CTCCTCATCT GAGCCACTGT CCAGAAAATA ATTTGAGTAA CTTTAATCCT   9300
CAATTCTCCC AAGGATAGTA CCATTCTAGA TCTTACTAAT TTATTAGCTA CAATGGATAC   9360
CTTAGGGGGG GATTAAGGCC TACTTTTCTA GTGAAATCCC AGTTGAGAAT GGCTGCTAAA   9420
AACTGAGTAA CATTAGACTG AAAGAAGGGG AATATTGTAT AAAGTTGTAC TTTGAAAAAG   9480
AGAAAAAGAT GTGTCTAAGT GACTATCAGA TAGCAATGTA ATGCTCCCTA ATTGTAAAAA   9540
```

| | | | | | |
|---|---|---|---|---|---|
| AAATCACAAA | TTTGTGAACT | CACGAATTAT | AGACATGTAT | AATTGACCTA | CAGGTCAAGA | 9600
| AGTGCCTGTG | GAAGAGCTTG | TTAAAAATAG | AACTACTCAG | CCCCTTCTCA | AATAGCCATC | 9660
| GGCCTCAGCC | ATCTGGAAAG | TAAAGTTGGC | AGGTTATGTA | ACTTAGTGTT | TCTTTTACTC | 9720
| TGTAGATGTG | TTCAAACTCT | TCCAGGTAAA | CTGCTTAACT | CATTTGAGAT | TCTTTGACTA | 9780
| ATACTGAGCT | ATGTGCATTT | GCATTTGAA | AAATTATGTA | TCTTTTTCCC | ACCATAG | 9837

( 2 ) INFORMATION FOR SEQ ID NO:69:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:69:

CTCTGTAACT GCTTATAATC CTG                    23

( 2 ) INFORMATION FOR SEQ ID NO:70:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:70:

CTAGGAAACC TGTACAACTC C                      21

( 2 ) INFORMATION FOR SEQ ID NO:71:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:71:

GGCTTATTGT GTGCTGATAT C                      21

( 2 ) INFORMATION FOR SEQ ID NO:72:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:72:

AGAGATCCTT AAGTCGTCAT G                      21

( 2 ) INFORMATION FOR SEQ ID NO:73:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:73:

CAGTTTCTGT GAGAGAGTAC A 21

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:74:

GGCTTACCTG CTCCTGTATT T 21

( 2 ) INFORMATION FOR SEQ ID NO:75:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:75:

GAGGAGGAAT GGGCCTTTAT T 21

( 2 ) INFORMATION FOR SEQ ID NO:76:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:76:

AACCCACAGA ATAGGGCAGG A 21

( 2 ) INFORMATION FOR SEQ ID NO:77:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:77:

GGATACTGGC ATTCTGTGTA AC 22

( 2 ) INFORMATION FOR SEQ ID NO:78:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:78:

ATTTCCAGAT AGTAAGCCCC A 21

( 2 ) INFORMATION FOR SEQ ID NO:79:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:79:

AGCTTGGACG GAAGTCAGAT C        21

( 2 ) INFORMATION FOR SEQ ID NO:80:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:80:

TCTAGCCAAA CCTCGGGTAA C        21

( 2 ) INFORMATION FOR SEQ ID NO:81:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:81:

AATTGTAAAC CTCTGCCC        18

( 2 ) INFORMATION FOR SEQ ID NO:82:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:82:

ATTTCCCAAG CTCATGCT        18

( 2 ) INFORMATION FOR SEQ ID NO:83:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:83:

AGCATGAGCT TGGGAAAT        18

( 2 ) INFORMATION FOR SEQ ID NO:84:

( i ) SEQUENCE CHARACTERISTICS:
        ( A ) LENGTH: 18 base pairs (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:84:

TGAAGACCTA TCTTTGCC                                                                18

(2) INFORMATION FOR SEQ ID NO:85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:85:

GTTCACAGAG CTCCTCACAC T                                                            21

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:86:

AGGCCACAGA GTCAACTATG G                                                            21

(2) INFORMATION FOR SEQ ID NO:87:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:87:

AGGTCCTATC ACCAAGGGTG T                                                            21

(2) INFORMATION FOR SEQ ID NO:88:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:88:

GCTTAGTTAC TTCTTCAAGG C                                                            21

(2) INFORMATION FOR SEQ ID NO:89:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid ( x i ) SEQUENCE DESCRIPTION: SEQ ID NO:89:

GTAGCTGTTC CCTTTCTCCT A 21

( 2 ) INFORMATION FOR SEQ ID NO:90:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:90:

CCTCAACACT CATGAGAGTG A 21

( 2 ) INFORMATION FOR SEQ ID NO:91:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:91:

TGGTTTAGCA CACCTCTTCA C 21

( 2 ) INFORMATION FOR SEQ ID NO:92:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:92:

GCTTAGCACA AACCCTGTTT C 21

( 2 ) INFORMATION FOR SEQ ID NO:93:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:93:

TTCGCCGTTT GAATTGCTGC 20

( 2 ) INFORMATION FOR SEQ ID NO:94:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:94:

ACCGGTTCAC ACCAACTAGG 20

( 2 ) INFORMATION FOR SEQ ID NO:95:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:95:

GAGATAGGGT CATCATTGAA AC      22

( 2 ) INFORMATION FOR SEQ ID NO:96:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:96:

CATTAGCCAT ACTCTACTTG T      21

( 2 ) INFORMATION FOR SEQ ID NO:97:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:97:

GCTAATTTAA CTCTGTAACT GC      22

( 2 ) INFORMATION FOR SEQ ID NO:98:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:98:

CACTGCAGCA CAGACTAATG TGT      23

( 2 ) INFORMATION FOR SEQ ID NO:99:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:99:

TCTCTCCCTT TAACTGTGGG TTT      23

( 2 ) INFORMATION FOR SEQ ID NO:100:

( i ) SEQUENCE CHARACTERISTICS:
        ( A ) LENGTH: 23 base pairs (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:100:

GGAGTTGACG AGATTAATAC CTG            23

(2) INFORMATION FOR SEQ ID NO:101:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:101:

CATGACGACT TAAGGATCTC TT            22

(2) INFORMATION FOR SEQ ID NO:102:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:102:

CTCAGTTTCC AGAGTACAAA C            21

(2) INFORMATION FOR SEQ ID NO:103:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:103:

GTGAATTAAA GTCTTTCTGG CC            22

(2) INFORMATION FOR SEQ ID NO:104:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:104:

ATCTTAGAAA GCAGACAGGG C            21

(2) INFORMATION FOR SEQ ID NO:105:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid ( x i ) SEQUENCE DESCRIPTION: SEQ ID NO:105:

GAGACATTTT ATCCCCTTGT G 21

( 2 ) INFORMATION FOR SEQ ID NO:106:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:106:

TCCATGCCTC CAGTCTAAAG T 21

( 2 ) INFORMATION FOR SEQ ID NO:107:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:107:

CACTTAAGTT GCACTGGGTA 20

( 2 ) INFORMATION FOR SEQ ID NO:108:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:108:

CAACAGGAAG TTGGTCTCAT C 21

( 2 ) INFORMATION FOR SEQ ID NO:109:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:109:

TAAAAGGAAG AGCGGCTGTT T 21

( 2 ) INFORMATION FOR SEQ ID NO:110:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:110:

TTAAACCTAA CTGCCACCCT C 21

( 2 ) INFORMATION FOR SEQ ID NO:111:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:111:

| CTGAGCTATG | TGCATTTGCA | | | | | 20 |

( 2 ) INFORMATION FOR SEQ ID NO:112:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:112:

| AAGGCTGCTG | CTAAACAGAT | | | | | 20 |

( 2 ) INFORMATION FOR SEQ ID NO:113:

( i ) SEQUENCE CHARACTERISTICS:
        ( A ) LENGTH: 2461 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:113:

| TGCCCGCCTT | GGCCTCCCAA | CGTGTAGGGA | TTACAGGCGT | GAGTCACCGC | GCCTTGCCAA | 60 |
|---|---|---|---|---|---|---|
| ATTATTTATT | ATTATTTTTT | GGAGACAGGG | TCTCTGTTGC | CCAAGCTGTA | GTGGTATGGC | 120 |
| CACAGTTCAC | TGCAGACTCC | CCAGGATTAG | GCGTTCCTCC | CACCTCAGTC | TCCCAAGTAG | 180 |
| CTAGGATTAC | AGGCGTCTAC | CACCACTCTG | GGTTAATTTT | TCTATTTTTT | GGAGAGACAG | 240 |
| GGTTTCACTA | TGTCGCCCAG | GCTGGACCTC | GAACTCCTGT | CTCAAGCAGC | CCCCCCACCT | 300 |
| CGCCTCCCAA | AGTGCTGGAT | TTACAGGTGT | GATCCACAAC | GTCCAGCCTA | TATACTTAAG | 360 |
| ATACTTCTAA | ACCATTTGTG | TTCAACTTCT | GTTCTTGCCC | CATAGTCACC | TTGAGACTCA | 420 |
| TCACTTAGCC | AACTCCAAAA | GCATTGCTGA | TTACTGTGAA | TTTTACTAAG | GTTTTCTTAA | 480 |
| GAGGGTTCCA | TTGTCTCAAA | ATTGTTCCTG | AAATATCCTG | TTACCTGTCT | ACCTGATTTT | 540 |
| CTCCTATCTT | CAGAGTTCCA | TTTCCTGTCC | TCCCGCCTGT | CATTATACCT | TCCATAAGCC | 600 |
| CCTACTTTTG | TCCCAGCACT | TTTCCCTCTG | TCAGTTTACA | TATCCCACCA | AGCAAAACAA | 660 |
| AAATAGCAAA | ACAGTAATGC | CTTCTGAATC | CTCAAATTGC | TCAATCCTCA | GATTGCTCCT | 720 |
| CAATCTGGAA | AATGTTTTAT | ATCAAGCCCA | TTTATAAATC | AAGGATTGGC | AATTTAAAAA | 780 |
| ATTAAAATAA | AGAAAGGAGA | ATTGGAAATA | AAATGAATTG | GCTGGGCACG | GTGGCTCACG | 840 |
| CCTGTAATCC | CAGAACTTTG | GGAGGCCGAG | GTGGGTGGAT | CACTTGAGGT | CAGGAGTGCG | 900 |
| AGACCAGCCT | GGCCAACATG | GTGAAACCCT | GCCTGTTCTG | AAAATCCAAA | AATCAGCTGG | 960 |
| GTGCGGCGGC | GCACACCTGT | AATCCCAGAT | ACTCAGGAGG | CTGAGGCAGG | AGAATCGCTT | 1020 |
| GATCCCAGGA | GGCGGAGGTT | GCAGCGAGCC | GAGATCGTGC | CACTACACTC | CAGTCTGGCC | 1080 |
| AACAGAGCCA | GACTCTGTCT | CACAAAAAAA | AAAAGTTTA | ATTCACGGAG | AGCCAGCTGA | 1140 |

| | | | | | | |
|---|---|---|---|---|---|---|
| ACGGCAGACA | GGAGTTTGGT | TATCCAAATC | AGCCTACCAG | AAATTGGAGA | CTGGGGTTTT | 1200 |
| TAAAAGAATG | ACTTGGCGGG | TAGGGGCCCA | GGGATTGGCG | AATGCTAATT | TGTCAGGTGG | 1260 |
| GAGGTGAAAT | CACAGGGGGT | TGAAGTGGGC | TCTTGCTGTC | TTCTGTTACT | GAGTGGAATT | 1320 |
| GCAGAACTTG | TTGAGCCAGA | TTATGGTCTG | AGTGGCGCCA | GCTAGTGCAT | CGGAATGCGC | 1380 |
| GGTCTGAAAA | GTATCTCCAG | CACCAATCTT | AGTTTTACA | ATAGTGATGT | TATCCCTGAG | 1440 |
| AGCAATTGGG | GAGGTCAGGA | ATCTTATAGC | CTCTGGCTGC | AAGCCTCCTA | AATCATAATT | 1500 |
| TCTAATCTTG | TGGCTAATTT | GTTAGTTCTA | CAAAGGCAGA | CTGATCCCCA | GGCAAGAATG | 1560 |
| GGGTTTGTTT | TTGGAAAGGA | CTGTTACAAT | CTTTGTTTCA | AAGTGAAATT | AGAAATTAAA | 1620 |
| TTCCTCCTGT | AGTTAGTTAG | GTCTTCGCCC | AGGAATGAAC | AAGGGCAGCT | CGGAAGTGAG | 1680 |
| AAGCGTGGAG | TCATTTAGGT | CAGATTCCTT | GCACTGTCAT | AACTTTCTCA | CTGTTAGGAT | 1740 |
| TTTTGCAAAG | GCAGTTTCGT | GAACGTACAG | AGACAGGCCC | TTGCTATTAT | CCCTATTTTT | 1800 |
| TAGATAAGGA | TATCCAGCCG | ATGAGGAAGT | TTTACTTCTG | GAACAGCCTG | GATACGAAAC | 1860 |
| CTTCACACGT | CAGTGTCTTT | TGGACATTTT | CTCGTCAGTA | CAGCCCTGTT | GAATGTTCTC | 1920 |
| ACGGTGGGGA | GGTACGTGTT | TAAAATACGG | GGAAGGTGCT | TTTATTTCAC | CCCTGGTGAA | 1980 |
| ACTAGGGGAG | CTAATTTTTT | TAAACATGAT | TTTTGTCCCC | CTTGAACCGC | CGGCCTGGAC | 2040 |
| TACGTTTCCC | AGCAGCCCGT | GCTCAAGACT | ACGGGTGCCT | GCAGGCGGTC | AGCGTCGTTT | 2100 |
| GCGACGGCGC | AGACGCGGTG | CGGGCGGCGG | ACGGGCGGGC | GCTTCGCCGT | TTGAATTGCT | 2160 |
| GCGGGCCCGG | GCCCTCACCT | CACCTGAGGT | CCGGCCGCCC | AGGGGTGCGC | TATGCCGTCG | 2220 |
| GGAGGTGACC | AGTCGCCACC | GCCCCCGCCT | CCCCCTCCGG | CGGCGGCAGC | CTCGGATGAG | 2280 |
| GAGGAGGAGG | ACGACGGCGA | GGCGGAAGAC | GCCGCGCCGT | CTGCCGAGTC | GCCCACCCCT | 2340 |
| CAGATCCAGC | AGCGGTTCGA | CGAGCTGTGC | AGCCGCCTCA | ACATGGACGA | GGCGGCGCGG | 2400 |
| CCCGAGGCCT | GGGACAGCTA | CCGCAGCATG | AGCGAAAGCT | ACACGCTGGA | GGTGCGCTCG | 2460 |
| C | | | | | | 2461 |

( 2 ) INFORMATION FOR SEQ ID NO:114:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:114:

| | | |
|---|---|---|
| ACCTCAGGTG | AGGTGAGGGC | CCGG | 24 |

( 2 ) INFORMATION FOR SEQ ID NO:115:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:115:

| | | |
|---|---|---|
| GTGTGCCATT | TATGTGATGG | CAAAG | 25 |

( 2 ) INFORMATION FOR SEQ ID NO:116:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:116:

GTATACCATT TAGCAGCTGT CCGCC                                              25

METHODS FOR THE DIAGNOSIS AND PROGNOSIS OF CANCER

REFERENCE TO GOVERNMENT GRANT

The invention described herein was supported in part by National Institutes of Health grant RO1 CA60999-01A1. The U.S. government has certain rights in the invention.

CROSS-REFERENCE TO RELATED APPLICATIONS

This application claims the benefit of U.S. Provisional Application No. 60/039,532 filed Mar. 3, 1997, U.S. Provisional Application No. 60/020,196 filed Jun. 21, 1996, and U.S. Provisional Application No. 60/019,372 filed Jun. 5, 1996.

FIELD OF THE INVENTION

The invention relates to methods for the identification of individuals at risk for cancer, and for the detection and evaluation of cancers.

BACKGROUND OF THE INVENTION

A. The Rb Family of Tumor Suppressors

Many types of human cancer are believed to be caused by an imbalance of growth regulators within a cell. A decrease in negative control growth regulators and/or their deactivation can cause a cancerous condition. Alternatively, an increase in positive control growth regulators can also cause a cancerous condition.

Since the identification of the first tumor suppressor gene, much effort in cancer research has been focused on the identification of new tumor suppressor genes and their involvement in human cancer. Many types of human cancers are thought to develop by a loss of heterozygosity of putative tumor suppressor genes not yet identified (Lasko et al., *Annu. Rev. Genetics*, 25, 281–296 (1991)) according to Knudson's "two-hit" hypothesis (Knudson, *Proc. Natl. Acad. Sci. USA*, 68, 820–823 (1971)).

One of the most studied tumor suppressor genes is the retinoblastoma susceptibility gene (Rb), whose gene product (pRb, p105, or pRb/p105) has been shown to play a key role in the regulation of cell division. In interphasic cells, pRb contributes to maintaining the quiescent state of the cell by repressing transcription of genes required for the cell cycle through interaction with transcription factors, such as E2F (Wagner et al., *Nature*, 352, 189–190 (1991); Nevins, *Science*, 258, 424–429 (1992); and Hiebert et al., *Genes Develop.*, 6, 177–185 (1992)). The loss of this activity can induce cell transformation as evidenced by the reversion of the transformed phenotype in pRb cells after replacement of a functional pRb (Huang et al., *Science* 242 1563–1565 (1988); Bookstein et al., *Science*, 247: 712–715 (1990); and Sumegi et al., *Cell Growth Differ.*, 1 247–250 (1990)).

Upon entrance into the cell cycle, pRb seems to be phosphorylated by cell cycle-dependent kinases (Lees et al., *EMBO J.* 10:4279–4290 (1991); Hu et al., *Mol. Cell. Biol.*, 12:971–980 (1992); Hinds et al., *Cell*, 70:993–1006 (1992); and Matsushime et al., *Nature*, 35:295–300)) which is thought to permit its dissociation from transcription factors and, hence, the expression of genes required for progression through the cell cycle.

It has been found that the retinoblastoma protein family includes at least three members. Two other proteins, p107, and the recently cloned pRb2/p130, share regions of homology with pRb/p105, especially in two discontinuous domains which make up the "pocket region". Ewen et al., *Cell* 66: 1155–1164 (1993); Mayol et al., *Oncogene* 8: 1561–2566 (1993); Li et al., *Genes Dev.* 7: 2366–2377 (1993); and Hannon et al., *Genes Dev.* 7: 2378–2391 (1993). The pocket domain is required for binding with several viral transforming oncoproteins (Moran, *Curr. Opin. Genet. Dev.* 3: 63–70 (1993)).

The pRb2/p130 cDNA and putative amino acid sequence are set forth by Li et al. The p107 cDNA and putative amino acid sequence are set forth by Ewen et al. The entire disclosures of Li et al. and Ewen et al. are incorporated herein by reference.

It has been found that pRb2/p130, as well as p107 and pRb, act as negative regulators of cell cycle progression, blocking the cells in the G1 phase (Goodrich et al., *Cell* 67: 293–302 (1991); Zhu et al., *Genes Dev.* 7:1111–1125 (1993); Claudio et al., *Cancer Res.* 54:5556–5560 (1994); and Zhu et al., *EMBO J.* 14:1904–1913 (1995)). However, the three proteins exhibit different growth suppressive properties in selected cell lines, suggesting that although the different members of the retinoblastoma protein family may complement each other, they are not fully functionally redundant (Claudio et al., supra).

The mechanisms by which these three proteins exert their control on cell cycle progression are not fully understood but likely include complex formation and modulation of the activity of several transcription factors (Sang et al., *Mol. Cell. Differ.* 3:1–29 (1995)). The most studied of these complexes is the one with the E2F family of transcription factors. E2F's are heterodimeric transcription factors composed of E2F-like and DP-like subunits that regulate the expression of genes required for progression through $G_0/G_1$ S phase of the cell cycle (Lan Thangue, N. B., *Trends Biochem. Sci.* 19:108–114 (1994)).

The three proteins bind and modulate the activity of distinct E2F/DP1 complexes in different phases of the cell cycle (Sang et al., supra; Chellapan et al., *Cell* 65:1053–1061 (1991); Shirodkar et al., *Cell* 66:157–166 (1992); Cobrinik et al., *Genes Dev.* 7:2392–2404 (1993); Hijmans et al., *Mol. Cell. Biol.* 15:3082–3089 (1995); and Vairo et al., *Genes Dev.* 9:869–881 (1995)). This suggests distinct roles for these related proteins in the regulation of the cell cycle.

It has been demonstrated that the growth suppressive properties of pRb2/p130 are specific for the G1 phase. D-type cyclins, as well as transcription factor E2F-1 and E1A viral oncoproteins, were able to rescue pRb2/p130-mediated G1-growth arrest in tumor cells. This suggests that, like other Rb family proteins, the phosphorylation of pRb2/p130 is controlled by the cell cycle machinery, and that pRb2/p130 may indeed be another key G1-S phase regulator. Claudio et al., *Cancer Res.* 56, 2003–2008 (1996).

The association of pRb with transcription factors, such as E2F, has been shown to occur by interactions at a region known as the "pocket region" (Raychaudhuri et al., *Genes Develop.*, 5 1200–1207 (1991)). Recently, p107 has also been shown to exert such a binding profile (Cao et al., *Nature*, 355 176–179 (1992)). Domains A and B, along with a spacer, are believed to correspond with the "pocket region" in the pRb2/p130 gene described herein. Moreover, mutations have been found in the pocket region for several human cancers where a lack of function for the pRb protein is thought to be involved in the acquisition of the transformed phenotype (Hu et al., *EMBO J.*, 9 1147–1153 (1990); Huang et al., *Mol. Cell. Biol.*, 10: 3761–3769 (1990)).

The Rb, p107, and pRb2/p130 proteins may play a key role in cell cycle regulation in that all three proteins interact with several cyclin/cdk complexes. pRb can be regulated by cyclin/cdk complexes, such as cyclin A/cdk2, cyclin E/cdk2 and cyclin D/cdk4, even if stable interaction between pRb and cyclin A/cdk2 or cyclin A/cdk2 has not been found in vivo (MacLachlan et al., *Eukaryotic Gene Exp.* 5: 127–156 (1995)). On the other hand, both p107 and pRb2/p130 stably interact in vivo with cyclin E/cdk2 and cyclin A/cdk2 complexes (Li et al., supra; Ewen et al., *Science* 255:85–87 (1992); and Faha et al., *Science* 255:87–90 (1992)). These complexes may be responsible for the existence of different phosphorylated forms of pRb, p107 and pRb2/p130 in the various phases of the cell cycle (Chen et al., *Cell* 58:1193–1198 (1989); De Caprio et al., *Proc., Natl. Acad. Sci. USA* 89: 1795–1798 (1992); and Beijersbergen et al., *Genes Dev.* 9:1340–1353 (1993)). In that pRb's functional activities are enhanced by these phosphorylations, it is likely that pRb2/p130 is also affected in the same manner by this post-translational modification. Since pRb2/p130 demonstrates similar, even if not redundant, functional properties to pRb, it is proposed that pRb2/p130 acts, like pRb, as a tumor suppressor gene. It has also been found that pRb2/p130 maps on the long arm of chromosome 16. This finding reinforces the notion of pRb2/p130 as a tumor suppressor gene. Chromosome 16 is a region frequently reported to show loss of heterozygosity (LOH) in several human neoplasias, such as breast, ovarian, hepatocellular and prostatic carcinomas (Yeung et al., *Oncogene* 8:3465–3468 (1993)). Chromosome 16, and specifically pRb2/p130, has also been implicated in a rare human skin disease known as hereditary cylindromatosis (HR). HR has been reported as mapping to loci on chromosome 16q12-q13. In that the pRb2/p130 gene maps to chromosome 16q12-q13, it has been put forth as a likely candidate for the tumor suppressor gene involved with the onset of this disease. Biggs et al., *Nature Genetics* 11:441–443 (December 1995).

There is a need for improved methods for identification of individuals at risk for cancer, and for the detection and evaluation of cancers.

Because the pRb2/p130 gene is a tumor suppressor gene and because it maps to a chromosomal region known to be associated with various carcinomas, there is a need for a method to screen individuals for mutations in this gene. There is also a need to identify sequence polymorphisms in this gene. It is believed that mutations, both within the exon coding sequences and the exon-intron junctions, can occur that will affect pRb2/p130's function. Direct DNA sequence analysis of individual exons taken from genomic DNA extracted from tumors has been used successfully to identify mutations of the p53 gene in ovarian carcinomas and the Rb gene in retinoblastoma tumors. Milner et al., *Cancer Research* 53: 2128–2132 (1993); Yandell et al., *N. E. J. Medicine* 321:1689–1695 (1989). However, direct sequencing of exons is an undesirable approach because it is a time intensive process. An understanding of the genomic structure of the pRb2/p130 gene will enable those skilled in the art to screen a patient's DNA for polymorphisms and sequence mutations in the pRb2/p130 gene. Identification of sequence mutations will also enable the diagnosis of carriers of germline mutations of the pRb2/p130 gene and enable prenatal screening in these cases.

B. Gynecologic Cancers

Gynecologic cancers include cancers of the uterus, ovary, cervix, vagina, vulva, and fallopian tube as well as gestational trophoblastic disease. Cancers of the uterus include endometrial carcinomas and uterine sarcomas.

Endometrial cancer is the most common malignancy of the female genital tract. Although this neoplasm is frequently diagnosed at an early stage (75 percent in stage I), approximately 20 percent of the patients will die of the disease, half of which were diagnosed at stage I (Pettersson, *Annual Report On The Results Of Treatment In Gynecological Cancer*, Radiumhemmet, Stockholm, vol. 22: 65–82; Braly, *Gynecol Oncol* 58: 145–7 (1995)). The ability to identify patients with a more aggressive disease is crucial to planning an adequate treatment for each case. With this purpose in mind, several pathologic tumor features have been considered so far, including histologic type, grade of differentiation, depth of myometrial invasion, lymph nodal metastases and extra-uterine spread (MacMahon, *Gynecol Oncol* 2: 122 (1974); Chambers et al., *Gynecol Oncol* 27: 180–8 (1987)). Unfortunately, none of these factors allows a sufficiently accurate stratification of the patients. Such parameters have also questionable reproducibility.

There is great need for a simple laboratory test which is a consistent predictor of clinical outcome in endometrial cancer. What is needed is a prognostic method which can, at an early disease stage, identify the aggressiveness of an individual patient's disease, before initiation of therapy.

Ovarian cancer is the leading cause of gynecologic cancer death in the United States. Most ovarian malignancies are epithelial carcinomas, with a minority of tumors arising from the germ or stromal cells. In ovarian cancers, the degree of cellular differentiation (histologic grade) is an important independent predictor of both response to treatment and overall survival. Ovarian cancers frequently exhibit chromosomal alterations. The pRb2/p130 gene maps to human chromosome 16q12.2, which is one region that is frequently altered in human ovarian cancers. There is a need for improved methods of grading ovarian tumors. The improved methods would be useful in the diagnosis of disease, in selection of treatment, and as prognostic indicators.

C. Lung Cancer

Lung cancer is the greatest single cause of cancer-related deaths in Western countries. Selecting an appropriate course of therapy for lung cancer requires an accurate determination of the cancer's malignant potential. This determination is typically made by "grading" the tumor. The grading of tumors is typically carried out by examination of the character and appearance of tumor sections by skilled pathologists. A significant problem in the use of histologic criteria when determining the prognosis and types of treatment for lung cancer is the degree of interobserver and intraobserver variability in reading the same specimens. Determinations are necessarily subjective. In addition, there is heterogeneity within the tumor itself in both primary and metastatic sites. It may become necessary to obtain the opinion of several pathologists to reach a consensus on individual tumor grade.

There is a need for a simple laboratory test which is more consistently predicative of the malignant potential of an individual patient's lung tumor than the present subjective pathological analysis of tumor samples.

Detection of latent cancers before the appearance of lung lesions would allow therapeutic intervention at the earliest stages of the disease, thereby maximizing the prospects for a positive therapeutic outcome. It would also be desirable, through a simple genetic test, to identify disease free individuals who are at risk of lung cancer. Such a screening test would be most advantageous for those individuals who, through environmental exposure to carcinogens or through family history of cancer, may be at risk for developing lung cancer.

There is a need for a simple laboratory test which can be used to augment other forms of lung cancer diagnosis and to identify individuals with latent lung cancers. There is also need for a test to screen individuals for a predisposition to lung cancer.

SUMMARY OF THE INVENTION

The present invention relates to the human pRb2/p130 gene and pRb2/p130 protein, and their use as molecular markers in methods for the diagnosis and prognosis of cancer and for prediction of a predisposition to cancer. According to a preferred embodiment of the invention, the cancer is a gynecologic cancer or a non-small cell lung cancer. According to a most preferred embodiment of the invention, the cancer is endometrial carcinoma, ovarian cancer, a squamous cell carcinoma of the lung, or adenocarcinoma of the lung.

It is an object of the invention to provide a method for determining a prognosis in a patient afflicted with cancer comprising determining the expression level of the pRb2/p130 gene in a sample from the patient. A decreased level of pRb2/p130 gene expression in the sample is indicative of an unfavorable prognosis.

Another object of the invention is to provide a method for detecting or identifying a cancerous disease state in a tissue comprising determining the expression level of the pRb2/p130 gene in a sample of the tissue. Evaluation is advantageously conducted by determining the level of pRb2/p130 expression in the sample, and comparing the expression level in the sampled tissue with the pRb2/p130 expression level in normal, non-cancerous tissue. A decreased pRb2/p130 expression level is indicative of the presence of cancer. This method may be used to detect cancer in an individual not otherwise displaying a visible lesion.

A further object of the invention is to provide a method for identifying disease free individuals at risk for cancer, or individuals at risk for the recurrence of cancer following treatment, comprising determining the level of expression of the pRb2/p130 gene in tissue sampled from an individual and comparing the pRb2/p130 expression level in the sampled tissue with a normal pRb2/p130 expression level. A decreased level of pRb2/p130 expression is indicative of the likelihood of disease or disease recurrence. In the case of endometrial cancer, a method is provided for identifying the risk of recurrence following hysterectomy, and for evaluating the need for further treatment such as radiation therapy or chemotherapy.

Another object of the invention is to provide a method for grading a cancer comprising determining the level of expression of the pRb2/p130 gene in a sample of tissue from a patient suffering from cancer. The expression level in the sampled tissue is compared with the expression level in normal tissue. The degree of the decrement in expression level in the cancer sampled tissue as compared to the normal tissue is indicative of the pathological grade of the cancer. A larger decrement indicates a more aggressive disease state.

It is an object of the invention to provide a DNA segment consisting essentially of an intron of the pRb2/p130 gene, or an at least 15 nucleotide segment thereof.

Another object of the invention is to provide an amplification primer of at least 15 nucleotides consisting essentially of a DNA segment having a nucleotide sequence substantially complementary to a segment of a pRb2/p130 intron exclusive of the splice signal dinucleotides of said intron.

A further object of the invention is to provide methods for identifying polymorphisms and mutations in an exon of a human pRb2/p130 gene.

One embodiment of the invention includes a method for amplifying and identifying polymorphisms and mutations in an exon of a human pRb2/p130 gene, which method comprises:

(a) treating, under amplification conditions, a sample of genomic DNA containing the exon with a primer pair comprising a first primer which hybridizes to the promoter region or to an intron upstream of said exon and a second primer which hybridizes to an intron or to the 3'-noncoding region, said treatment producing an amplification product containing said exon;

(b) determining the nucleotide sequence of said amplification product to provide the nucleotide sequence of said exon; and (c) comparing the sequence of said exon obtained in step b to a sequence for the sequence of a corresponding wild type exon.

Each primer of the PCR primer pair consists of an amplification primer of at least 15 nucleotides consisting essentially of a DNA segment from the promoter region, from a pRb2/p130 intron exclusive of the splice signal dinucleotides, or from the 3'-noncoding region.

The amplification primer described above has a nucleotide sequence substantially complementary to the 3'-noncoding region, the promoter region given as SEQ ID NO:113, or an intron having a nucleotide sequence selected from the group consisting of SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, and SEQ ID NO:68.

In a preferred embodiment, the amplification primer as described above has a nucleotide sequence selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, and SEQ ID NO:112.

Another embodiment of the invention includes a method for identifying polymorphisms and mutations in an exon of a human pRb2/p130 gene, which method comprises:

(a) forming a polymerase chain reaction admixture by combining in a polymerase chain reaction buffer, a sample of genomic DNA containing said exon, a primer pair comprising a first primer which hybridizes to the promoter region or to an intron upstream of said exon and a second primer which hybridizes to the 3'-noncoding region or to an intron downstream of said exon, a mixture of one or more deoxynucleotide triphosphates, and a compound capable of radioactively labeling said primer pair, and a DNA polymerase;

(b) subjecting said admixture to a plurality of polymerase chain reaction thermocycles to produce a pRb2/p130 amplification product;

(c) denaturing said pRb2/p130 amplification product;

(d) electrophoretically separating said denatured pRb2/p130 amplification product;

(e) exposing the electrophoretically separated product of step d to a film to produce a photographic image; and (e) comparing the mobility of the bands in said photographic image of said pRb2/p130 amplification product to a electrophoretically separated amplification product for a corresponding wild type exon.

In another embodiment, the invention includes a method for identifying mutations in a human chromosomal sample containing an exon of a human pRb2/p130 gene, which method comprises:

(a) forming an admixture by combining in a buffer, a chromosomal sample containing said exon, a primer pair comprising a first primer which hybridizes to the promoter region or to an intron upstream of said exon and a second primer which hybridizes to the 3'-noncoding region or to an intron downstream of said exon, a mixture of one or more deoxynucleotide triphosphates including at least one deoxynucleotide triphosphate that is labeled, and a DNA polymerase;

(b) subjecting said admixture to a temperature and time sufficient to produce a pRb2/p130 amplification product; and (c) visualizing said pRb2/p130 amplification product with a fluorochrome conjugate specific to said label; and (d) comparing the visualized pRb2/p 130 amplification product obtained in step a to a visualized amplification product for a corresponding wild type exon.

Another embodiment of the present invention is a kit comprising some or all of the reagents, compositions, and supplies needed to carry out the methods, procedures, and techniques disclosed herein.

These and other objects will be apparent to those skilled in the art from the following discussion.

DESCRIPTION OF THE FIGURES

FIG. 2 is a plot of the probability of survival in the same 100 patients with endometrial carcinoma, as stratified by stage and pRb2/p130 expression.

FIG. 4 is the nucleotide sequence (SEQ ID NO:4) of the 5' end and 5' upstream region of the human pRb2/p130 gene showing the transcription start site (→) and the sequence complementary to a primer utilized for a primer extension analysis (underlined). Position +1 is assigned to the A of the ATG translation start codon (bold and underlined). The sequences corresponding to the Sp1 factor recognition motif are boxed. Also boxed are the sequence motifs corresponding to the MyoD and Ker1 transcription factors. The nucleotides beginning at position 1 through position 240 correspond to exon 1 of pRb2/p130. The lowercase letters beginning at position 241 represent the first ten nucleotides of intron 1.

DETAILED DESCRIPTION OF THE INVENTION

A. Abbreviations and Definitions

1. Abbreviations

Figure 1:
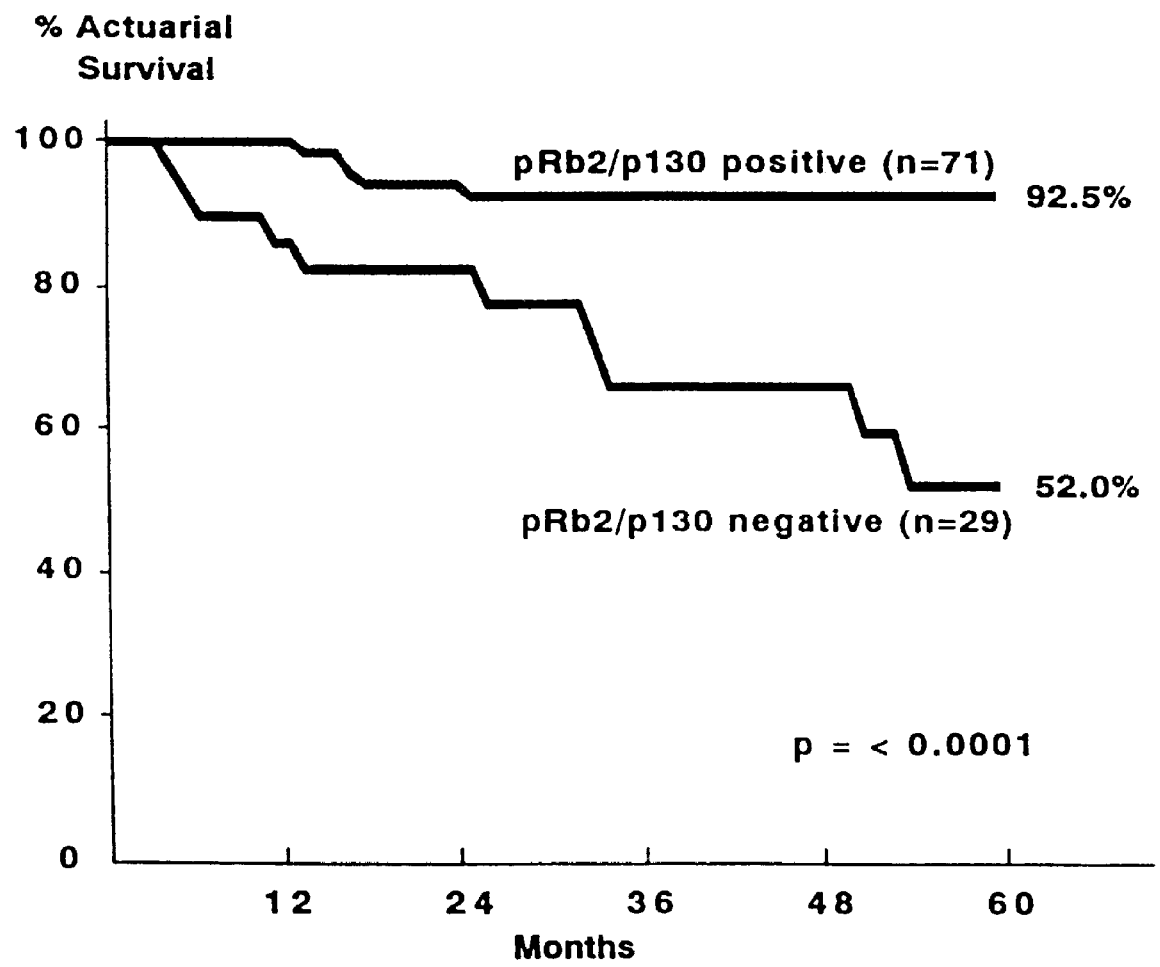
FIG. 1 is a plot of the probability of survival of 100 patients with endometrial carcinoma (all stages) who were characterized as having either pRb2/p130-positive or pRb2/p130-negative tumors.

| | |
|---|---|
| bp | base pairs |
| BSA | Bovine Serum Albumin |
| dATP | deoxyadenosine triphosphate |
| dCTP | deoxycytidine triphosphate |
| dGTP | deoxyguanosine triphosphate |
| DIG DNA | Digoxigenin-labeled DNA |
| DIG-dUTP | Digoxigenin-deoxyuridine triphosphate |
| DNA | deoxyribonucleic acid |
| dTTP | deoxythymidine triphosphate |
| EDTA | ethylene diamine tetraacetate |
| FITC | fluorescein isothiocyanate |
| PCR | polymerase chain reaction |
| PHA | phytohemagglutinin |
| PRINS | oligonucleotide-PRimed IN Situ synthesis |
| RNA | ribonucleic acid |
| SDS | sodium dodecyl sulfate |
| SSC | standard saline citrate |
| SSCP | single-strand conformation polymorphism |
| TBE | buffer mixture of 0.09M tris, 0.09M boric acid, and 2.5 mM EDTA |

2. Definitions

"Allele" refers to one or more alternative forms of a gene occupying a given locus on a chromosome.

"Affected tissue" means tissue which, through visual or other examination, is believed to contain a purported cancerous or precancerous lesion.

"Amplification product" refers to a nucleic acid segment produced by amplification procedures such as PCR, SSCP, and PRINS, which product is complementary to the template segment amplified.

"Downstream" identifies sequences which are located in the direction of expression, i.e., on the 3'-side of a given site in a nucleic acid.

"Endometrial cancer" or "endometrial carcinoma" means a polypoid growth arising in the endometrium.

"Expression", with respect to the pRb2/p130 gene, means the realization of genetic information encoded in the gene to produce a functional RNA or protein. The term is thus used in its broadest sense, unless indicated to the contrary, to include either transcription or translation.

"Expression level", with respect to the pRb2/p130 gene, means not only an absolute expression level, but also a relative expression level as determined by comparison with a standard level of pRb2/p130 expression.

"Genomic DNA" refers to all of the DNA sequences composing the genome of a cell or organism. In the invention described herein it includes the exons, introns, and regulatory elements for the pRb2/p130 gene.

"Grading", with respect to a tumor sample, means a classification of the perceived degree of malignancy. In grading tumor samples, a pathologist or other observer evaluates the degree of differentiation (e. g. grade 1, well differentiated, grade 2, moderately differentiated, grade 3, poorly differentiated) of the tissue.

"Gynecologic cancer" means a tumor arising in the uterus, ovary, cervix, vagina, vulva, or fallopian tube, as well as gestational trophoblastic disease.

"Hybridization" means the Watson-Crick base-pairing of essentially complementary nucleotide sequences (polymers of nucleic acids) to form a double-stranded molecule.

"3'-noncoding region" means those nucleic acid sequences downstream of the termination codon.

"Non-small cell lung cancer" (NSCLC) means all forms of lung cancer except small cell lung cancer (SCLC). In particular, by non-small cell lung cancer is meant the group of lung cancers including squamous cell carcinomas, adenocarcinomas, bronchiolo-alveolar carcinomas and large cell carcinomas.

"Polymorphic" refers to the simultaneous occurrence in the population of genomes showing allelic variations. As used herein the term encompasses alleles producing different phenotypes, as well as proteins for which amino acid variants exist in a population, but for which the variants do not destroy the protein's function.

"Primer" refers to an oligonucleotide which contains a free 3' hydroxyl group that forms base pairs with a complementary template strand and is capable of acting as the starting point for nucleic acid synthesis by a polymerase. The primer can be single-stranded or double-stranded, however, if in double-stranded form, the primer is first treated in such a way so as to separate it from its complementary strand.

"pRb2/p130 gene" means the gene which encodes the pRb2/p130 protein, the cDNA of which is set forth as SEQ ID NO:1, and all allelic variations and mutants thereof.

"pRb2/p130 intron" as used herein means a wild type intron segment of the pRb2/p130 gene, as well as any allelic variations thereof.

"pRb2/p130 protein" means the translation product of the pRb2/p130 gene, including all allelic variations and mutants thereof. The pRb2/p130 amino acid sequence is set forth as SEQ ID NO:2.

"Prognosis" is used according to its ordinary medical meaning, that is, the prospect of recovery from a disease.

"Splice junction" or "exon-intron junction" refers to the nucleotide sequence immediately surrounding an exon-intron boundary of a nuclear gene. As used herein the term includes the sites of breakage and reunion in the mechanism of RNA splicing.

"Splice signal dinucleotide" refers to the first two nucleotides (5'-terminal) or the last two nucleotides (3'-terminal) of an intron. In highly conserved genes the 5'-terminal dinucleotide is GT and the 3'-terminal dinucleotide is AG. Alternatively, the 5'-terminal dinucleotide and the 3'-terminal dinucleotide are referred to as the "donor" and "acceptor" sites, respectively.

"Substantially complementary nucleotide sequence" means, as between two nucleotide sequences, a relationship such that the sequences demonstrate sufficient Watson-Crick base-pair matching to enable formation of a hybrid duplex under hybridization conditions. It is not required, however, that the base-pair matchings be exact.

"Upstream" identifies sequences which are located in the direction opposite from expression, i.e. on the 5'-side of a given site in a nucleic acid.

The present invention provides methods for the identification of individuals at risk for cancer, and for the detection and evaluation of cancers. These methods are of two basic types: methods based on determination of pRb2/p130 expression levels, and methods based on determination of the genomic structure of pRb2/p130.

B. Methods Based on Determination of pRb2/p130 Expression Levels

The present invention provides improved methods, based on pRb2/p130 expression levels, for the diagnosis and prognosis of cancers including but not limited to gynecologic cancers and non-small cell lung cancers. Among the gynecologic cancers to which these methods may be applied are ovarian cancer and endometrial cancer.

1. Gynecologic Cancers

Early ovarian cancer is frequently asymptomatic, or produces only mild symptoms which might be ignored by the patient. The majority of ovarian tumors have spread beyond the ovary, and frequently beyond the pelvis, at the time of diagnosis. Improved methods for the diagnosis and prognosis of ovarian cancer will be useful in treatment selection, and should have a favorable effect on patient outcomes. The present invention rests on the discovery that in ovarian cancer tissue, there is a correlation between the expression of pRb2/p130 and tumor grade.

Endometrial cancer often follows a favorable course, however a considerable proportion of these cases behave poorly and ultimately die of the disease. Currently used surgical-pathologic parameters do not always allow the identification of this subset of patients.

According to the F.I.G.O. criteria for staging in endometrial cancer, surgical procedure should always include peritoneal washing, abdominal hysterectomy, bilateral salpingo-oophorectomy and systematic pelvic and paraaortic lymphadenectomy. Indeed, this operation is often unnecessarily "radical" and potentially dangerous to patients with tumors limited to the uterine corpus. This observation becomes more relevant if it is considered that patients with endometrial cancer very often present also cardiovascular disease, diabetes mellitus, hypertension and severe obesity (Wingo et al., *Am J Obstet Gynecol* 152:803–8 (1985), which are known risk factors for morbidity from abdominal surgery (DiSaia et al., "Adenocarcinoma Of The Uterus" In: *Clinical Gynecologic Oncology*, St. Louis: Mosby-Year Book, p. 156–93 (1993). On the other hand, in the obese or patients at high surgical risk total hysterectomy can be easily and safely performed by the vaginal technique (Massi et al., *Am J Obstet Gynecol* 174:1320–6 (1996); Pitkin, *Obstet Gynecol* 49:567–9 (1977); Peters et al., *Am J Obstet Gynecol* 146:285–90 (1983)). With this in view, the relative pRb2/p130 expression, assayed according to the present invention may be used in the selection of candidates for a less aggressive surgical treatment, without decreasing their chance of cure, as well as being helpful for the identification of high risk patients, to whom every surgical effort should be attempted and post-surgical treatment given.

Normal cells of the endometrium express a relatively high level of pRb2/p130 protein. The present invention rests on the discovery of a highly statistical inverse correlation between the expression of pRb2/p130 in tissues from endometrial cancer patients and the eventual clinical outcome following treatment. Decreased levels of pRb2/p130 are significantly associated with a poor survival. The study results reported herein indicate that the risk of dying of endometrial carcinoma is increased almost fivefold in patients whose tumors were pRb2/p130 negative, regardless of the tumor stage or grade of differentiation.

Tissue with the greatest malignant potential expresses little or no pRb2/p130. Accordingly, a sample is contacted with an antibody specific for pRb2/p130 protein. In the case of endometrial cancer, the sample may typically comprise endometrial tissue, and may specifically comprise an endometrial tumor. The amount of antibody bound by the sample may be determined relative to the amount of antibody bound by a sample of normal endometrial tissue. The difference in the amount of antibody bound by the normal and test samples is indicative of the patient's prognosis. The endometrial carcinoma study described in Example 1 concurrently tested a known molecular prognostic indicator, i.e., DNA index, various classic clinical-pathologic parameters and pRb2/p130 expression. Decreased levels of pRb2/p130 were significantly associated with a poorer survival. The expression of pRb2/p130 thus represents an independent predictor of clinical outcome in endometrial carcinoma. Well known risk factors, such as F.I.G.O. stage and tumor ploidy were also confirmed as independent prognosticators, although of minor strength. The pRb2/p130 expression was significantly correlated with tumor ploidy and patient age, in that pRb2/p130 negativity was associated with aneuploidy (P=0.001) and with age>65 years (P=0.008), in accordance with the known negative impact of such features on survival in endometrial cancer (DiSaia et al., *Am J Obstet Gynecol* 151:1009–15 (1985); Susini et al., *Am J Obstet Gynecol* 170:527–34 (1994); Massi et al., *Am J Obstet Gynecol* 174:1320–6 (1996)). However, it is noteworthy that tumor ploidy resisted as an independent prognostic variable by multivariate analysis. Stratification by pRb2/p130 status and ploidy allowed identification of patient subgroups with significant differences in survival (data not shown). A trend toward correlation was also found between pRb2/p130 status and another major prognostic indicator such as grade of differentiation, where pRb2/p130 negativity was more frequent among moderately and poorly differentiated tumors (P=0.06). Furthermore, concerning grade of differentiation, stratification by pRb2/p130 status revealed significant differences in survival within each grade group (data not shown). Expression of pRb2/p130 was not correlated with tumor stage; pRb2/p130 negative tumors were equally distributed among different tumor stages, thus indicating that this feature is typical of certain tumors, from their onset in early stages.

Thus, the pRb2/p130 expression level may serve as a convenient molecular marker to replace or augment conventional prognostic techniques. An important advantage of the use of pRb2/p130 expression over classical surgical pathologic parameters as a prognostic factor is that the former can be determined at the time of the initial diagnosis, before any therapy is initiated. For patients not previously treated by radiotherapy or chemotherapy, low levels of pRb2/p130 can be used to identify tumors with a tendency to behave aggressively.

An early accurate determination of the aggressiveness of disease in an individual patient is a necessary part of designing a course of treatment. In cases where the test method of the invention identifies a poor prognosis, adjuvant therapy, such as radiation therapy or chemotherapy, may be initiated. This more aggressive treatment should increase the patient's chance of survival. The pRb2/p130 expression level, even in early stages of the disease, is reflective of the malignant potential of the patient's carcinoma and the aggressiveness of the ensuing disease course. This form of "molecular based" prognosis can be evaluated more consistently than conventional prognostic factors which are based upon subjective evaluations of histological type, grade of differentiation, depth of myometrial invasion, degree of lymph nodal metastases, extra-uterine spread, and the other factors upon which endometrial carcinoma prognoses are presently based.

2. Lung Cancer

In the case of lung cancer, a sample of lung tissue is removed from an individual by conventional biopsy techniques which are well-known to those skilled in the art. The sample is generally collected by needle biopsy. See, for example, *Cancer: Principles & Practice of Oncology*, V. T. DeVita, Jr. et al., eds. 3rd edition (1989), J. B. Lippincott Co., Philadelphia, Pa., p. 616–619, incorporated herein by reference (transcarinal needle biopsy and transthoracic percutaneous fine-needle aspiration biopsy). For identification of lung lesions as comprising NSCLC, the sample is taken from the disease lesion. The disease lesion is first located by x-ray or other conventional lung lesion imaging techniques known to those skilled in the art. For testing for latent NSCLC or NSCLC predisposition, the tissue sample may be taken from any site in the lung. Tissue with the greatest malignant potential expresses little or no pRb2/p130. Normal lung tissue cells express a high level of pRb2/p130 protein. The pRb2/p130 expression level in the cells of the patient lung tumor tissue can be compared with the level in normal lung tissue of the same patient, or with the level in the lung tissue of a normal control group.

Non-small cell lung cancer (NSCLC) includes squamous cell carcinomas, adenocarcinomas, bronchiolo-alveolar carcinomas and large cell carcinomas. A highly significant statistical inverse correlation has been established between the expression of pRb2/p130 in tissues from non-small cell lung cancers and the tissues' pathological grading by skilled pathologists.

Thus, the pRb2/p130 expression level may serve as a convenient molecular marker to replace or augment conventional tumor grading. Accurate tumor grading is a necessary part of designing a course of treatment for the individual patient. Grading is reflective of the malignant potential of the tumor in question and thus the aggressiveness of the ensuing disease course. The generation of vital tumor grade information is made easier, by relying on pRb2/p130 as a molecular surrogate for more subjective observations concerning tumor histology. This form of "molecular-based" grading can be performed more consistently than conventional pathological grading which is based upon subjective evaluations by expert pathologists. pRb2/p130 expression levels may also serve as a convenient molecular marker for the presence of active or latent NSCLC, or predisposition to NSCLC.

Lung lesions may be identified as non-small cell lung carcinomas (NSCLCs) by showing a decrement in the expression of pRb2/p130 in the lesion compared to the level of pRb2/p130 in normal, non-cancerous control lung tissue. Similarly, the level of pRb2/p130 expression in lung tissue of individuals with no apparent lung lesion but other symptoms of lung cancer, or in disease-free individuals, indicates latent NSCLC or risk of NSCLC, respectively. Early diagnosis of NSCLC, even before the appearance of visible lung lesions, will permit earlier initiation of treatment and increased survival.

According to the practice of the invention, an at least about one-third decrement in pRb2/p130 expression level in an affected lung tissue sample, in comparison with normal controls, indicates that the lesion is an NSCLC. Similarly, a pRb2/p130 expression decrement of about one-third or greater in lung tissue of patients who are free of lung lesions but manifest other potential lung cancer symptoms such as sputum cytology irregularities, coughing or bronchitis, is indicative of pre-lesion NSCLC. An about one-third or greater pRb2/p130 expression decrement in lung tissue of otherwise healthy individuals manifesting no symptoms of lung cancer is believed indicative of a risk of future NSCLC. Decrements in pRb2/p130 expression of about one-half or greater are even more indicative of NSCLC disease or NSCLC predisposition.

According to one aspect of the invention, individuals who are disease free are evaluated for risk in contracting NSCLC. The test method may be used to identify individuals at risk of developing NSCLC from among populations exposed to environmental carcinogens, e. g. asbestos workers, miners, textile workers, tobacco smokers and the like, and from among families having a history of NSCLC or other forms of cancer.

3. Methods for Determining Expression Levels

According to the practice of the present invention, a sample of affected tissue is removed from a cancer patient by conventional biopsy techniques which are well-known to those skilled in the art. The sample is preferably obtained from the patient prior to initiation of radiotherapy or chemotherapy. The sample is then prepared for a determination of pRb2/p130 expression level.

Determining the relative level of expression of the pRb2/p130 gene in the tissue sample comprises determining the relative number of pRb2/p130 RNA transcripts, particularly mRNA transcripts in the sample tissue, or determining the relative level of the corresponding pRb2/p130 protein in the sample tissue. Preferably, the relative level of pRb2/p130 protein in the sample tissue is determined by an immunoassay whereby an antibody which binds pRb2/p130 protein is contacted with the sample tissue. The relative pRb2/p130 expression level in cells of the sampled tumor is conveniently determined with respect to one or more standards. The standards may comprise, for example, a zero expression level on the one hand and the expression level of the gene in normal tissue of the same patient, or the expression level in the tissue of a normal control group on the other hand. The standard may also comprise the pRb2/p130 expression level in a standard cell line. The size of the decrement in pRb2/p130 expression in comparison to normal expression levels is indicative of the future clinical outcome following treatment.

Methods of determining the level of mRNA transcripts of a particular gene in cells of a tissue of interest are well-known to those skilled in the art. According to one such method, total cellular RNA is purified from the effected cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters by, e.g., the so-called "Northern" blotting technique. The RNA is immobilized on the filters by heating. Detection and quantification of specific RNA is accomplished using appropriately labelled DNA or RNA probes complementary to the RNA in question. See *Molecular Cloning: A Laboratory Manual*, J. Sambrook et al., eds., 2nd edition, Cold Spring Harbor Laboratory Press, 1989, Chapter 7, the disclosure of which is incorporated by reference.

In addition to blotting techniques, the mRNA assay test may be carried out according to the technique of in situ hybridization. The latter technique requires fewer tumor cells than the Northern blotting technique. Also known as "cytological hybridization", the in situ technique involves depositing whole cells onto a microscope cover slip and probing the nucleic acid content of the cell with a solution containing radioactive or otherwise labelled cDNA or cRNA probes. The practice of the in situ hybridization technique is described in more detail in U.S. Pat. No. 5,427,916, the entire disclosure of which is incorporated herein by reference.

The nucleic acid probes for the above RNA hybridization methods can be designed based upon the published pRb2/p130 cDNA sequence of Li et al., *Genes Dev.* 7: 2366–2377 (1993), the entire disclosure of which is incorporated herein by reference. The nucleotide sequence is reproduced herein as SEQ ID NO:1. The translation initiation codon comprises nucleotides 70–72 of SEQ ID NO:1. The translation termination codon comprises nucleotides 3487–3489.

Either method of RNA hybridization, blot hybridization or in situ hybridization, can provide a quantitative result for the presence of the target RNA transcript in the RNA donor cells. Methods for preparation of labeled DNA and RNA probes, and the conditions for hybridization thereof to target nucleotide sequences, are described in *Molecular Cloning*, supra, Chapters 10 and 11, incorporated herein by reference.

The nucleic acid probe may be labeled with, e.g., a radionuclide such as $^{32}P$, $^{14}C$, or $^{35}S$; a heavy metal; or a ligand capable of functioning as a specific binding pair member for a labelled ligand, such as a labelled antibody, a fluorescent molecule, a chemolescent molecule, an enzyme or the like.

Probes may be labelled to high specific activity by either the nick translation method or Rigby et al.,*J. Mol. Biol.* 113: 237–251 (1977) or by the random priming method, Fienberg et al., *Anal. Biochem.* 132: 6–13 (1983). The latter is the method of choice for synthesizing $^{32}P$-labelled probes of high specific activity from single-stranded DNA or from RNA templates. Both methods are well-known to those skilled in the art and will not be repeated herein. By replacing preexisting nucleotides with highly radioactive nucleotides, it is possible to prepare $^{32}P$-labelled DNA probes with a specific activity well in excess of $10^8$ cpm/microgram according to the nick translation method. Autoradiographic detection of hybridization may then be performed by exposing filters on photographic film. Densitometric scanning of the filters provides an accurate measurement of mRNA transcripts.

Where radionuclide labelling is not practical, the random-primer method may be used to incorporate the dTTP analogue 5-(N-(N-biotinyl-epsilon-aminocaproyl)-3-aminoallyl)deoxyuridine triphosphate into the probe molecule. The thus biotinylated probe oligonucleotide can be detected by reaction with biotin binding proteins such as avidin, streptavidin, or anti-biotin antibodies coupled with fluorescent dyes or enzymes producing color reactions.

The relative number of pRb2/p130 transcripts may also be determined by reverse transcription of mRNA followed by amplification in a polymerase chain reaction (RT-PCR), and comparison with a standard. The methods for RT-PCR and variations thereon are well known to those of ordinary skill in the art.

According to another embodiment of the invention, the level of pRb2/p130 expression in cells of the patient tissue is determined by assaying the amount of the corresponding pRb2/p130 protein. A variety of methods for measuring expression of the pRb2/p130 protein exist, including Western blotting and immunohistochemical staining. Western blots are run by spreading a protein sample on a gel, using an SDS gel, blotting the gel with a cellulose nitrate filter, and probing the filters with labeled antibodies. With immunohistochemical staining techniques, a cell sample is prepared, typically by dehydration and fixation, followed by reaction with labeled antibodies specific for the gene product coupled, where the labels are usually visually detectable, such as enzymatic labels, florescent labels, luminescent labels, and the like.

According to one embodiment of the invention, tissue samples are obtained from patients and the samples are embedded then cut to e.g. 3–5 μm, fixed, mounted and dried according to conventional tissue mounting techniques. The fixing agent may advantageously comprise formalin. The embedding agent for mounting the specimen may comprise, e.g., paraffin. The samples may be stored in this condition. Following deparaffinization and rehydration, the samples are contacted with an immunoreagent comprising an antibody specific for pRb2/p130. The antibody may comprise a polyclonal or monoclonal antibody. The antibody may comprise an intact antibody, or fragments thereof capable of specifically binding pRb2/p130 protein. Such fragments include, but are not limited to, Fab and F(ab')$_2$ fragments. As used herein, the term "antibody" includes both polyclonal and monoclonal antibodies. The term "antibody" means not only intact antibody molecules, but also includes fragments thereof which retain antigen binding ability.

Appropriate polyclonal antisera may be prepared by immunizing appropriate host animals with pRb2/p130 protein and collecting and purifying the antisera according to conventional techniques known to those skilled in the art. Monoclonal antibody may be prepared by following the classical technique of Kohler and Milstein, *Nature* 254:493–497 (1975), as further elaborated in later works such as *Monoclonal Antibodies, Hybridomas: A New Dimension in Biological Analysis*, R. H. Kennet et al., eds., Plenum Press, New York and London (1980).

Substantially pure pRb2/p130 for use as an immunogen for raising polyclonal or monoclonal antibodies may be conveniently prepared by recombinant DNA methods. According to one such method, pRb2/p130 is prepared in the form of a bacterially expressed glutathione S-transferase (GST) fusion protein. Such fusion proteins may be prepared using commercially available expression systems, following standard expression protocols, e.g., "Expression and Purification of Glutathione-S-Transferase Fusion Proteins", Supplement 10, unit 16.7, in *Current Protocols in Molecular Biology* (1990). Also see Smith and Johnson, *Gene* 67: 34–40 (1988); Frangioni and Neel, *Anal. Biochem.* 210: 179–187 (1993). Briefly, DNA encoding for pRb2/p130 is subcloned into a pGEX2T vector in the correct reading frame and introduced into *E. coli* cells. Transformants are selected on LB/ampicillin plates; the plates are incubated 12 to 15 hours at 37° C. Transformants are grown in isopropyl-β-D-thiogalactoside to induce expression of pRb2/p130-GST fusion protein. The cells are harvested from the liquid cultures by centrifugation. The bacterial pellet is resuspended and the cell pellet sonicated to lyse the cells. The lysate is then contacted with glutathione-agarose beads. The beads are collected by centrifugation and the fusion protein eluted. The GST carrier is then removed by treatment of the fusion protein with thrombin cleavage buffer. The released pRb2/p130 protein is recovered.

As an alternative to immunization with the complete pRb2/p130 molecule, antibody against pRb2/p130 can be raised by immunizing appropriate hosts with immunogenic fragments of the whole protein, particularly peptides corresponding to the carboxy terminus of the molecule.

The antibody either directly or indirectly bears a detectable label. The detectable label may be attached to the primary anti-pRb2/p130 antibody directly. More conveniently, the detectable label is attached to a secondary antibody, e.g., goat anti-rabbit IgG, which binds the primary antibody. The label may advantageously comprise, for example, a radionuclide in the case of a radioimmunoassay; a fluorescent moiety in the case of an immunofluorescent assay; a chemiluminescent moiety in the case of a chemiluminescent assay; or an enzyme which cleaves a chromogenic substrate, in the case of an enzyme-linked immunosorbent assay.

Most preferably, the detectable label comprises an avidin-biotin-peroxidase complex (ABC) which has surplus biotin-binding capacity. The secondary antibody is biotinylated. To locate pRb2/p130 antigen in the tissue section under analysis, the section is treated with primary antiserum against pRb2/p130, washed, and then treated with the secondary antiserum. The subsequent addition of ABC localizes peroxidase at the site of the specific antigen, since the ABC adheres non-specifically to biotin. Peroxidase (and hence antigen) is detected by incubating the section with e.g. $H_2O_2$ and diaminobenzidine (which results in the antigenic site being stained brown) or $H_2O_2$ and 4-chloro-1-naphthol (resulting in a blue stain).

The ABC method can be used for paraffin-embedded sections, frozen sections, and smears. Endogenous (tissue or cell) peroxidase may be quenched e.g. with $H_2O_2$ in methanol.

The level of pRb2/p130 expression in tumor samples may be compared on a relative basis to the expression in normal tissue samples by comparing the stain intensities, or comparing the number of stained cells. The lower the stain intensity with respect to the normal controls, or the lower the stained cell count in a tissue section having approximately the same number of cells as the control section, the lower the expression of the pRb2/p130 gene, and hence the higher the expected malignant potential of the sample.

In the examples which follow, a polyclonal antibody raised against pRb2/p130, designated ADL1 was utilized. The specificity of the antibody has been confirmed by Western blot analysis, (Pertile et al., *Cell Growth & Diff* 6:1659–64 (1995); Claudio et al., *Cancer Res* 56:2003–8 (1996)), as well as by immunoprecipitation of the antibody with the in vitro translated forms of the cDNAs coding for pRb2/p130 and for the other retinoblastoma related proteins, pRb/p105 and p107. The ADL1 antibody was able to immunoprecipitate only the in vitro translated form of the pRb2/p130 protein (Baldi et al., *Clin Cancer Res* 2:1239–45 (1996).

C. Methods Based on Determination of the Genomic Structure of pRb2/p130

Figure 3A:
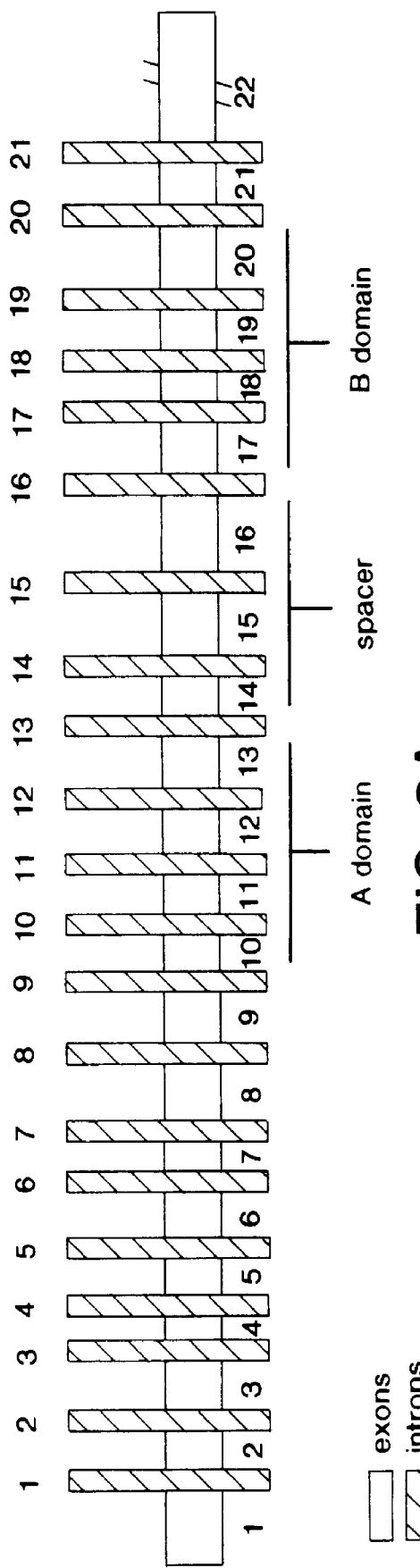
FIG. 3A is a schematic representation of the human pRb2/p130 gene. Exons are represented by open rectangles, while the introns are represented by hatched vertical bars. Exons 10–13, 14–16, and 17–20, represent domain A, a spacer, and domain B, respectively.

The genomic structure of the human pRb2/p130 gene is described herein. The pRb2/p130 genomic DNA has been cloned and sequenced. The pRb2/p130 gene has been mapped to the long arm of chromosome 16, an area previously reported to show loss of heterozygosity (LOH) for human neoplasias. The putative promoter for pRb2/p130 has been identified, cloned and sequenced. The complete intron-exon organization of the gene has been elucidated. The pRb2/p130 gene contains 22 exons and 21 introns, spanning over 50 kb of genomic DNA. The length of the individual exons ranges from 65 bp to 1517 bp, while the length of individual introns ranges from 82 bp to 9837 bp. The organization of these exons and introns are shown in FIG. 3A. The location and size of each exon and intron of pRb2/p130, as well as the nucleotide sequences at the exon-intron junctions are shown below in Table 7. (SEQ ID NOS:6–47). The exon sequences are shown in upper case letters, while the intron sequences are in lower case letters. The superscript numbers correspond to the nucleotide positions of the exon-intron boundaries on SEQ ID NO:1.

All the exons were completely sequenced and no discrepancies were found in comparing the genomic sequence of the exons and the cDNA sequence previously reported. Li, Y. et al., *Genes* 7:2366–2377 (1993). The exon-intron boundaries were determined by comparing the sequence of the genomic DNA described herein to the published cDNA sequence of Li et al., supra. The exon-intron boundaries were identified as the positions where the genomic DNA sequence diverged from that of the cDNA.

With the exception of exon 22, the largest of all the exons (1517 bp in length), the exons found were relatively small, with the shortest, exons 4 and 7, comprising only 65 nucleotides each. Exons 10 through 20 code for the region of the pRb2/p130 protein which form the "pocket region". Exons 10 through 13 and 17 through 20 translate to Domain A and Domain B, respectively. Exons 14, 15, and 16 code for the region of the pRb2/p130 protein, known as the "spacer." The spacer lies between Domains A and B.

The introns have been completely sequenced. The shortest intron, intron 16, lying between exons 16 and 17, is only 82 bp in length, whereas the largest intron, intron 21, spans 9837 bp. Intron 21 is located between exons 21 and 22. The complete sequences for the introns are given as SEQ ID NOS:48–68. All of the intron sequences of pRb2/p130 conform to the GT-AG rule found to be characteristic of other human genes. Breathnach, R. et al., *Annu. Rev. Biochem.* 50:349–383 (1981). This rule identifies the generic sequence of an intron as GT . . . . . . AG. Introns having this generic form are characterized as conforming to the GT-AG rule. The two dinucleotides, GT and AG, known as the "splice signal dinucleotides," act as signals for splicing out the introns during the processing of the pRb2/p130 mRNA. Point mutations in splice signal dinucleotides have been associated with aberrant splicing in other genes in vivo and in vitro. See generally, Genes V, B. Lewin, Oxford University Press, pp. 913–916, New York (1994) and Yandell et al., supra at p. 1694. Thus, it is important to identify any mutations to the splice signal dinucleotides or other sequences that are excluded from the RNA transcript during splicing.

The pRb2/p130 genomic structure and intron sequences described herein may be used to delineate mutations and rearrangements associated with tumor formation. The genomic structure and intron sequences herein may also be used to screen for naturally occurring polymorphisms at the nucleotide level. Knowledge of a specific single polymorphism can be used to eliminate a mutation in pRb2/p130 as a causative factor in a tumor if the purported mutation displays the same pattern as the polymorphism. Knowledge of polymorphisms in pRb2/p130 can be used to determine the genetic linkage of an identical mutation, and in turn, the tracing of parental origin and family histories without the need for time for time intensive sequencing if mutation is of germline origin. These polymorphisms can then be utilized for the development of diagnostic approaches for human neoplasias. However, it should be noted that not all polymorphisms are of equal utility in these applications. It is preferable to seek out mutations in the exons, as these mutations are most likely to lead to tumor development. Further, because the coding regions of the gene are generally more stable and less likely to mutate over time, it follows that polymorphisms in the exon region are typically less common. The detection of a polymorphism in the exon region of pRb2/p130 would enable screening of both genomic DNA and cDNA.

In the examples that follow, several screening methods are exemplified to identify pRb2/p130 mutations and polymorphisms.

1. Transcriptional Control of pRb2/p130

There is evidence that tumor suppressor gene products directly interact with transcription factors, such as MyoD, which regulate not only cell growth, but also cell differentiation. Sang et al., supra at p. 8. Mutations in the sequence region motifs for these transcription factors would be expected to effect the function of the tumor suppressor genes. Accordingly, in addition to identifying the genomic structure of the pRb2/p130 gene, additional experiments were conducted to define the 5'-flanking promoter sequence of pRb2/p130. Part of the putative promotor sequence for pRb2/p130, along with the entire sequence of the first exon and the beginning of the first intron is shown in FIG. 4 (SEQ ID NO:4). The full sequence for the putative promoter region is given in SEQ ID NO:113.

Figure 5:
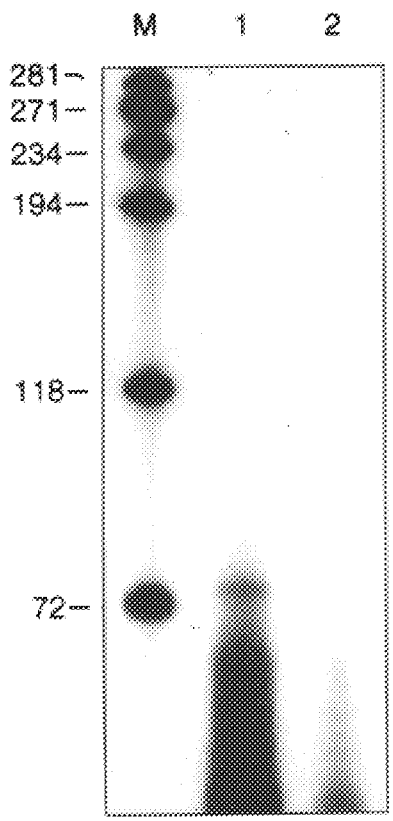
FIG. 5 shows the products of a primer extension experiment done to identify the transcription start site for the human pRb2/p130 gene. Cytoplasmatic RNA was hybridized overnight to an oligonucleotide complementary to the twenty four nucleotides beginning at position −22 of FIG. 4 (SEQ ID NO:4). Lane M contains the molecular-weight marker (φχ174 DNA/Hae III, Promega). Lanes 1 and 2 contain the primer-extended product of pRb2/p130 from HeLa cells and tRNA as template, respectively.

To characterize the pRb2/p130 promoter, a primer extension analysis was performed to locate the transcription initiation site. The protocol for the prime-extension analysis is given in the examples that follow. A twenty four nucleotide segment (SEQ ID NO:114) containing the antisense-strand sequence 26 to 50 nucleotides upstream from the putative ATG codon (See FIG. 4) was end-labeled and used as a primer for an extension reaction on cyctoplasmatic RNA from HeLa cells. As shown in FIG. 5, a major extended fragment of 78 bp was detected (lane 1) from the primer extension done with HeLa cells as the template. The additional bands detected by the primer extension analysis could represent additional initiation sites. This finding (lane 1) is consistent with a transcription initiation site 99 nucleotides upstream of the start codon. On the contrary, there was no primer extension product observed when tRNA was used as a template (lane 2). The probable position of the identified transcription initiation site within the promoter sequence is indicated by the arrow in FIG. 4. The primer extension analysis was repeated three times, and similar results were produced in each instance.

The putative transcription factor-binding sites were identified by their similarity to consensus sequences for known transcription factor-binding sites by use of the SIGNAL SCAN program. A description of this program is included in the examples that follow. The most recognizable sequence motifs are for the transcription factors Sp1 (two sites), Ker1 and MyoD. FIG. 4 shows the location of these motifs. Ker1 is involved in keratinocyte-specific transcription, while MyoD is involved in myogenesis. Leask et al., *Genes Dev.* 4: 1985–1998 (1990); Weintraub, H., *Cell* 75: 1241–1244 (1993). The presence in the promoter region for pRb2/p130 of these sequence motifs supports a hypothesis of an involvement of this gene in the complex pathways regulating differentiation of specific cell systems.

2. Detection of Mutations in pRb2/p130

The present invention provides a method for amplifying the genomic DNA of pRb2/p130 and for screening polymorphisms and mutations therein. The assay methods described herein can be used to diagnose and characterize certain cancers or to identify a heterozygous carrier state. While examples of methods for amplifying and detecting mutations in pRb2/p130 are given, the invention is not limited to the specific methods exemplified. Other means of amplification and identification that rely on the use of the genomic DNA sequence for pRb2/p130 and/or the use of the primers described herein are also contemplated by this invention.

Generally, the methods described herein involve preparing a nucleic acid sample for screening and then assaying the sample for mutations in one or more alleles. The nuclei acid sample is obtained from cells. Cellular sources of genomic DNA include cultured cell lines, or isolated cells or cell types obtained from tissue (or whole organs or entire organisms). Preferably, the cell source is peripheral blood lymphocytes. Methods of DNA extraction from blood and tissue samples are known to those skilled in the art. See, for example, Blin et al., *Nuc. Acids Res.* 3:2303–2308 (1976);

and Sambrook et al., *Molecular Cloning:A Laboratory Manual*, Second Edition, pp. 9.16–9.23, Cold Spring Harbor Laboratory Press, Cold Spring Harbor, N.Y. (1989), the entire disclosure of which is incorporated herein by reference. If the patient sample to be screened is in the form of double-stranded genomic DNA, it is first denatured using methods known to those skilled in the art. Denaturation can be carried out either by melting or subjecting the strands to agents that destabilize the hydrogen bonds, such as alkaline solutions and concentrated solutions of formamide or urea.

In one embodiment of the invention, prior to screening the genomic DNA sample, the pRb2/p130 genomic DNA sample is amplified by use of the polymerase chain reaction (PCR), using a primer pair, a buffer mixture, and an enzyme capable of promoting chain elongation. Methods of conducting PCR are well known to those skilled in the art. See, for example, Beutler et al., U.S. Pat. No. 5,234,811, or Templeton, N.S., *Diag. Mol. Path.* 1(1):58–72 (1992), which are incorporated herein by reference as if set forth at length. The amplification product produced from PCR can then be used to screen for mutations using the techniques known as Single Strand Conformational Polymorphism (SSCP) or Primed In-Situ DNA synthesis (PRINS). Of course, mutations can also be identified through the more laborious task of sequencing the gene isolates of a patient and comparing the sequence to that for the corresponding wild type pRb2/p130 segment.

PCR is carried out by thermocycling, i.e., repeated cycles of heating and cooling the PCR reaction mixture, within a temperature range whose lower end is 37° C. to 55° C. and upper end is around 90° C. to 100° C. The specific temperature range chosen is dependent upon the enzyme chosen and the specificity or stringency required. Lower end temperatures are typically used for annealing in amplifications in which high specificity is not required and conversely, higher end temperatures are used where greater stringency is necessary. An example of the latter is when the goal is to amplify one specific target DNA from genomic DNA. A higher annealing temperature will produce fewer DNA segments that are not of the desired sequence. Preferably, for the invention described herein, the annealing temperature is between 50° C. and 65° C. Most preferably, the annealing temperature is 55° C.

The PCR is generally performed in a buffered aqueous solution, i.e., a PCR buffer, preferably at a pH of 7–9, most preferably about 8. Typically, a molar excess of the primar is mixed with the buffer containing the template strand. For genomic DNA, this ratio is typically $10^6:1$ (primer: template). The PCR buffer also contains the deoxynucleotide triphosphates (dATP, dCTP, dGTP, and dTTP) and a polymerase. Polymerases suitable for use in PCR include, but are not limited to, *E. coli* DNA polymerase I, the Klenow fragment of *E. coli* DNA polymerase I, T4 DNA polymerase, T7 DNA polymerase, Taq DNA polymerase (*Thermus aquaticus* DNA polymerase I), and other heat-stable enzymes which will facilitate the formation of amplification products.

The primers used herein can be naturally occurring oligonucleotides purified from a nucleic acid restriction digest or produced synthetically using any suitable method, which methods are known to those skilled in the art. The primers used herein can be synthesized using automated methods.

Because a mutation can occur in both the exon itself and the splice junction, it is necessary to design primers that will ensure that the entire exon region to be analyzed is amplified. To amplify the entire exon, the oligonucleotide primer for any given exon must be designed such that it includes a portion of the complementary sequence for the promoter region, for the 3'-noncoding region, or for the introns flanking the exon to be amplified, provided however that the primer sequence should not include the sequence for the splice signal dinucleotides. It is important to exclude the complementary sequence for the splice signal dinucleotides from the primer in order to ensure that the entire region, including the splice signal dinucleotide, is amplified. Including the complementary sequences to the splice signal dinucleotides could result in an amplification product that "plasters over" the splice junction and masks any potential mutation that could occur therein. It should be noted, however, that the introns flanking the exon are not limited to the introns immediately adjacent to the exon to be amplified. The oligonucleotide primer can be designed such that it includes a portion of the complementary sequence for the introns upstream or downstream from the exon to exon to be amplified. In the latter instance, the amplification product produced would include more than one exon. Preferably at least 20 to 25 nucleotides of the sequence for each flanking intron are included in the primer sequence.

The primers used herein are selected to be substantially complementary to each strand of the pRb2/p130 segment to be amplified. There must be sufficient base-pair matching to enable formation of a hybrid duplex under hybridization conditions. It is not required, however, that the base-pair matchings be exact. Therefore, the primer sequence may or may not reflect the exact sequence of the pRb2/p130 segment to be amplified. Non-complementary bases or longer sequences can be interspersed into the primer, provided the primer sequence retains sufficient complementarity with the segment to be amplified and thereby form an amplification product.

The primers must be sufficiently long to prime the synthesis of amplification products in the presence of a polymerizing agent. The exact length of the primer to be used is dependent on many factors including, but not limited to, temperature and the source of the primer. Preferably the primer is comprised of 15 to 30 nucleotides, more preferably 18 to 27 nucleotides, and most preferably 24 to 25 nucleotides. Shorter primers generally require cooler annealing temperatures with which to form a stable hybrid complex with the template.

Primer pairs are usually the same length, however, the length of some primers was altered to obtain primer pairs with identical annealing temperatures. Primers of less than 15 bp are generally considered to generate non-specific amplification products.

According to one embodiment of this invention, SSCP is used to analyze polymorphisms and mutations in the exons of pRb2/p130. SSCP has the advantages over direct sequencing in that it is simple, fast, and efficient. The analysis is performed according to the method of Orita et al., *Genomics* 5:874–879 (1989), the entire disclosure of which is incorporated herein by reference. The target sequence is amplified and labeled simultaneously by the use of PCR with radioactively labeled primers or deoxynucleotides. Neither in situ hybridization nor the use of restriction enzymes is necessary for SSCP.

SSCP detects sequence changes, including single-base substitutions (point mutations), as shifts in the electrophoretic mobility of a molecule within a gel matrix. A single nucleotide difference between two similar sequences is sufficient to alter the folded structure of one relative to the other. This conformational change is detected by the appearance of a band shift in the tumor DNA, when compared with the banding pattern for a corresponding wild type DNA segment. Single base pair mutations can be detected following SSCP analysis of PCR products up to about 400 bp. PCR products larger than this size must first be digested with a restriction enzyme to produce smaller fragments.

In another embodiment of the invention, sequence mutations in pRb2/p130 can be detected utilizing the PRINS technique. The PRINS method represents a versatile technique, which combines the accuracy of molecular and cytogenetic techniques, to provide a physical localization of the genes in nuclei and chromosomes. See Cinti et al., *Nuc. Acids Res.* Vol 21, No. 24: 5799–5800 (1993), the entire disclosure of which is incorporated herein by reference. The PRINS technique is based on the sequence specific annealing of unlabeled oligodeoxynucleotides in situ. The oligodeoxynucleotides operate as a primer for in situ chain elongation catalyzed by Taq I polymerase. Labeled nucleotides, labeled with a substance such as biotin or Digoxigenin, act as substrate for chain elongation. The labeled DNA chain is visualized by exposure to a fluorochrome-conjugated antibody specific for the label substance. Preferably, the label is Digoxigenin and the fluorochrome conjugated antibody is anti-Digoxigenin-FITC. This results in the incorporation of a number of labeled nucleotides far greater than the number of nucleotides in the primer itself. Additionally, the specificity of the hybridization is not vulnerable to the problems that arise when labeled nucleotides are placed in the primer. The bound label will only be found in those places where the primer is annealed and elongated.

Neither the SSCP nor the PRINS technique will characterize the specific nature of the polymorphism or mutation detected. If a band shift is detected through use of SSCP analysis, one must still sequence the sample segment and compare the sequence to that of the corresponding wild type pRb2/p130 segment. Similarly, if the absence of one or both of the alleles for a given exon segment is detected by the PRINS technique, the sequence of the segment must be determined and compared to the nucleotide sequence for the corresponding wild type in order to determine the exact location and nature of the mutation, i.e., point mutation, deletion or insertion. The PRINS technique is not capable of detecting polymorphisms.

Protocols for the use of the SSCP analysis and the PRINS technique are included in the examples that follow.

The PRINS method of detecting mutations in the pRb2/p130 gene may be practiced in kit form. In such an embodiment, a carrier is compartmentalized to receive one or more containers, such as vials or test tubes, in close confinement. A first container may contain one or more subcontainers, segments or divisions to hold a DNA sample for drying, dehydrating or denaturing. A second container may contain the PRINS reaction mixture, which mixture is comprised of a PCR buffer, a DIG DNA labeling mixture, a polymerase such as Taq I DNA polymerase, and the primers designed in accordance with this invention (see Example 7, Table 8). The DIG DNA labeling mixture is comprised of a mixture of labeled and unlabeled deoxynucleotides. Preferably, the labeled nucleotides are labeled with either biotin or Digoxigenin. More preferably, the label is Digoxigenin. A third container may contain a fluorochrome conjugated antibody specific to the label. The fluorochrome conjugated antibody specific for Digoxigenin is anti-Digoxigenin-FITC. Suitable conjugated fluorochromes for biotin include avidin-FITC or avidin Texas Red. The fourth container may contain a staining compound, preferably Propidium Iodide (PI). The kit may further contain appropriate washing and dilution solutions.

EXAMPLES

The following examples illustrate the invention. These examples are illustrative only, and do not limit the scope of the invention.

EXAMPLE 1

Expression of pRb2/p130 in Endometrial Carcinoma

A. Patients and Tumors

Between September 1988 and December 1994, 196 patients with previously untreated endometrial carcinoma were seen at the Department of Obstetrics and Gynecology, University of Florence, Italy. To avoid concern for the possibility radiation affecting molecular analyses, the patients who received preoperative irradiation were excluded. In 175 cases surgery was the first treatment. Paraffin-embedded tissue blocks containing the most representative portion of the tumor were available in 104 of these cases; four patients were lost to follow up, leaving a total of 100 patients. Patients' ages ranged from 46 to 84 years with a median age of 64 years. Histologic slides were reviewed to assess histologic type, grade of differentiation and depth of myometrial invasion. The stage was evaluated by microscopic analysis of the surgical specimen according to the 1988 International Federation of Gynecology and Obstetrics (FIGO) classification (*Gynecol Oncol* 35: 125 (1988). Table 1 summarizes the clinical and pathological characteristics of the study group.

B. Surgical Treatment

Surgical treatment included total hysterectomy in 95 cases and extended hysterectomy in five cases. Bilateral salpingo-oophorectomy was always associated. Pelvic and paraaortic lymphadenectomy were performed at the surgeon's discretion, but not systematically. Overall, 43 patients underwent lymphadenectomy. The omentum was removed when appropriate (four cases).

TABLE 1

Clinical And Pathological Features Of 100 Patients In Which pRb2/p130 Expression Was Tested.

| Feature | Number of Patients |
|---|---|
| Age | |
| <65 yr | 52 |
| ≧65 yr | 48 |
| FIGO stage | |
| I | 68 |
| II | 15 |
| III | 14 |
| IV | 3 |
| Histologic type | |
| Adenocarcinoma | 74 |
| Adenosquamous | 17 |
| Adenoacanthoma | 4 |
| Papillary serous | 4 |
| Clear cell | 1 |
| Grade of differentiation | |
| Well differentiated | 44 |
| Moderately differentiated | 26 |
| Poorly differentiated | 25 |
| Not evaluable | 5 |
| Depth of myometrial invasion | |
| ≦50% | 41 |
| >50% | 59 |
| Adjuvant treatment | |
| None | 57 |
| Radiotherapy | 37 |
| Chemotherapy | 6 |

C. Tumor Specimen Collection

For all 100 patients, a tumor specimen was taken fresh from a site regarded to be representative of the lesion immediately after hysterectomy. Each tumor sample was later divided into two parts: one for flow cytometry and the other for histological analysis.

D. Adjuvant Therapy Forty-three of the 100 patients received adjuvant treatment. Of the 43 patients receiving adjuvant treatment, 37 received radiotherapy and 6 received chemotherapy. Poor grade of differentiation, deep myometrial invasion (>50 percent) and tumor outside the uterine corpus (stage>I) were the major criteria for receiving adjuvant treatment. The irradiated patients (37 patients) received 56 Gy on the whole pelvis. Chemotherapy (six patients) was given, when possible, in cases with more advanced disease (stage III–IV). The chemotherapy regimen included cisplatin (60 mg per square meter of body surface area) in combination with cyclophosphamide (600 mg per square meter of body surface area) and epirubicin (60 mg per square meter of body surface area), every 21 days, for six cycles.

E. Follow-up And Evaluation Of Results

After completing the treatment, patients were seen every three months for the first two years, every four months during the third and fourth years, and every six months thereafter. Recurrence was considered as any documented relapse of the tumor either in the pelvis or systemic. Disease-free interval was calculated from the date of the operation. Patients with residual disease after surgery or who recurred within three months from the date of the operation were not considered free of disease and therefore excluded from the disease-free analysis, but not from the actuarial survival calculation. Patients with deaths from causes other than endometrial cancer were considered as lost to follow-up and therefore their survival times were censored at the date of death. Follow-up data were available for all 100 patients, with a median of 48 months (range 20 to 86 months). Disease-free interval and actuarial survival were the endpoints of the study.

F. Flow Cytometric Analysis Of DNA Index

For flow cytometry, a suspension of tumor cells was obtained by mincing the sample with a lancet and scissors in phosphate-buffered saline. The cell suspension was filtered by a 50 micrometer mesh of polyacrylamide, fixed in 70 percent ethanol, and stored at −4° C. until assayed. Prior to DNA analysis the ethanol was removed by centriguation (1500 revolutions/min for ten minutes); the pellet was then resuspended and washed twice in phosphate-buffered saline. The RNA was removed by digestion with ribonuclease (Serva, 0.1 mg/ml in phosphate-buffered saline) for 30 minutes at 37° C. the nuclei were washed in phosphate-buffered saline, and DNA was stained with 40 mg propidium iodide (Becton Dickinson) and 1 gm sodium citrate per liter in distilled water. Human female lymphocytes were added to the samples before enzymatic treatment and staining, and they were used as the DNA diploid standard. The DNA analyses were performed with an Elite flow cytometer (Coulter Corporation, Hialeah, Fla.) provided with a 15 mW Argon laser, at a wavelength of 488 mm. Data were expressed as DNA histograms. The DNA ploidy was given by the DNA index, defined as a proportion of the modal DNA values of the tumor $G_o$ and $G_1$, cells (peak channel) to the DNA content of the diploid standard. The histograms were based on measurement of more than 10,000 cells and resulted, in general, in a good resolution with a coefficient of variation of three to six percent. Calculation of DNA index was done by processing each histogram in the computer-assisted program Multicycle Autofit, version 2.00 (Phoenix Flow Systems, San Diego, Calif.).

All cases with DNA index value of 1 (±0.04) were classified as diploid and others as aneuploid.

G. Antibody

Rabbit polyclonal immune serum, designated ADL1, was prepared against pRb2/p130 according to the procedure of Harlow and Lane, *Antibodies: A Laboratory Manual*, Cold Spring Laboratory Press (1988), Chapter 5, the disclosure of which is incorporated herein by reference. Rabbits were immunized with a conjugate comprising the peptide Glu-Asn-His-Ser-Ala-Leu-Leu-Arg-Arg-Leu-Gln-Asp-Val-Ala-Asn-Asp-Arg-Gly-Ser-His-Cys (SEQ ID NO:3) coupled to keyhole limpet hemocyanin (KLH). The peptide corresponds to the carboxy terminus of the pRb2/p130 protein. Briefly, rabbits were immunized with the SEQ ID NO:3-KLH conjugate by subcutaneous injection once every two weeks until a total of three injections were given. The initial injection (primary immunization) comprised 1 mg SEQ ID NO:3-KLH conjugate in 500 μl PBS, plus 500 μl of complete Freund's adjuvant. The second and third injections (boosts) comprised 500 μg of the conjugate in 500 μl PBS, plus 500 μl of complete Freund's adjuvant. The rabbits were bled after the third injection. Subsequent boosts, with the same composition as the second and third injections, were given once a month.

H. Immunohistochemical Analysis

Sections of each tumor specimen were cut to 5-micrometer, mounted on glass and dried overnight at 37° C. All sections were then deparaffinized in xylene, rehydrated through graded alcohol series and washed in phosphate-buffered saline. This buffer was used for all subsequent washes and for the dilution of the antibodies. Sections were quenched in 0.5 percent hydrogen peroxide and blocked with diluted ten percent normal goat anti-rabbit serum. Slides were then incubated for one hour at room temperature with the ADL1 immune serum at a dilution of 1:1000, then incubated with diluted goat anti-rabbit biotinylated antibody (Vector, Burlingame, Calif.) for 30 minutes at room temperature. After washing in phosphate-buffered saline, the slides were processed by the ABC method (Vector) for 30 minutes at room temperature. Diaminobenzidine (Sigma, St. Louis) was used as the final chromogen, and hematoxylin as the nuclear counterstain. Negative controls for each tissue section consisted of substitution of the primary antibody with the corresponding pre-immune serum. Moreover, preincubation of the antibody with an excess of the corresponding immunizing antigen, blocked the immunocytochemical reaction, thus confirming the specificity of the ADL1 antibody for pRb2/p130 (data not shown).

All the samples were processed under the same conditions. In each experiment, normal uterine tissue was also included as a control. The results of pRb2/p130 inunun-ostaining were independently interpreted by three observers who had no previous knowledge of the clinical outcome of each patient. The level of concordance, expressed as the percentage of agreement between the observers was 90 percent (90 of 100 specimens). In the remaining specimens the score was obtained from the opinions of the two investigators in agreement. The results were expressed as percentage of positive cells. In each tumor sample, at least 20 high power fields were randomly chosen and 2,000 cells were counted. The pRb2/p130 immunostaining was mostly nuclear, but a few specimens also exhibited cytoplasmatic staining. This pattern of immunoreactivity could be referred to microstructural alterations caused by the fixing and embedding procedures, or might reflect differences in the levels of expression and in the localization of this antigen during the various phases of the cell cycle, as has already been shown at the molecular level (Claudio et al., *Cancer Res* 56: 2003–8 (1996).

I. Cellular Reactivity Cutoff Point

To evaluate the prognostic value of pRb2/p130 expression, the patients' disease-free and actuarial survival durations were compared after dividing them into two groups using different cutoff points of percent pRb2/p130 positivity. The P values were significant for poor disease-free and actuarial survival when a cutoff point of 40 percent or fewer reactive cells was used (P=0.003 and P<0.001, respectively). The level of significance decreased to P=0.02 and P=0.01, respectively, with a cutoff point of 50 percent positivity and became insignificant with a cutoff point of 60 percent or higher positivity. Consequently, subsequent survival analyses were carried out using a 40 percent reactivity cutoff point. A similar approach to identify optimal cutoff points has been used in immunohistochemical studies utilizing p53 expression and bcl-2 expression (Shim et al., *J Natl Cancer Inst* 88: 519–29 (1996); Silvestrini et al., *J Clin Oncol* 14: 1604–10 (1996)).

J. Statistical Analysis

Fisher's exact test was used to evaluate the association between pRb2/p130 expression and the other prognostic variables (Fienberg, *The Analysis Of Cross-Classified Categorical Data*, MIT Press, Cambridge, Mass.; Zelterman et al., "Contingency Tables In Medical Studies", NEJM Books 293–310 (1992)). Disease-free interval and actuarial survival were calculated according to the Kaplan-Meier method (Kaplan et al., *Am Stat Assoc* 53: 457–81 (1958)) and evaluated by the log-rank test (Miller, *Survival Analysis*, pp. 44–102, John Wiley, New York (1981)). Univariate Cox analysis was used to assess the effect of each prognostic variable on disease-free interval and survival. A multivariate analysis (Cox proportional-hazards regression, with forward selection of variables) (Cox, *J R Stat Soc* 34: 187–220 (1972)) was performed to estimate which of the possible risk factors yielded independent prognostic information. Data analysis was performed with the SPSS statistical package, release 5.0.1 (SPSS Inc., Chicago, Ill.).

K. Results

A brown stain indicated the presence of pRb2/p130 in tumor cells. The specimens were characterized as having no detectable staining, staining in only a few positive cells (about ten percent), staining in more than 40 percent of the cells, or intense staining in the majority of cells. Tumors with immunostaining in more than 40 percent of cells were considered to be positive for pRb2/p130.

In normal uterine samples, strong immunoreactivity was detected for pRb2/p130 in all endometrial and endocervical epithelial cells. Of the 100 endometrial adenocarcinomas examined, five showed immunoreactivity for pRb2/p130 in 20 percent or fewer cells, 15 had reactivity in 30 percent of the cells and nine had staining in 40 percent of the cells. These 29 tumors (29 percent) were considered pRb2/p130 negative. The remaining 71 tumors were scored as 50 percent positivity in 11 cases, as 60 percent positivity in 49 cases and with staining in over 70 percent of the cells in four cases. These 71 tumors (71 percent) were considered pRb2/p130 positive.

The DNA index values showed a diploid type in 73 cases and an aneuploid type in 27 cases. The DNA index of the aneuploid tumors was hypodiploid in one case, hypertetraploid in four cases; the remaining 22 cases had a modal DNA content in the diploid to tetraploid range (1<DNA index<2).

L. Association Of pRb2/p130 Expression With Clinical And Pathological Features

The expression of pRb2/p130 was inversely correlated with patients' age: in patients younger than 65 years pRb2/p130 negative tumors were nine of 52 (17.3 percent) in contrast with 20 of 48 in patients aged 65 years or older (41.6 percent) (P=0.008). Immunostaining for pRb2/p130 was more frequently negative among patients with aneuploid tumors (13 of 27; 48.1 percent) than among those with a diploid pattern (16 of 73; 21.9 percent) (P=0.001). Tumors negative for pRb2/p130 were more frequent among patients with poorly or moderately differentiated carcinomas, but this association was not statistically significant (P=0.06). The level of expression of pRb2/p130 did not differ significantly between patients with tumors limited to the uterine corpus (stage I) and those in whom the tumor had spreads outside the corpus uteri (stage>I), (P=0.4). No significant difference in the incidence of pRb2/p130 negativity was found among the histologic types, nor among patients with different degrees of myometrial infiltration.

Expression of pRb2/p130, tumor ploidy, FIGO stage and grade of differentiation were significantly correlated with disease-free interval and actuarial survival, by Univariate Cox analysis, as shown in Table 2. Other clinicopathological features, including age, histologic type and depth of myometrial invasion were not associated with the outcome (data not shown).

As shown in FIG. 1, patients with pRb2/p130 negative tumors had a significantly reduced disease-free interval and survival (P=0.001 and P<0.0001, respectively); the five-year survival probability was 52.0 percent in patients with such tumors, in contrast with 92.5 percent in patients with pRb2/p130 positive tumors.

TABLE 2

Significant Predictors Of Clinical Outcome In 100 Patients With Endometrial Carcinoma, According To Cox Univariate Analysis For Disease-free Interval And Actuarial Survival.

| Variable | Recurrence Rate Ratio | 95% Confidence Interval | P Value | Death Rate Ratio | 95% CI+ | P Value |
|---|---|---|---|---|---|---|
| pRb2/p130 | | | | | | |
| positive | 1 | | | 1 | | |
| negative | 4.83 | 1.70–13.64 | 0.003 | 6.68 | 2.32–19.27 | <0.0001 |
| FIGO stage | | | | | | |
| I | 1 | | | 1 | | |
| >I | 5.42 | 1.86–15.77 | 0.002 | 5.08 | 1.78–14.51 | 0.002 |
| Ploidy status | | | | | | |
| diploid | 1 | | | 1 | | |

TABLE 2-continued

Significant Predictors Of Clinical Outcome In 100 Patients With Endometrial Carcinoma, According To Cox Univariate Analysis For Disease-free Interval And Actuarial Survival.

| Variable | Recurrence Rate Ratio | 95% Confidence Interval | P Value | Death Rate Ratio | 95% CI+ | P Value |
|---|---|---|---|---|---|---|
| aneuploid | 3.43 | 1.24–9.51 | 0.01 | 5.94 | 2.14–16.42 | <0.001 |
| Grade of differentiation (1 = well differentiated, 2 = moderately differentiated, 3 = poorly differentiated) | | | | | | |
| 1 | 1 | | | 1 | | |
| 2 | 7.73 | 1.54–38.67 | 0.01 | 13.88 | 1.65–116.27 | 0.01 |
| 3 | 7.45 | 1.43–38.78 | 0.01 | 18.36 | 2.23–151.10 | 0.007 |

Table 3 shows the results of Cox proportional-hazards regression analysis in which the response to pRb2/p130 immunostaining, tumor ploidy, FIGO stage and grade of differentiation were tested simultaneously to estimate the rate ratios for the occurrence of death from disease in patients with endometrial cancer. Negative immunostaining for pRb2/p130 resulted as the strongest independent predictor of poor outcome. Patents with pRb2/p130 negative tumors had a significantly higher rate ratio for dying due to disease (4.91) than patients with pRb2/p130 positive tumors. Multivariate analysis revealed that tumor spread outside the corpus uteri (stage>I) and aneuploidy were also associated with a higher probability of death from disease, whereas grade of differentiation yielded no independent prognostic information. By the combined use of pRb2/p130 expression and FIGO stage, a more accurate definition of risk of death was possible.

FIG. 2 presents Kaplan Meier survival estimates according to these stratified risk groups. The following is the comparison between the groups by the log-rank test:

Stage I, pRb2/p130-Positive versus Stage>I, pRb2/p130-Positive: difference not significant;

Stage I, pRb2/p130-Positive versus Stage I, pRb2/p130-Negative: P=0.01;

Stage I, pRb2/p130-Negative versus Stage>I, pRb2/p130-Negative: P=0.005;

Stage>I, pRb2/p130-Positive versus Stage>I, pRb2/p130-Negative: P=0.003;

Stage>I, pRb2/p130-Positive versus Stage I, pRb2/p130-Negative: difference not significant.

TABLE 3

Results Of Cox Proportional-Hazards Regression Analysis For Survival Data.

| Variable | Rate Ratio | 95% Confidence Interval | P Value* |
|---|---|---|---|
| pRb2/p130 | | | |
| positive | 1 | | |
| negative | 4.91 | 1.66–14.54 | 0.004 |
| FIGO stage | | | |
| I | 1 | | |
| >I | 4.18 | 1.43–12.23 | 0.009 |
| Ploidy status | | | |
| Diploid | 1 | | |
| Aneuploid | 3.36 | 1.17–9.62 | 0.02 |

*Chi-square of the model, P < 0.001

EXAMPLE 2

Expression of pRb2/p130 in Ovarian Cancer

A. Tumors

Sixty archived (formalin fixed and paraffin-embedded) epithelial carcinoma specimens were obtained from the Department of Pathology at Pennsylvania Hospital. The specimens included Grade 1, Grade 2, and Grade 3 tumors.

B. Immunohistochemistry

Immunohistochemical staining was performed using an automated immunostainer (Ventana ES, Ventana Medical Systems, Tucson, Ariz.) and a Peroxidase-DAB immunodetection kit (Ventana Medical Systems). Five micron sections were cut from each tumor specimen. The sections were mounted on slides and air-dried. The sections were deparaffinized in xylene and hydrated through a graded alcohol series into water. A polyclonal anti-RB2 primary antibody was applied at a dilution of 1:500 for 30 minutes at 37° C. The slides were then incubated with a biotinylated goat anti-rabbit antibody for 30 minutes. The slides were then incubated with a horseradish peroxidase conjugated-avidin. Hydrogen peroxide was used as the oxidizing substrate, and diaminobenzidine (DAB) was used as the chromogen. The slides were counterstained with hematoxylin, dehydrated, and mounted. The intensity of pRb2/p130 immunostaining was evaluated.

C. Results

The preliminary results are shown in Table 4. These results suggest that as the grade of tumor increases, less expression of the pRb2/p130 protein is detected. The pRb2/p130 expression level may therefore be useful in grading and as a prognostic indicator in human epithelial ovarian cancer.

TABLE 4

Immunohistochemical Detection Of pRb2/p130 In Human Epithelial Ovarian Carcinoma Specimens

| | Intensity of Immunostaining | | | |
|---|---|---|---|---|
| Grade of Tumor | Negative | + | ++ | +++ |
| Grade 1 | 20% | 40% | 40% | 0% |
| Grade 2 | 50% | 33% | 17% | 0% |
| Grade 3 | 37% | 26% | 23% | 14% |

EXAMPLE 3

Expression of pRb2/p130 in Lung Cancer, Series I

A. Antibody Against pRb2/p130

The rabbit polyclonal immune serum designated ADL1, as described in Example 1G, was used in these studies.

B. Antibody Against p107

Rabbit polyclonal immune serum was prepared against p107 (ADL2) by immunizing rabbits with a bacterially expressed GST-p107 fusion protein. Expression of the fusion protein was performed according to the procedure reported by Smith and Johnson, *Gene* 67:31–40 (1988) and Frangioni and Neel, *Anal. Biochem.* 210:179–187 (1993). Rabbits were immunized with the fusion protein by subcutaneous injection once every two weeks until a total of three injections were given. The initial injection (primary immunization) comprised 500 µg protein in 500 µl PBS, plus 500 µl of incomplete Freund's adjuvant. The second and third injections (boosts) comprised 100 µg of the protein in 500 µl PBS, plus 500 µl of incomplete Freund's adjuvant. The rabbits were bled after the third injection. Subsequent boosts, with the same composition as the second and third injections, were given once a month.

C. Antibody Against pRb/p105

An anti-pRb/p105 monoclonal antibody (XZ 77), prepared as described by Hu et al., *Mol. Cell. Biol.* 11:5792–5799 (1991), was used in these studies.

D. Tissue Samples

Lung tissue specimens from 51 patients with surgically resected lung cancer were obtained from patients who had not received chemo- or radiotherapy prior to surgical resection. The samples consisted of 39 squamous cell carcinomas and 12 adenocarcinomas. Histological diagnosis and grading were performed by a skilled lung pathologist. Samples were graded on the scale of 1-2-3 with "3" representing the most malignant disease and "1" representing the least malignant disease. Normal lung tissue samples containing the stratified columnar epithelia of trachea, bronchi and adjacent glands were obtained either from biopsy or autopsy performed within 10 hours of the patient's death.

E. Immunohistochemistry

Sections from each lung tissue specimen were cut at 3–5 µm, mounted on glass and dried overnight at 37° C. All sections were then deparaffinized in xylene, rehydrated through a graded alcohol series and washed in phosphate-buffered saline (PBS). The same buffer was used for all subsequent washes and for dilution of antibodies.

Tissue sections for pRb2/p130 and p107 detection were sequentially quenched in 0.5% hydrogen peroxide and blocked with diluted 10% normal goat anti-rabbit serum (Vector Laboratories). The slides were incubated for 1 hour at room temperature with the rabbit polyclonal immune serum (ADL1) raised against pRb2/p130 at a dilution of 1:2000, or the ADL2 antibody against p107 at a dilution of 1:500. The slides were then incubated with diluted goat anti-rabbit biotinylated antibody (Vector Laboratories) for 30 minutes at room temperature.

Sections for pRb/p105 detection were heated twice in a microwave oven for 5 min each at 700 W in citrate buffer (pH6), were quenched sequentially in 0.5% hydrogen peroxide, and were blocked with diluted 10% normal horse anti-mouse serum (Vector Laboratories, Inc.) The monoclonal mouse anti-human pRb/p105 antibody XZ77 (at a dilution of 1:500) was added and incubated for 120 min. at room temperature. After being washed in PBS, the slides were incubated with diluted horse anti-mouse biotinylated antibody (Vector Laboratories, Inc.) for 30 min. at room temperature.

Slides were processed by the so-called "ABC" method according to the instructions of the biotinylated antibody manufacturer (Vector Laboratories) for 30 minutes at room temperature. Diaminobenzidine was used as the final chromagen, and hematoxylin as a nuclear counterstain. Negative controls for each tissue section consisted of substitution of the primary antibody with pre-immune serum for ADL1 and ADL2, or leaving out the primary antibody for XZ77.

Three pathologists scored the expression of pRb2/p130 protein as the percentage of positively stained nuclei on a scale of 0-1-2-3: 0=undetectable level of expression; 1=low expression level (1–30% cells stained positive); 2=medium expression level (30–60% cells stained positive); 3=high expression level (60–100% cells stained positive). The normal lung tissue samples comprising the stratified epithelia of the trachea, bronchi and adjacent glands were strongly stained, indicating a high expression level.

F. Results

The results are shown in Table 5.

TABLE 5

| Sample No. | Type | Grading | pRb2/p130 Level | p107 Level | pRb/p105 Level |
|---|---|---|---|---|---|
| 1 | squamous | 3 | 0 | 2 | 3 |
| 2 | squamous | 2 | 3 | 1 | 3 |
| 3 | squamous | 1 | 3 | 1 | 3 |
| 4 | squamous | 1 | 3 | 1 | 3 |
| 5 | squamous | 2 | 2 | 1 | 2 |
| 6 | squamous | 2 | 3 | 1 | 2 |
| 7 | squamous | 3 | 1 | 1 | 3 |
| 8 | squamous | 2 | 3 | 1 | 2 |
| 9 | squamous | 2 | 1 | 1 | 2 |
| 10 | squamous | 2 | 3 | 1 | 1 |
| 11 | squamous | 2 | 3 | 1 | 2 |
| 12 | squamous | 1 | 3 | 1 | 3 |
| 13 | squamous | 3 | 1 | 1 | 1 |
| 14 | squamous | 1 | 3 | 1 | 3 |
| 15 | squamous | 3 | 0 | 2 | 3 |
| 16 | squamous | 2 | 2 | 1 | 2 |
| 17 | squamous | 2 | 3 | 1 | 2 |
| 18 | squamous | 2 | 1 | 1 | 2 |
| 19 | squamous | 1 | 3 | 1 | 3 |
| 20 | squamous | 3 | 1 | 1 | 1 |
| 21 | squamous | 2 | 3 | 1 | 2 |
| 22 | squamous | 3 | 2 | 1 | 3 |
| 23 | squamous | 2 | 3 | 1 | 3 |
| 24 | squamous | 2 | 3 | 1 | 1 |

TABLE 5-continued

| Sample No. | Type | Grading | pRb2/p130 Level | p107 Level | pRb/p105 Level |
|---|---|---|---|---|---|
| 25 | squamous | 2 | 3 | 1 | 2 |
| 26 | squamous | 1 | 3 | 1 | 3 |
| 27 | squamous | 3 | 1 | 2 | 3 |
| 28 | squamous | 2 | 3 | 1 | 3 |
| 29 | squamous | 1 | 3 | 1 | 3 |
| 30 | squamous | 1 | 3 | 1 | 3 |
| 31 | squamous | 2 | 2 | 1 | 2 |
| 32 | squamous | 2 | 3 | 1 | 2 |
| 33 | squamous | 3 | 3 | 1 | 3 |
| 34 | squamous | 2 | 3 | 1 | 2 |
| 35 | squamous | 2 | 0 | 1 | 2 |
| 36 | squamous | 2 | 3 | 1 | 1 |
| 37 | squamous | 2 | 3 | 1 | 2 |
| 38 | squamous | 1 | 3 | 1 | 3 |
| 39 | squamous | 3 | 1 | 1 | 0 |
| 40 | adenocarcinoma | 3 | 0 | 2 | 2 |
| 41 | adenocarcinoma | 1 | 2 | 1 | 2 |
| 42 | adenocarcinoma | 2 | 1 | 2 | 1 |
| 43 | adenocarcinoma | 2 | 1 | 1 | 2 |
| 44 | adenocarcinoma | 2 | 0 | 2 | 1 |
| 45 | adenocarcinoma | 2 | 1 | 1 | 2 |
| 46 | adenocarcinoma | 1 | 2 | 1 | 2 |
| 47 | adenocarcinoma | 3 | 0 | 2 | 2 |
| 48 | adenocarcinoma | 1 | 2 | 1 | 2 |
| 49 | adenocarcinoma | 3 | 0 | 2 | 2 |
| 50 | adenocarcinoma | 2 | 1 | 2 | 1 |
| 51 | adenocarcinoma | 2 | 0 | 1 | 2 |

Statistical Analysis

The data from Table 5 were analyzed using the Jonkheere-Terpstra test and STATXACT statistical software (Cytel Software Corp., Cambridge, Mass.) determine whether there is a relationship between tissue grade and protein expression level.

A statistically significant inverse relationship was found between the pathological grading and the expression of pRb2/p130 in squamous cell carcinomas (p<0.0001) and adenocarcinomas (p<0.004).

Although a statistically significant inverse relationship was found between pathological grading and the expression of pRb/p105 in squamous cell carcinomas (p=0.004), no such relationship was found between pRb/p105 expression and grading of adenocarcinomas.

EXAMPLE 4

Expression of pRb2/p130 in Lung Cancer, Series II

A. Lung Cancer Specimens

One hundred and fifty eight lung cancer specimens were obtained from patients that underwent a surgical resection (lobectomy or pneumonectomy) in the Departments of Thoracic Surgery of the V. Monaldi Hospital and of the II University of Naples (Italy) between January 1995 and April 1996. Specimens were obtained only from patients who had not received chemo- or radiotherapy prior to surgical resection.

The histological diagnoses and classifications of the tumors were based on the WHO criteria, and the postsurgical pathologic TNM stage was determined using the guidelines of the American Joint Committee on Cancer.

The routine histopathological evaluation of the 158 tumor specimens analyzed was performed independently of the pRb2/p130 immunostaining. Thirty two tumors were adenocarcinomas, 118 were squamous carcinomas, 4 were carcinoids and 4 were small cell lung cancers. Eighty seven tumors (55.1%) were classified as stage I, 43 tumors (27.1%) were classified as stage II and 28 tumors (17.7%) were classified as stage IIIa. The adenocarcinomas and squamous carcinomas were classified by grade, as shown in Table 6.

B. Immunohistochemistry

Sections of each specimen were cut at 3–5 μm, mounted on glass and dried overnight at 37° C. All the sections were then deparaffinized in xylene, rehydrated through a graded alcohol series and washed in PBS. This buffer was used for all subsequent washes and for the dilution of the antibodies. Sections were heated twice in a microwave oven for five minutes each at 700 W in citrate buffer (pH 6), sequentially quenched in 0.5% hydrogen peroxide and blocked with diluted 10% normal goat anti-rabbit serum. Slides were then incubated for one hour at room temperature with rabbit polyclonal immune serum raised against pRb2/p130 at a dilution ranging from 1:500 to 1:1500, then incubated with diluted goat anti-rabbit biotinylated antibody (Vector Laboratories) for 30 minutes at room temperature. After washings in PBS, the slides were processed by the ABC method (Vector Laboratories) for 30 minutes at room temperature. Diaminobenzidine was used as the final chromogen, and hematoxylin as the nuclear counterstain. Negative controls for each tissue section were obtained by substituting the primary antibody with pre-immune serum.

All samples were processed under the same conditions. Three pathologists (A. Baldi, G. G. Giordano and F. Baldi) evaluated the staining pattern of the protein separately and scored it for the percentage of positive nuclei: score 1, less than 10% of positive cells (low to undetectable level of expression); score 2, from 10% to 50% of positive cells (medium level of expression); score 3, more than 50% of positive cells (high level of expression). The level of concordance, expressed as the percentage of agreement between the observers was 90% (142 of 158 specimens). In the remaining specimens the score was obtained from the opinions of the two investigators in agreement. At least 20 high power fields were chosen randomly and 2000 cells were counted. This coded score was preferred to facilitate the statistical analyses.

C. Statistical Analysis

Statistical analyses, using the chi square test, were performed to evaluate the significance of associations between the different variables of the considered tumors (histological type and grading, evidence of metastasis, pRb2/p130 expression levels). A p value <0.05 was considered statistically significant.

D. Results pRb2/p130 immunostaining was mostly nuclear, but some specimens clearly exhibited cytoplasmatic staining with a low to absent background.

Immunohistochemical staining patterns of the tumors can be summarized as follows: 50 specimens (31.6%) showed low to undetectable levels of pRb2/p130 (score 1), 73 specimens (46.2%) exhibited medium pRb2/p130 expression levels, while high levels of expression were detected in 35 specimens (22.2%). The small number of small cell lung cancers and carcinoids included in this study did not allow statistical analysis in these histological groups. All the SCLCs specimens exhibited low to undetectable pRb2/p130 expression levels, while a high level of expression of this protein was recognized in all carcinoids.

Statistical analyses revealed that pRb2/p130 expression did not correlate with tumor stage or with TNM status (p=n.s.). However, a negative significant relationship was found between pRb2/p130 expression level and the histological grading (p<0.0001). The correlation between histological grade and pRb2/p130 expression is shown in Table 6.

TABLE 6

| Type | Grade | No. | pRb2/p130 Level 1 | 2 | 3 |
|---|---|---|---|---|---|
| Squamous | 1 | 13 | 2 | 0 | 11 |
| Squamous | 2 | 42 | 8 | 28 | 6 |
| Squamous | 3 | 63 | 30 | 27 | 6 |
| Adenocarcinoma | 1 | 8 | 0 | 2 | 6 |
| Adenocarcinoma | 2 | 27 | 4 | 16 | 2 |
| Adenocarcinoma | 3 | 2 | 2 | 0 | 0 |

The mean follow-up period was too short to allow a detailed analysis of the disease free and the overall survival time of the patients. However, in looking at the development of metastasis in the patients, we found a significant inverse relationship between metastasis and the expression of pRb2/p130 (p<0.0001).

EXAMPLE 5

Isolation and Characterization of Genomic Clones

A. Isolation of Genomic Clones

To isolate the entire human pRb2/p130 gene, a human P1 genomic library (Genome System Inc., St. Louis, Mo.) was screened by using two primers made from the published cDNA sequence, Li et al., *Genes Dev.* 7:2366–2377 (1993). The sequences for the primers used to isolate the genomic clones are GTATACCATTTAGCAGCTGTCCGCC (SEQ ID NO:116) and the complement to the sequence GTGTGCCATTTATGTGATGGCAAAG (SEQ ID NO:115).

Figure 3B:
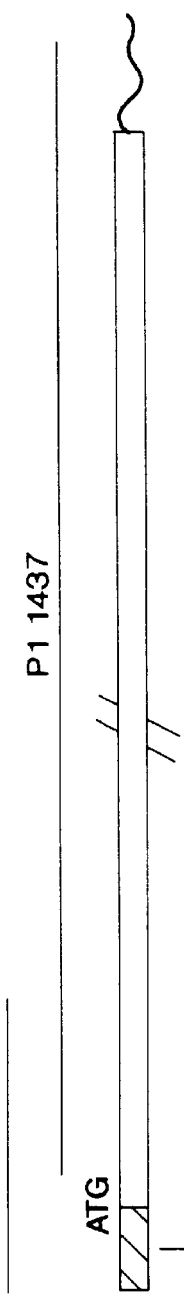
FIG. 3B is a schematic representation of the human pRb2/p130 genomic clones derived from the P1 and λ phage libraries.

One of the clones identified upon screening the P1 genomic library (clone no. 1437, FIG. 3B) was confirmed by Southern blot hybridization to contain a part of the pRb2/p130 gene. To obtain the additional 5' flanking sequence of the pRb2/p130 gene containing the putative promoter region, a human placenta genomic DNA phage library (EMBL3 SP6/T7) from Clontech, Palo Alto, Calif. was screened with a cDNA probe according to the method of Sambrook et al., *Molecular Cloning: A Laboratory Manual*, Second Edition, pp. 12.30–12.38, Cold Spring Harbor Laboratory Press, Cold Spring Harbor, N.Y. (1989), the entire disclosure of which is incorporated herein by reference. The cDNA probe, labeled with [$\gamma$-$^{32}$P], corresponded to the first 430 bp after the start codon of the published cDNA sequence, Li et al., supra. Of the two positive clones obtained, one, identified as $\phi$SCR3 (FIG. 3B), was determined to contain the 5' flanking region of the pRb2/p130 gene.

B. Identification of Exon/Intron Boundaries

To precisely characterize the position of the exons and the exon/intron boundaries in the genomic DNA, a set of oligonucleotide primers were used to sequence the genomic DNA clones. The primers were synthesized based upon the cDNA nucleotide sequence of pRb2/p130 such that they annealed to the genomic DNA at roughly 150 bp intervals. The exon/intron boundaries were identified from those positions in which the genomic DNA sequence differed from that of the published cDNA sequence.

C. Sequencing of Clones

Sequencing of the recombinant clones was carried out in part by automated DNA sequencing using the dideoxy terminator reaction chemistry for sequence analysis on the Applied Biosystem Model 373A DNA sequencer and, in part, by using a dsDNA Cycle Sequencing System kit purchased from GIBCO BRL, Gaithersburg, Md., according to the instructions of the manufacturer.

D. Synthesis of Oligonucleotide Primers

All oligonucleotide primers used herein were synthesized using Applied Biosystems DNA-RNA synthesizer Model 394, using beta-cyanoethyl phosphoramidite chemistry.

E. Results of the Genomic Clones Characterization

The human pRb2/p130 gene consists of 22 exons and 21 introns and spans more than 50 kb of genomic DNA. The organization of these exons and introns are shown approximately to scale in FIG. 3A. The location and size of each exon and intron of pRb2/p130, as well as the nucleotide sequences at the exon-intron boundaries are shown in Table 7 (SEQ ID NOS:6–47). The exons range in size from 65 to 1517 bp in length. The introns, which range in size from 82–9837 bp in length, have been completely sequenced. The nucleotide sequences are given as SEQ ID NOS:48–68.

EXAMPLE 6

Characterization of Transcriptional Control Elements

A. Cell Culture and RNA Extraction

The human HeLa (cervix epithelioid carcinoma) cell line was obtained from the American Type Culture Collection and maintained in culture in Dulbecco's modified Eagle medium (DHEM) with 10% fetal calf serum (FCS) at 37° C. in a 10% $CO_2$-containing atmosphere. Cytoplasmatic RNA was extracted utilizing the RNAzol B method (CINNA/BIOTECX, Friendswood, Tex.).

TABLE 7

Exon-Intron Boundaries of the Human pRb2/p130 Gene

| Exon No. (bp) | 5' Donor sequence | 3' Acceptor sequence | Intron No. (bp) |
| --- | --- | --- | --- |
| 1 (240) | ACGCTGGAG$^{309}$gtgcgctcgc (SEQ ID NO:6) | tcttttacag$^{310}$GGAAATGAT (SEQ ID NO:7) | 1 (4220) (SEQ ID NO:66) |
| 2 (131) | AGAGCAGAG$^{440}$gtaactatgt (SEQ ID NO:8) | ttaataccag$^{441}$CTTAATCGA (SEQ ID NO:9) | 2 (3507) (SEQ ID NO:67) |
| 3 (201) | GAAACAGCG$^{641}$gtaggttttc (SEQ ID NO:10) | tcccccaaag$^{642}$GCGACAGCC (SEQ ID NO:11) | 3 (3865) (SEQ ID NO:48) |
| 4 (65) | ATGCAAAAG$^{706}$gtaagaaaat (SEQ ID NO:12) | aatcctgcag$^{707}$GTAATTTCC (SEQ ID NO:13) | 4 (4576) (SEQ ID NO:49) |
| 5 (129) | ATTTTAAAG$^{835}$gtaggtttgt (SEQ ID NO:14) | acaccatag$^{836}$GCTTATCTG (SEQ ID NO:15) | 5 (1618) (SEQ ID NO:50) |
| 6 (161) | GAAAAAAAG$^{996}$gtttgtaagt (SEQ ID NO:16) | ttcatcatag$^{997}$CTCCTTAAG (SEQ ID NO:17) | 6 (92) (SEQ ID NO:51) |
| 7 (65) | AGAGAGTTT$^{1061}$gtgagtactt (SEQ ID NO:18) | ttcctatag$^{1062}$TAAAGCCAT (SEQ ID NO:19) | 7 (889) (SEQ ID NO:52) |
| 8 (187) | TTTGACAAG$^{1248}$gtgagtttag (SEQ ID NO:20) | ttttctttag$^{1249}$TCCAAAGCA (SEQ ID NO:21) | 8 (4586) (SEQ ID NO:53) |
| 9 (167) | GATTCTCAG$^{1415}$gttagtttga (SEQ ID NO:22) | cctttttag$^{1416}$GACATGTTC (SEQ ID NO:23) | 9 (2127) (SEQ ID NO:54) |
| 10 (90) | GTGCTAAAG$^{1525}$gtaattgtgc (SEQ ID NO:24) | atttctacag$^{1526}$AAATTGCCA (SEQ ID NO:25) | 10 (716) (SEQ ID NO:55) |
| 11 (104) | GATTTATCT$^{1629}$gtgagtaaaa (SEQ ID NO:26) | attttatag$^{1630}$GGTATTCTG (SEQ ID NO:27) | 11 (837) (SEQ ID NO:56) |
| 12 (138) | TTTTATAAG$^{1767}$gtatttccca (SEQ ID NO:28) | tttatttcag$^{1768}$GTGATAGAA (SEQ ID NO:29) | 12 (1081) (SEQ ID NO:57) |
| 13 (165) | TGTGAAGAG$^{1932}$gtgaaaatca (SEQ ID NO:30) | tcttcatag$^{1933}$GTCATGCCA (SEQ ID NO:31) | 13 (1455) (SEQ ID NO:58) |
| 14 (112) | TTGGAAGGA$^{2044}$gtaagtttaa (SEQ ID NO:32) | ttgacccctag$^{2045}$GCATAACAT (SEQ ID NO:33) | 14 (2741) (SEQ ID NO:59) |
| 15 (270) | CTGTGCAAG$^{2314}$gtaaggaagg (SEQ ID NO:34) | ctgtcactag$^{2315}$GTATTGCCA (SEQ ID NO:35) | 15 (197) (SEQ ID NO:60) |
| 16 (281) | TTTAGAAAG$^{2595}$gtaattttc (SEQ ID NO:36) | tatctcctag$^{2596}$GTATACCAT (SEQ ID NO:37) | 16 (82) (SEQ ID NO:61) |
| 17 (177) | ATGGCAAAG$^{2772}$gtgagtacca (SEQ ID NO:38) | gtttgccag$^{2773}$GTCACAAAA (SEQ ID NO:39) | 17 (1079) (SEQ ID NO:62) |
| 18 (72) | CGGAGCCAG$^{2844}$gtaactacat (SEQ ID NO:40) | ttctctaaag$^{2845}$GTGTATAGA (SEQ ID NO:41) | 18 (659) (SEQ ID NO:63) |
| 19 (107) | AAGATAGAA$^{2950}$gtgggatctt (SEQ ID NO:42) | ctggctgcag$^{2951}$CCAGTAGAG (SEQ ID NO:43) | 19 (572) (SEQ ID NO:64) |
| 20 (202) | CAGGCAAAT$^{3153}$gtaagtatga (SEQ ID NO:44) | tttttaaacag$^{3154}$ATGGGATGC (SEQ ID NO:45) | 20 (901) (SEQ ID NO:65) |
| 21 (165) | CCTTCAAAG$^{3318}$gtgagcctaa (SEQ ID NO:46) | cccaccatag$^{3319}$AGACTGAGA (SEQ ID NO:47) | 21 (9837) (SEQ ID NO:68) |
| 22 (1517) | to the polyadenylation signal | | |

B. Primer Extension Analysis

To characterize the pRb2/p130 promoter, a primer extension analysis was performed to locate the transcription initiation site. The primer for this analysis was an oligonucleotide, 5'ACCTCAGGTGAGGTGAGGGC-CCGG 3' (SEQ ID NO:114), complementary to the pRb2/p130 genomic DNA sequence starting at position −22 (See FIG. 4, SEQ ID NO:4). The primer was end labeled with [γ$^{32}$P]ATP and hybridized overnight with 20 μg of HeLa cytoplasmatic RNA at 42° C. The primer-annealed RNA was converted into cDNA by avian myeloblastosis virus reverse transcriptase in the presence of 2 mM deoxynucleotides at 42° C. for 45 minutes. The cDNA product was then analyzed on 7% sequencing gel containing 8M urea. The position of the transcription start site was mapped from the length of the resulting extension product.

C. SIGNAL SCAN Program

Several of the transcription factor-binding motifs were identified through the use of SIGNAL SCAN VERSION 4.0. SIGNAL SCAN is a computer program that was developed by Advanced Biosciences Computing Center at the University of Minnesota, St. Paul, Minn.. This program aids molecular biologists in finding potential transcription factor binding sites and other elements in a DNA sequence. A complete description of the program can be found in Prestridge, D. S., *CABIOS* 7: 203–206 (1991), the entire disclosure of which is incorporated herein as if set forth at length.

SIGNAL SCAN finds sequence homologies between published signal sequences and an unknown sequence. A signal, as defined herein, is any short DNA sequence that may have known significance. Most of the known signals represent transcriptional elements. The program does not interpret the significance of the identified homologies; interpretation of the significance of sequences identified is left up to the user. The significance of the signal elements varies with the signal length, with matches to short segments having a higher probability of random occurrence.

D. Results of the Primer Extension Analysis And SIGNAL SCAN

FIG. 5 shows the results of the primer extension analysis done to locate the transcription initiation site for pRb2/p130. A major extended fragment of 78 bp was detected (lane 1) from the primer extension done with HeLa Cells as the template. The probable position of the identified transcription start site is indicated by the arrow in FIG. 4. Putative transcription factor-binding sites were identified by their similarity to consensus sequences for known transcription factor-binding sites. The sequence motifs corresponding to Sp1, Ker1, and MyoD are also indicated in FIG. 4.

EXAMPLE 7

Detection of Heterozygous Mutations By PCR

A. Preparation of Genomic DNA

The genomic DNA used herein was obtained from human peripheral blood lymphocytes. The samples were prepared by the methods of Sambrook et al., *Molecular Cloning:A Laboratory Manual*, Second Edition, pp. 9.16–9.23, Cold Spring Harbor Laboratory Press, Cold Spring Harbor, N.Y. (1989).

B. Synthesis Of PCR Primers

The PCR primers used herein were synthesized as described in Example 5D. The specific primer sequences used and their annealing temperatures are given in Table 8, as SEQ ID NOS:69 to 112.

TABLE 8

| Exon Amplified | Sequence Of Primer (5'–3') | Annealing Temperature (°C.) | Size Of PCR Product (bp) |
|---|---|---|---|
| Exon 1 | TTCGCCGTTTGAATTGCTGC (SEQ ID NO:93) | 55 | 359 |
| Exon 1 (rev) | ACCGGTTCACACCAACTAGG (SEQ ID NO:94) | | |
| Exon 2 | GAGATAGGGTCATCATTGAAAC (SEQ ID NO:95) | 55 | 206 |
| Exon 2 (rev) | CATTAGCCATACTCTACTTGT (SEQ ID NO:96) | | |
| Exon 3 | GCTAATTTAACTCTGTAACTGC (SEQ ID NO:97) | 55 | 327 |
| Exon 3 (rev) | CACTGCAGCACAGACTAATGTGT (SEQ ID NO:98) | | |
| Exon 4 | TCTCTCCCTTTAACTGTGGGTTT (SEQ ID NO:99) | 55 | 245 |
| Exon 4 (rev) | GGAGTTGACGAGATTAATACCTG (SEQ ID NO:100) | | |
| Exon 5 | CTCTGTAACTGCTTATAATCCTG (SEQ ID NO:69) | 55 | 235 |
| Exon 5 (rev) | CTAGGAAACCTGTACAACTCC (SEQ ID NO:70) | | |
| Exon 6 | GGCTTATTGTGTGCTGATATC (SEQ ID NO:71) | 55 | 289 |
| Exon 6 (rev) | AGAGATCCTTAAGTCGTCATG (SEQ ID NO:72) | | |
| Exon 7 | CATGACGACTTAAGGATCTCTT (SEQ ID NO:101) | 55 | 196 |
| Exon 7 (rev) | CTCAGTTTCCAGAGTACAAAC (SEQ ID NO:102) | | |
| Exon 8 | CAGTTTCTGTGAGAGAGTACA (SEQ ID NO:73) | 55 | 283 |
| Exon 8 (rev) | GGCTTACCTGCTCCTGTATTT (SEQ ID NO:74) | | |
| Exon 9 | GTGAATTAAAGTCTTTCTGGCC (SEQ ID NO:103) | 55 | 277 |
| Exon 9 (rev) | ATCTTAGAAAGCAGACAGGGC (SEQ ID NO:104) | | |
| Exon 10 | GAGACATTTTATCCCCTTGTG (SEQ ID NO:105) | 55 | 289 |
| Exon 10 (rev) | TCCATGCCTCCAGTCTAAAGT (SEQ ID NO:106) | | |
| Exon 11 | GAGGAGGAATGGGCCTTTATT (SEQ ID NO:75) | 55 | 244 |
| Exon 11 (rev) | AACCCACAGAATAGGGCAGGA (SEQ ID NO:76) | | |
| Exon 12 | CACTTAAGTTGCACTGGGTA (SEQ ID NO:107) | 55 | 273 |
| Exon 12 (rev) | CAACAGGAAGTTGGTCTCATC (SEQ ID NO:108) | | |
| Exon 13 | TAAAAGGAAGAGCGGCTGTTT (SEQ ID NO:109) | 55 | 378 |
| Exon 13 (rev) | TTAAACCTAACTGCCACCCTC (SEQ ID NO:110) | | |
| Exon 14 | GGATACTGGCATTCTGTGTAAC (SEQ ID NO:77) | 55 | 197 |
| Exon 14 (rev) | ATTTCCAGATAGTAAGCCCCA (SEQ ID NO:78) | | |
| Exon 15 | AGCTTGGACGGAAGTCAGATC (SEQ ID NO:79) | 55 | 413 |
| Exon 15 (rev) | TCTAGCCAAACCTCGGGTAAC (SEQ ID NO:80) | | |
| Exon 16 | AATTGTAAACCTCTGCCC (SEQ ID NO:81) | 55 | 394 |
| Exon 16 (rev) | ATTTCCCAAGCTCATGCT | | |

TABLE 8-continued

| Exon Amplified | Sequence Of Primer (5'–3') | Annealing Temperature (°C.) | Size Of PCR Product (bp) |
|---|---|---|---|
| Exon 17 | (SEQ ID NO:82) AGCATGAGCTTGGGAAAT | 55 | 277 |
| Exon 17 (rev) | (SEQ ID NO:83) TGAAGACCTATCTTTGCC | | |
| Exon 18 | (SEQ ID NO:84) GTTCACAGAGCTCCTCACACT | 55 | 230 |
| Exon 18 (rev) | (SEQ ID NO:85) AGGCCACAGAGTCAACTATGG | | |
| Exon 19 | (SEQ ID NO:86) AGGTCCTATCACCAAGGGTGT | 55 | 250 |
| Exon 19 (rev) | (SEQ ID NO:87) GCTTAGTTACTTCTTCAAGGC | | |
| Exon 20 | (SEQ ID NO:88) GTAGCTGTTCCCTTTCTCCTA | 55 | 364 |
| Exon 20 (rev) | (SEQ ID NO:89) CCTCAACACTCATGAGAGTGA | | |
| Exon 21 | (SEQ ID NO:90) TGGTTTAGCACACCTCTTCAC | 55 | 325 |
| Exon 21 (rev) | (SEQ ID NO:91) GCTTAGCACAAACCCTGTTTC | | |
| Exon 22 | (SEQ ID NO:92) CTGAGCTATGTGCATTTGCA | 55 | 232 |
| Exon 22 (rev) | (SEQ ID NO:111) AAGGCTGCTGCTAAACAGAT (SEQ ID NO:112) | | |

C. PCR Amplification

The sample DNA was amplified in a Perkin-Elmer Cetus thermocycler. The PCR was performed in a 100 µl reaction volume using 2.5 units of recombinant Taq DNA-polymerase and 40 ng of genomic DNA. The reaction mixture was prepared according to the recommendations given in the Gene Amp DNA Amplification kit (Perkin-Elmer Cetus). The reaction mixture consisted of 50 mM/1 KCl, 10 mM/1 Tris-HCl (pH 8.3), 1.5 mM MgCl, 200 µM 20 each deoxynucleotide triphosphate and 1 µM of each primer. Thirty five (35) PCR cycles were carried out, with each cycle consisting of an initial denaturation step at 95° C. for one minute, one minute at the annealing temperature (55° C.), an extension step at 72° C. for one minute, and followed by a final incubation period at 72° C. for seven minutes. Suitable annealing temperatures are shown in Table 8 for each of the primers designed in accordance with this invention. Minor adjustments in the annealing temperatures may be made to accommodate other primers designed in accordance with this invention.

D. Amplification Products of PCR

The size of the amplification products produced by PCR are shown in Table 8 above. The lengths of the PCR products ranged from 196 bp to 413 bp.

E. Sequencing of PCR Products

Sequencing of the amplification products of pRb2/p130 can be conducted according to the method set forth in Example 5C above. Sequencing can also be performed by the chain termination technique described by Sanger et al., *Proc. Nat'l. Acad. Sci., U.S.A.* 74:5463–5467 (1977) or Sambrook et al., *Molecular Cloning: A Laboratory Manual*, Second Edition, pp. 13.42–13.77, Cold Spring Harbor Laboratory Press, Cold Spring Harbor, N.Y. (1989) with appropriate primers based on the pRb2/p130 genomic sequence described herein.

EXAMPLE 8

Detecting Mutations By SSCP Analysis

A. General Methods

The SSCP analysis was performed according to the methods of Orita et al., *Genomics* 5: 874–879 (1989) and Hogg et al., *Oncogene* 7: 1445–1451 (1992), each of which is incorporated herein by reference. For the SSCP analysis, amplification of the individual exons was, in some experiments, performed as described in Example 7 with the exception that 1 µCi of [$^{32}$P]dCTP (3000 Ci mmol$^{-1}$) was added to the mixture in order to obtain a labeled product. A 10% aliquot of the PCR-amplified product was diluted with a mixture of 10–20 µl of 0.1% SDS and 10 mM EDTA. Following a 1:1 dilution with 95% formamide, 2 mM EDTA, 0.05% bromophenol blue, and 0.05% xylene cyanol loading solution (United States Biochemicals, Ohio), the diluted sample was run on a 6% non-denaturing gel. The DNA was electrophoresed in TBE (0.09M Tris base, 0.09M boric acid and 2.5 mM EDTA) running buffer at constant wattage at room temperature. The gel was dried on filter paper and exposed to X-ray film for 12 to 72 hours without an intensifying screen.

Polymorphisms and mutations were detected by observing a shift in the electrophoretic mobility pattern of the denatured PCR-amplified product relative to a corresponding wild type sample or normal tissue sample from the same patient. Once a band shift was identified, the segment was sequenced to confirm the exact nature of the polymorphism or mutation.

B. Detection Of pRb2/p130 Gene Mutations In the CCRF-CEM Cell Line

DNA was extracted from the CCRF-CEM line (human lymphoblastoid cells), and amplified. For the amplification, 50 µl of the PCR reaction mix containing 4 ng of genomic DNA, 0.2 mM of each deoxynucleotide triphosphates, 2 U of Taq polymerase and 0.4 µM of each primer were used. Fifty-Five cycles of denaturation (95° C., 1 minute), annealing (55° C., 1 minute) and extension (72° C., 1 minute) were carried out in a thermal cycler. The SSCP analysis was performed using an MDE mutation detection kit (AT Biochem). The PCR products were heated to 95° C. for two minutes and placed directly on ice for several minutes. The samples were run through the MDE gel at 8 Watts constant power for eight hours at room temperature, in 0.6× TBE running buffer. The gel was stained for 15 minutes at room temperature in a 1 μg/ml ethidium bromide solution, made in 0.6× TBE buffer, and placed on a UV-transilluminator to visualize the bands. Exon 20 showed a different migration relative to the control, suggesting the presence of mutations.

The sequences of the PCR products were determined by automated DNA sequencing, using dideoxy-terminator reaction chemistry. Two point mutations were identified: ACC to GCC at position 2950 of SEQ ID NO:1, resulting in a threonine to alanine substitution; and CCT to CGT at position 3029 of SEQ ID NO:1, resulting in a proline to arginine substitution.

C. Detection of pRb2/p130 Gene Mutations in Other Cell Lines

Using the SSCP and DNA sequencing methods described above, mutations in the pRb2/p130 gene were identified in the following human tumor cell lines:

Jurkat cell line (human leukemia, T-cell lymphoblast): point mutations in exon 22;

K562 cell line (human chronic myelogenous leukemia, erythroblastoid cells): point mutations in exon 22, deletion in exon 21;

Molt-4 cell line (human T-cell leukemia, peripheral blood lymphoblast): point mutations in exon 21, mutation(s) in exon 22;

Daudi cell line (human thyroid lymphoma, lymphoblast B cell): point mutations and insertion in exon 19, point mutations and insertions in exon 21, mutations(s) in exon 22;

Cem cell line (lymphoblastoid cell line, T-lymphocytes): mutation(s) in exon 20, point mutations and insertions in exon 22;

Saos-2 cell line (human primary osteogenic sarcoma): point mutations and insertions in exon 21, point mutations and insertion in exon 22;

U2-Os cell line (human primary osteogenic sarcoma): point mutations in exons 19 and 21, point mutation and insertion in exon 22;

MG63 cell line (human osteosarcoma): point mutations in exon 19;

Hos cell line (human osteogenic sarcoma, TE85): point mutations in exon 19; insertions in exon 22;

U1752 cell line (human lung tumor): point mutations in exon 19, point mutations and insertion in exon 21, point mutation and insertion in exon 22;

H69 cell line (human lung tumor): point mutations in exon 21, point mutations and insertions in exon 22;

H82 cell line (human lung tumor): point mutations in exon 21; and

Hone cell line (human nasopharyngeal carcinoma): mutations and insertion in exon 21, mutation(s) in exon 22.

D. Detection of pRb2/p130 Gene Mutations in Primary Tumors

Using the SSCP and DNA sequencing methods described above, mutations in the pRb2/p130 gene were identified in the following primary human tumors:

13 NPC primary tumor (human nasopharyngeal carcinoma): point mutations in exon 21, point mutation and insertions in exon 22; and 5 NPC primary tumor (human nasopharyngeal carcinoma): point mutations and insertion in exon 22.

EXAMPLE 9

Detecting Mutations By The PRINS Technique

The PRINS technique was performed according to the method of Cinti et al., Nuc. Acids Res. Vol. 21, No. 24: 5799–5800 (1993) using human peripheral lymphocytes as the source of genomic DNA. The oligonucleotide primers were designed such that they included portions of the introns flanking exon 20. The sequences of the primers utilized to amplify exon 20 are listed in Table 8 above (SEQ ID NOS:89 and 90).

Human fixed metaphase chromosomes or interphase nuclei from PHA stimulated peripheral blood lymphocytes were spread onto glass slides and allowed to air dry for ten days. The DNA was dehydrated in an ethanol series (70%, 90%, and 100%) and then denatured by heating to 94° C. for 5 minutes. Using a reaction mixture containing 200 pmol of each oligonucleotide primer, 5 μl of 10×PCR Buffer II (AmpliTaq, Perkin-Elmer), 2 μl DIG DNA labeling mixture (1 mM dATP, 1 mM dCTP, 1 mM dGTP, 0.65 mM dTTP, 0.35 mM DIG-dUTP, Boehringer-Mannheim) and 2 Units of Taq I DNA polymerase (AmpliTaq, Perkin-Elmer), the samples were incubated for 10 minutes at 55° C. and for 30 minutes at 72° C. Suitable annealing temperatures for other primers designed in accordance with this invention are shown in Table 8. The samples were then washed two times in 2×SSC (pH 7.0) and in 4×SSC (pH 7.0) for 5 minutes at room temperature. The DNA samples were then placed in a solution of 4×SSC and 0.5% Bovine Serum Albumin (BSA) (pH 7.0), incubated at room temperature for 45 minutes with anti-Digoxigenin-FITC (Boehringer-Mannheim), and diluted 1:100 in 4×SSC and 0.5% BSA (pH 7.0). After washing the samples in 4×SSC and 0.05% Triton X-100, the samples were counterstained with 1 μg/ml Propidium Iodide (PI).

The slides were examined under a Confocal Laser Scanning Microscope (CLSM Sarastro, Molecular Dynamics). The FITC and PI signals were detected simultaneously, independently elaborated and the final projections were superimposed with a Silicon Graphic Computer Personal IRIS-4D/20 workstation.

Figure 6:
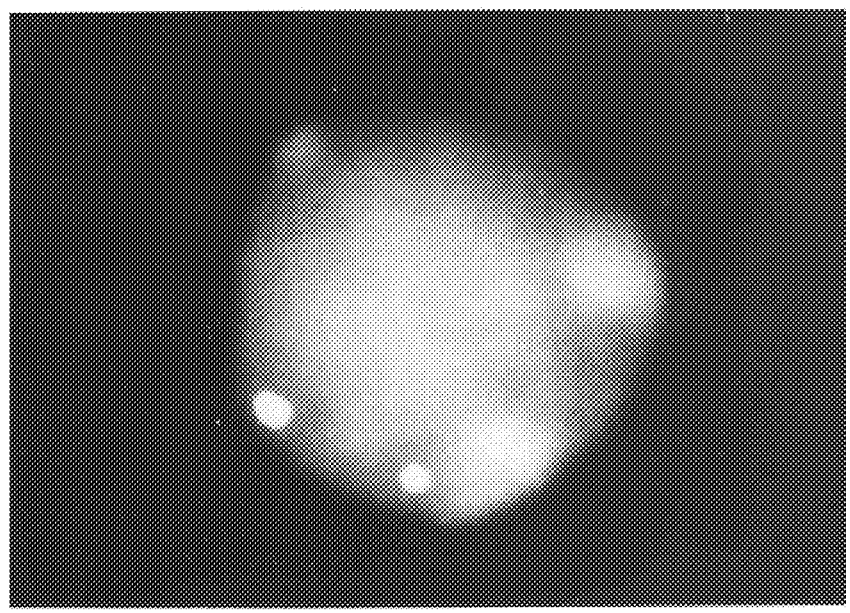
FIG. 6 illustrates two alleles containing exon 20 of the pRb2/p130 gene in the nucleus of a peripheral blood lymphocyte visualized through the use of the PRINS technique.

FIG. 6 shows the results of a PRINS reaction on normal human interphase nuclei. The bright spots correspond to a DNA segment containing exon 20 of pRb2/p130. This individual is homozygous for the presence of exon 20 of pRb2/p130. Had there been a mutation in exon 20 of this individual, either one or both of these areas would have been diminished in intensity or not visible in its entirety. To determine the exact nature of this mutation, the patient's pRb2/p130 DNA segment would be sequenced by methods known to those skilled in the art and compared to a wild type sample of pRb2/p130 DNA.

All the references discussed herein are incorporated by reference.

One skilled in the art will readily appreciate that the present invention is well adapted to carry out the ends and advantages mentioned, as well as those inherent therein. The nucleic acids, compositions, methods, procedures, and techniques described herein are presented as representative of the preferred embodiments, and are intended to be exemplary and not limitations on the scope of the invention. The present invention may be embodied in other specific forms without departing from the spirit or essential attributes thereof and, accordingly, reference should be made to the appended claims, rather than to the foregoing specification, as defining the scope of the invention.

I claim:

1. A method for determining a prognosis in a patient afflicted with cancer comprising determining the expression level of the pRb2/p130 gene in a sample from the patient, a decreased level of pRb2/p130 expression being indicative of an unfavorable prognosis.

2. The method of claim 1 wherein determining the expression level of the pRb2/p130 gene comprises determining the number of RNA transcripts of the gene relative to a standard number of said transcripts.

3. The method of claim 1 wherein determining the expression level of the pRb2/p130 gene comprises determining the level of the pRb2/p130 protein relative to a standard level of said protein.

4. The method of claim 3 wherein the level of the pRb2/p130 protein is determined by contacting the sample with an antibody which binds the pRb2/p130 protein.

5. The method of claim 1 wherein the sample is obtained from the patient prior to treatment of the patient with radiotherapy or chemotherapy.

6. The method of claim 1 wherein the cancer is a gynecologic cancer.

7. The method of claim 6 wherein the cancer is endometrial carcinoma.

8. The method of claim 7 wherein the sample comprises endometrial tissue.

9. The method of claim 8 wherein the endometrial tissue comprises a tumor.

10. The method of claim 6 wherein the cancer is ovarian cancer.

11. The method of claim 1 wherein the cancer is non-small cell lung cancer.

12. A method for identifying individuals at risk for cancer, or individuals at risk for the recurrence of cancer after treatment, comprising:

determining the level of expression of the pRb2/p130 gene in tissue sampled from an individual; and comparing the pRb2/p130 expression level in the sampled tissue with a normal pRb2/p130 expression level.

13. The method of claim 12 wherein determining the expression level of the pRb2/p130 gene comprises determining the number of RNA transcripts of the gene relative to a standard number of said transcripts.

14. The method of claim 12 wherein determining the expression level of the pRb2/p130 gene comprises determining the level of the pRb2/p130 protein relative to a standard level of said protein.

15. The method of claim 14 wherein the level of the pRb2/p130 protein is determined by contacting the sample with an antibody which binds the pRb2/p130 protein.

16. The method of claim 12 wherein the cancer is a gynecologic cancer.

17. The method of claim 16 wherein the cancer is endometrial carcinoma.

18. The method of claim 16 wherein the cancer is ovarian cancer.

19. The method of claim 12 wherein the cancer is non-small cell lung cancer.

20. A method for grading a cancer comprising determining the level of expression of the pRb2/p130 gene in a sample of tissue from a patient suffering from cancer, the level of expression being indicative of the grade of the cancer.

21. The method of claim 20 wherein determining the level of expression of the pRb2/p130 gene comprises determining the number of RNA transcripts of the gene in the sampled tissue relative to a standard number of said transcripts.

22. The method of claim 20 wherein determining the level of expression of the pRb2/p130 gene comprises determining the level of the corresponding pRb2/p130 protein in the sampled tissue relative to a standard level of said protein.

23. The method of claim 22 wherein the level of the protein in the sampled tissue is determined by an immunoassay whereby an antibody which binds said pRb2/p130 protein is contacted with said sampled tissue.

24. The method of claim 20 wherein the cancer is a gynecologic cancer.

25. The method of claim 24 wherein the cancer is endometrial carcinoma.

26. The method of claim 24 wherein the cancer is ovarian cancer.

27. The method of claim 20 wherein the cancer is non-small cell lung cancer.

28. The method of claim 27 wherein the cancer is a squamous cell carcinoma or an adenocarcinoma.

29. A method for detection of a cancerous disease state in a tissue of a patient comprising determining the level of the pRb2/p130 protein in a sample of the patient tissue relative to a standard level of said protein, a decreased level of said pRb2/p130 protein being indicative of the presence of cancer.

30. The method of claim 29 wherein the level of the pRb2/p130 protein is determined by contacting the sample with an antibody which binds the pRb2/p130 protein.

31. A method for detection of a gynecological cancer in a tissue of a patient comprising determining the expression level of the pRb2/p130 gene in a sample of the patient tissue, a decreased level of pRb2/p130 expression being indicative of the presence of gynecological cancer.

32. The method of claim 31 wherein the cancer is endometrial carcinoma.

33. The method of claim 31 wherein the cancer is ovarian cancer.

34. A method for detection of non-small cell lung cancer in a tissue of a patient comprising determining the expression level of the pRb2/p130 gene in a sample of the patient tissue, a decreased level of pRb2/p130 expression being indicative of the presence of non-small cell lung cancer.

* * * * *